(12) United States Patent
Paulus et al.

(10) Patent No.: US 9,658,195 B2
(45) Date of Patent: May 23, 2017

(54) ELECTRONIC CONTROL OF PH AND IONIC STRENGTH

(71) Applicants: Bio-Rad Laboratories, Inc., Hercules, CA (US); Technion Research & Development Foundation Ltd., Haifa (IL)

(72) Inventors: Aran Paulus, San Jose, CA (US); Camille Diges, Concord, CA (US); Roumen Bogoev, Hercules, CA (US); Sricharan Bandhakavi, Albany, CA (US); Annett Hahn-Windgassen, Sunnyvale, CA (US); Anton Posch, Grafting (DE); Elad Brod, Tivon (IL); Uri Sivan, Haifa (IL)

(73) Assignees: Bio-Rad Laboratories, Inc., Hercules, CA (US); Technion Research & Development Foundation Ltd., Haifa (IL)

( * ) Notice: Subject to any disclaimer, the term of this patent is extended or adjusted under 35 U.S.C. 154(b) by 475 days.

(21) Appl. No.: 13/768,253

(22) Filed: Feb. 15, 2013

(65) Prior Publication Data
US 2013/0220830 A1 Aug. 29, 2013

Related U.S. Application Data

(60) Provisional application No. 61/599,115, filed on Feb. 15, 2012, provisional application No. 61/722,612, filed on Nov. 5, 2012.

(51) Int. Cl.
*G01N 27/00* (2006.01)
*G01N 21/00* (2006.01)
(Continued)

(52) U.S. Cl.
CPC ............. *G01N 30/06* (2013.01); *B01D 57/02* (2013.01); *B01D 61/445* (2013.01); *B01D 61/46* (2013.01);
(Continued)

(58) Field of Classification Search
CPC .. B01D 61/445; B01D 57/02; B01D 2311/18; B01D 61/46; B01D 61/42; B01D 61/50;
(Continued)

(56) References Cited

U.S. PATENT DOCUMENTS 4,396,477 A 8/1983 Jain
4,868,130 A 9/1989 Hargreaves
(Continued)

FOREIGN PATENT DOCUMENTS

CN 102079781 A 6/2011
DE 102010017491 A1 12/2011
(Continued)

OTHER PUBLICATIONS

Office Action from U.S. Appl. No. 13/669,012, mailed May 4, 2015, 22 pages.
(Continued)

*Primary Examiner* — Dean Kwak
(74) *Attorney, Agent, or Firm* — Kilpatrick Townsend and Stockton LLP

(57) ABSTRACT

Apparatuses and methods for controlling ionic strength and/or pH of a solution are provided.

19 Claims, 34 Drawing Sheets

(51) Int. Cl.
*G01N 30/06* (2006.01)
*B01D 57/02* (2006.01)
*B01D 61/44* (2006.01)
*B01D 61/46* (2006.01)
*B01D 61/50* (2006.01)
*C25B 9/10* (2006.01)
*G01N 30/96* (2006.01)

(52) U.S. Cl.
CPC .............. *B01D 61/50* (2013.01); *C25B 9/10* (2013.01); *B01D 2311/18* (2013.01); *G01N 30/96* (2013.01)

(58) Field of Classification Search
CPC . B01D 61/54; C07K 1/28; C07K 1/36; G01N 27/44795; G01N 21/80; G01N 27/44773; G01N 27/26; G01N 30/06; G01N 30/96; C25B 9/10
USPC ................................. 422/62, 48, 82.03, 617
See application file for complete search history.

(56) References Cited

U.S. PATENT DOCUMENTS

| | | | |
|---|---|---|---|
| 4,880,513 | A | 11/1989 | Davis et al. |
| 4,900,414 | A | 2/1990 | Sibalis |
| 4,936,962 | A | 6/1990 | Hatzidimitriu |
| 5,045,204 | A | 9/1991 | Dasgupta et al. |
| 5,078,853 | A | 1/1992 | Manning et al. |
| 5,082,548 | A | 1/1992 | Faupel et al. |
| 5,160,594 | A | 11/1992 | Huff et al. |
| 5,198,086 | A | 3/1993 | Chlanda et al. |
| 5,437,774 | A | 8/1995 | Lausten et al. |
| 5,567,293 | A | 10/1996 | Paleologou et al. |
| 5,646,001 | A | 7/1997 | Terstappen et al. |
| 5,650,055 | A | 7/1997 | Margolis |
| 5,773,645 | A | 6/1998 | Hochstrasser |
| 6,027,643 | A | 2/2000 | Small |
| 6,077,434 | A * | 6/2000 | Srinivasan ............. G01N 30/96 204/520 |
| 6,084,091 | A | 7/2000 | Muller et al. |
| 6,129,832 | A | 10/2000 | Fuhr et al. |
| 6,225,129 | B1 | 5/2001 | Liu et al. |
| 6,660,150 | B2 | 12/2003 | Conlan et al. |
| 6,969,453 | B2 | 11/2005 | Ogle et al. |
| 6,969,614 | B1 | 11/2005 | Liotta et al. |
| 7,077,942 | B1 | 7/2006 | Conlan et al. |
| 7,390,389 | B2 | 6/2008 | Rossier et al. |
| 7,402,283 | B2 * | 7/2008 | Liu .......................... B01D 61/44 204/551 |
| 7,517,696 | B2 | 4/2009 | Srinivasan et al. |
| 7,615,354 | B2 | 11/2009 | Faupel et al. |
| 7,651,838 | B2 | 1/2010 | Paterlini-Brechot |
| 7,989,614 | B2 | 8/2011 | Deggerdal et al. |
| 8,293,095 | B2 | 10/2012 | Han et al. |
| 2002/0043462 | A1 | 4/2002 | Ivory et al. |
| 2003/0083823 | A1 | 5/2003 | Parekh et al. |
| 2003/0168576 | A1 | 9/2003 | Panattoni et al. |
| 2003/0205471 | A1* | 11/2003 | Speicher .......... G01N 27/44747 204/450 |
| 2003/0206894 | A1* | 11/2003 | De Boer ................... A61K 8/66 424/94.1 |
| 2003/0226752 | A1 | 12/2003 | Vigh |
| 2004/0242849 | A1 | 12/2004 | Rylatt et al. |
| 2005/0087445 | A1 | 4/2005 | Speicher et al. |
| 2006/0029978 | A1 | 2/2006 | O'Neill et al. |
| 2006/0037860 | A1 | 2/2006 | Ogle et al. |
| 2007/0163884 | A1 | 7/2007 | Strand et al. |
| 2007/0205106 | A1 | 9/2007 | Vigh et al. |
| 2008/0035484 | A1 | 2/2008 | Wu et al. |
| 2009/0101491 | A1 | 4/2009 | Bukshpan |
| 2009/0145777 | A1 | 6/2009 | Srinivasan |
| 2010/0155243 | A1 | 6/2010 | Schneider et al. |
| 2010/0307920 | A1 | 12/2010 | Sivan et al. |
| 2011/0195527 | A1 | 8/2011 | O'Neill et al. |
| 2012/0138468 | A1 | 6/2012 | Sivan et al. |
| 2012/0145548 | A1 | 6/2012 | Sivan et al. |
| 2013/0272952 | A1 | 10/2013 | Huss |

FOREIGN PATENT DOCUMENTS

| | | |
|---|---|---|
| EP | 0 979 868 A2 | 2/2000 |
| EP | 1456667 B1 | 9/2004 |
| EP | 1748340 A2 | 1/2007 |
| WO | WO 99/26724 A2 | 6/1999 |
| WO | WO 01/36449 A1 | 5/2001 |
| WO | 03/019172 A2 | 3/2003 |
| WO | 2004/024302 A1 | 3/2004 |
| WO | 2004/046351 A1 | 6/2004 |
| WO | WO 2004/083405 A2 | 9/2004 |
| WO | 2006/063625 A1 | 6/2006 |
| WO | 2007/051492 A1 | 5/2007 |
| WO | WO 2009/027970 A2 | 3/2009 |
| WO | 2009/133153 A1 | 11/2009 |
| WO | 2010/048173 A2 | 4/2010 |
| WO | WO 2010/118890 A1 | 10/2010 |
| WO | WO 2011/021195 A2 | 2/2011 |
| WO | WO 2011/021196 A2 | 2/2011 |

OTHER PUBLICATIONS

Lu et al., "A Microfabricated Device for Subcellular Organelle Sorting", *Anal. Chem.*, 76:5705-5712 (2004).
Munce et al., "Microfabricated System for Parallel Single-Cell Capillary Electrophoresis", *Anal. Chem*, 76:4983-4989 (2004).
Pospichal et al., "Micropreparative Focusing of Proteins in Carrier-Ampholyte-free Solultion with Electrically Controlled Composition of Electrolytes", *J. Microcolumn Separations*, 7(3): 213-219 (1995).
Prochakova et al., "The use of Carrier Ampholyte-Free Solelectric Focusing for Proteomic Analysis", *Chromatographia Supplement*, 67:S55-61 (2008).
Zhan et al., "Development of a simple amopholyte-free isoelectric focusing slab electrophoresis for protein fractionation", *Journal of Chromotograph A*, 1216:2929-2933 (2009).
The Extended European Search Report dated Jun. 22, 2015 for European Patent Application No. 12844702.6, 7 pages.
U.S. Appl. No. 14/468,730, filed Aug. 26, 2014 (108 pages).
Non-Final Office Action dated Aug. 5, 2015 for U.S. Appl. No. 13/803,564, 24 pages.
Notice of Allowance dated Sep. 8, 2015 for U.S. Appl. No. 13/669,012, 13 pages.
Armstrong et al., "Separating Microbes in the Manner of Molecules. 1. Capillary Electrokinetic Approaches", *Anal. Chem*, 71: 5465-5469 (1999).
Cabrera et al., "Continous concentration of bacteria in a microfluidic flow cell using electrokinetic techniques", *Eletrophoresis*, 22:355-362 (2001).
The Extended European Search Report dated Sep. 18, 2015 for European Patent Application No. 12845686.0, 11 pages.
Supplementary European Search Report dated Apr. 15, 2015 for EP Application No. 12845192.9, 6 pages.
Hughes et al., "Microfluidic integration for automated targeted proteomic assays", *Proceeding of the National Academy of Sciences*, 109(16):5972-5977 (2012).
Knittle et al., "Laser-induced flurescence detector for capillary-based isoelectric immunoblot assay", *Analytical Chemistry*, 79(24): 9478-9483 (2007).
O'Neill et al., "Isoelectric focusing technology quantifies protein signaling in 25 cells", *Proceedings of the National Academy of Sciences, National Academy of Sciences*, 103(44): 16153-16158 (2006).
Shimura et al., "Affinity Probe Capillary Electrophoresis: Analysis of Recombinant Human Growth Hormone with a Fluorescent Labeled Antibody Fragment", *Analytical Chemistry*, 66(1): 9-15 (1994).
The International Search Report and Written Opinion from PCT/US2012/063571, dated Feb. 20, 2013 (14 pages).

(56) References Cited

OTHER PUBLICATIONS

The International Search Report and Written Opinion from PCT/US2012/063601, dated Feb. 15, 2013 (12 pages).
The International Search Report and Written Opinion from PCT/US2013/026485, dated Apr. 19, 2013 (14 pages).
The International Search Report and Written Opinion from PCT/US2012/063502, dated Jan. 22, 2013 (13 pages).
The International Search Report and Written Opinion from PCT/US2013/032906, dated Jun. 14, 2013 (9 pages).
U.S. Appl. No. 13/668,651, filed Nov. 5, 2012 (43 pages).
U.S. Appl. No. 13/669,023, filed Nov. 5, 2012 (69 pages).
U.S. Appl. No. 13/669,012, filed Nov. 5, 2012 (42 pages).
U.S. Appl. No. 13/803,564, filed Mar. 14, 2013 (52 pages).
"Adjusting acidity with impunity." *PHYSorg.com*. Dec. 22, 2009. Retrieved at physorg.com/news180726696.html (author unknown).
"Isoelectric Focusing" from *European Pharmacopoeia Edition 5.0*, Chapter 2 "Methods of Analysis", Section 2.2.54 (p. 81-82). Published by the Council of Europe, Jun. 15, 2004.
"Isoelectric Focusing," AES Application Focus adapted from Chapter 7, Gel Electrophoresis of Proteins by David E. Garfin, pp. 197-268 in *Essential Cell Biology*, vol. 1: Cell Structure, a Practical Approach edited by John Davey and Mike Lord, Oxford University Press, Oxford UK (2003).
Ameridia, "Bipolar Membrane Electrodialysis—Applications of Bipolar Membrane Electrodialysis"; retrieved online at ameridia.com/htm/eba.html Jul. 12, 2011.
Ameridia, "Bipolar Membrane Electrodialysis—Process Description"; retrieved online at ameridia.com/htm/ebp.html Jul. 12, 2011.
Ameridia, "Bipolar Membrane Electrodialysis—Production of Organic or Amino Acids by Bipolar Membrane Electrodialysis"; retrieved online at ameridia.com/htm/ebc.html Jul. 12, 2011.
Amersham Pharmacia Biotech, "Hoefer IsoPrime IEF Purification Unit," User Manual (47 pages), 1999.
Bazinet et al.; "Bipolar Membrane Electroacidification to Produce Bovine Milk Casein Isolate"; *J. Agric. Food Chem.*; 47:5291-5296 (1999).
Bazinet et al.; "Effect of KCl and Soy Protein Concentrations on the Performance of Bipolar Membrane Electroacidification"; *J. Agric. Food Chem.*; 45:2419-2425 (1997).
Bazinet et al.; "Effect of Number of Bipolar Membranes and Temperature on the Performance of Bipolar Membrane Electroacidification"; *J. Agric. Food Chem.*; 45:3788-3794 (1997).
Biotech Daily, "Daily news on ASX-listed biotechnology companies," 4 pages, Oct. 10, 2008.
Cao, Liming (2005) *Protein Separation with Ion-exchange Membrane Chromatography*. (Master's Thesis) Retrieved online at wpi.edu/Pubs/ETD/Available/etd-050405-174109/.
Chen et al.; "Electrodialytic Membrane Suppressors for Ion Chromatography Make Programmable Buffer Generators"; *Anal. Chem.*; 84:67-75 (2012) ePub Nov. 21, 2011.
Chen et al.; "pH- and Concentration-Programmable Electrodialytic Buffer Generator"; *Anal. Chem.*; 84:59-66(2012) ePub Dec. 12, 2011.
Cheng et al.; "High-performance protein separation by ion exchange membrane partitioned free-flowisoelectric focusing system"; *Chem. Eng. Sci.*; 63:2241-2251 (2008).
Cheng et al.; "Micro-pH Control by Breaking Water and Its Applications". 15th International Conference on Miniaturized Systems for Chemistry and Life Sciences. Oct. 2-6, 2011, Seattle, Washington, USA (3 pages).
Cheng et al.; "Microscale pH Regulation by Breaking Water"; *Biomicrofluidics*; vol. 5, 046502, published online Nov. 2, 2011 (8 pages).
Cretich et al.; "Electroosmotic flow suppression in capillary electrophoresis: Chemisorption of trimethoxy silane-modified polydimethylacrylamide"; *Electrophoresis*; 26:1913-1919 (2005).
Das et al.; "Effects of separation length and voltage on isoelectric focusing in a plastic microfluidic device"; *Electrophoresis*; 27:3619-3626 (2006).
Denver Instrument, "Titration—Coulometric Karl Fischer Titration" brochure. (n.d.).
Dionex Corporation, "Eluent Suppressors for Ion Chromatography," Data Sheet (24 pages), 2010.
DKK-TOA Corporation, "AUT-701 Automatic Titrator" brochure. Jan. 10, 2008.
Douglas Instruments, "Oryx8" brochure. (n.d.).
Gregor, H.; "Ion-Exchange Membranes—Correlation Between Structure and Function"; *Pure Appl. Chem.*; 16(2-3)329-350 (1968).
Horvath et al.; "Multifunctional apparatus for electrokinetic processing of proteins"; *Electrophoresis*; 15:968-971 (1994).
Huang et al.; "Application of electrodialysis to the production of organic acids: State-of-the-art and recent developments"; *J. Membr. Sci.*; 288:1-12 (2007) ePub Nov. 25, 2006.
Huang et al.; "Capillary Isoelectric Focusing without Carrier Ampholytes" *Anal. Chem.*; 72:4758-4761 (2000).
Huang et al.; "Digitally Controlled Electrophoretic Focusing"; *Anal. Chem.*; 71(8):1628-1632 (1999) ePub Mar. 9, 1999.
Huang et al.; "The transitional isoelectric focusing process"; *Anal. Bioanal. Chem.*; 382:783-788 (2005).
Ivory, C.F.; "A Brief Review of Alternative Electrofocusing Techniques"; *Separation Science and Technology*; 35(11):1777-1793 (2000).
Jong et al., "Membranes and microfluidics: a review"; Lab Chip; (6): 1125-1139 (2006).
Karaltay Scientific Instruments, "Laboratory electrochemical analytical instruments—Automatic potentiometric titrators." 5 pages. (n.d.).
Karimi et al.; "Electroosmotic flow through polymer electrolyte membranes in PEM fuel cells"; *Journal of Power Sources*; 140:1-11 (2005).
Kelly et al.; "Electric field gradient focusing"; *J. Sep. Sci.*;28:1985-1993 (2005).
Kohlmann, F.J.; "What is pH and how is it measured?—A Technical Handbook for Industry"; Lit. No. G004. 24 pages. Hach Company (2003).
Lee et al.; "Polymer Electrolyte Membranes for Fuel Cells"; *J. Ind. Eng. Chem.*; 12(2):175-183 (2006).
Li et al.; "An electrokinetic bioreactor: using direct electric current for enhanced lactic acid fermentation and product recovery"; *Tetrahedron*; 60:655-661 (2004).
Lutin et al.; "Keep it natural ! Adjusting the pH of food products without chemical additives thanks to Bipolar Membrane Electrodialysis." Presented on May 15, 2007. NAMS 2007 Annual Meeting May 11-16, 2007, Orlando, Florida (3 pages).
Ly, Linda. (2008). *Development of Selective Electrophoresis for Proteins and Peptides within Proteomes*. (Doctoral Dissertation) Retrieved from web at http://www.unsworks.unsw.edu.au/primo_library/libweb/action/dlDisplay.do?vid=UNSWORKS&docId=unsworks_4279.
Mettler Toledo, "Compact Titrator G20" brochure. Sep. 2009.
Michél et al.; "Protein fractionation in a multicompartment device using Off-Gel™ isolectric focusing"; *Electrophoresis*; 24:3-11 (2003).
Montgomery et al.; "Dynamic Isoelectric Focusing for Proteomics"; *Anal. Chem.*; 78:6511-6518 (2006).
Nagasubramanian et al.; "Use of Bipolar Membranes for Generation of Acid and Base—An Engineering and Economic Analysis"; *J. Membr. Sci.*; 2:109-124 (1977).
Nguyen et al.; "A Water and Heat Management Model for Proton-Exchange-Membrane Fuel Cells"; J. Electrochem. Soc.; *J. Electrochem. Soc.*, 140(8):2178-2186 (Aug. 1993).
NuSep Press Release, "NuSep Increases Profit Forecast to $1m after it Acquires BioInquire and completes Placement at 30c"; 2009 (4 pages).
NuSep Press Release, "NuSep Investor Presentations"; 2009 (4 pages).
NuSep, "Desalting protein samples by electro-dialysis using the ProteomeSep MF10," Application Note NAN004 (2 pages), n.d.
NuSep, "ProteomeSep—MF10 Membrane Fractionation Instrument for protein separations," Operators Manual (22 pages), 2008.
NuSep, "Removal of urea from protein samples using the ProteomeSep MF10," Application Note NAN005 (2 pages), n.d.

(56) References Cited

OTHER PUBLICATIONS

NuSep, "Separation of protein based on isoelectric point using the NuSep MF10," Application Note NAN001, Insert PII-055v1.1 (2 pages), n.d.
NuSep, MF10 Brochure (8 pages), (2008).
NuSep. 2008 Annual Report. 64 pages.
Ogle et al.; "Preparative-scale isoelectric trapping separations using a modified Gradiflow unit"; *J. Chromatogr. A*; 979:155-161 (2002).
PC Cell GmbH, "PCCell ED 64 0 04" brochure. (n.d.).
Pearson et al.; "Production of synthetic ampholytes for isolectric focusing." (1979). *Nebraska Game and Parks Commission—White Papers, Conference Presentations, & Manuscripts*. Paper 13. Retrived onling at digitalcommons.unl.edu/nebgamewhitepap/13.
Piruska et al.; "The autofluorescence of plastic materials and chips measured under laser irradiation"; *Lab Chip*; 5:1348-1354 (2005) ePub Nov. 1, 2005.
Pospíchal et al.; "Analytical aspects of carrier ampholyte-free isoelectric focusing"; *J. Chromatog. A*; 918:195-203 (2001).
Pospíchal et al.; "Electrically controlled electrofocusing of ampholytes between two zones of modified electrolyte with two different values of pH"; *J. Chromatog.*; 638:179-186 (1993).
Pospíchal et al.; "Micropreparative Focusing of Proteins in Carrier-Ampholyte-free Solution with Electrically Controlled Compositions of Electrolytes"; *J. Microcolumn Separations*; 7(3):213-219 (1995).
Ramierz et al.; "Current-voltage curves of bipolar membranes"; *J. Appl. Phys.*, 72(1):259-264 (Jul. 1992).
Silvertand et al.; "Recent developments in capillary isoelectric focusing"; *J. Chromatog. A*; 1204:157-170 (2008).
Silvertand, Linda H.H. (2009) *Isoelectric Focusing: Sample Pretreatment—Separation—Hyphenation*. (Doctoral Dissertation) Retreived online at igitur-archive.library.uu.nl/dissertations/2010-0106-200200/UUindex.html.
Song et al.; "Fabrication and Characterization of Photpatterned Polymer Membranes for Protein Concentration and Dialysis in Microchips" in Hilton Head, South Carolina MEMS Workshop Jun. 6-10, 2004 (May 2004).
Standard Operating Procedure, "SOP for Gradiflow MF10 (prototype)," 6 pages, (2007).
TechniKrom, "New cGMP Bioprocessing Tool: Automated Rapid pH Adjustment Systems" brochure. (2006).
Thomas et al.; "Gradipore™—The Preparative Electrophoresis System, Gradiflow™"; Poster MB-04, 1 page, n.d.
Thomas et al.; "Preparative electrophoresis: a general method for the purification of polyclonal antibodies"; *J. Chromatogr. A*; 944:161-168 (2002).
Thomas et al.; Gradipore, "Comparison of Gradiflow and Affinity Chromatography Methods of Antibody Preparation," Gradipore Application Note AN3004 (Jul. 2003).
Thormann et al.; "High-resolution computer simulation of the dynamics of isoelectric focusing using carrier ampholytes: Focusing with concurrent electrophoretic mobilization is an isotachophoretic process"; *Electrophoresis*; 27:968-983 (2006).
Tongwen et al.; "Citric acid production by electrodialysis with bipolar membranes". *Chemical Engineering and Processing*; 41:519-524 (2002).
Walter et al.; "Protein microarrays: Reduced autofluorescence and improved LOD"; *Eng. Life Sci.*; 10(2):103-108 (2010).
Wei et al.; "One-step concentration of analytes based on dynamic change in pH in capillary zone electrophoresis"; *Anal. Chem.*; 74:934-940 (2002).
Wei et al.; "On-line concentration of proteins and peptides in capillary zone electrophoresis with an etched porous joint"; *Anal. Chem.*; 74:3899-3905 (2002).
Wellhausen et al.; "Facing Current Quantification Challenges in ProteinMicroarrays"; *J. Biomed. Biotechnol.*; vol. 2012, Article ID 831347, 8 pages, ePub Apr. 24, 2012.
Westermeier et al.; "Protein Detection Methods in Proteomics Research"; *Bioscience Reports*; 25(1/2):19-32 (2005).
Wilhelm, Friedrich G. (2001) Bipolar Membrane Electrodialysis. (Doctoral Thesis) Retrieved online at tup.utwente.nl/uk/catalogue/technical/electrodialysis.
Wong et al.; "Application of bipolar electrodialysis to *E. coli* fermentation for simultaneous acetate removal and pH control"; Biotechnol. Lett.; 32:1053-1057 (2010) ePub Apr. 11, 2010.
Wong, Michael. (2011) *Application of electrodialysis in integrated microbial fermentation and enzymatic biotransformation processes*. (Doctoral Thesis) Retreived online at discovery.ucl.ac.uk/1310480/1/1310480.pdf.
Wu et al.; "Isoelectric focusing sample injection for capillary electrophoresis of proteins"; *Electrophoresis*; 26:563-570 (2005).
Xu et al.; "Development of bipolar membrane-based processes"; *Desalination*; 140:247-258 (2001).
Xu et al.; "Electrodialysis-Based Separation Technologies: A Critical Review"; *American Institute of Chemical Engineers Journal*; 54(12):3147-3159 (2008) ePub Oct. 2, 2008.
Xu et al.; "Ion exchange membranes: State of their development and perspective"; *J. Membr. Sci.*; 263:1-29 (2005).
Zhang et al.; "Isoelectric Focusing Sample Injection for Capillary Zone Electrophoresis in a Fused Silica Capillary"; *Analytical Sciences*; 22:1039-1041 (Jul. 2006).
Zuo et al.; "A Method for Global Analysis of Complex Proteomes Using Sample Prefractionation by Solution Isoelectrofocusing Prior to Two-Dimensional Electrophoresis"; *Anal. Biochem.*; 284:266-278 (2000).
European Search Report mailed Oct. 13, 2015 in EP 13749830.9, 7 pages.

\* cited by examiner

ELECTRONIC CONTROL OF PH AND IONIC STRENGTH

CROSS-REFERENCE TO RELATED PATENT APPLICATIONS

The present patent application claims benefit of priority to U.S. Patent Application Nos. 61/599,115, filed Feb. 15, 2012 and 61/722,612, filed Nov. 5, 1012, both of which are incorporated by reference.

BACKGROUND OF THE INVENTION

International Patent Application Publication No. WO2009/027970 describes methods and devices (referred to herein as "proton/hydroxide injectors") useful in producing local concentrations of protons or hydroxide ions, proton or hydroxide concentration gradients, and desired proton or hydroxide concentration topographies in an environment, such as an electrolyte solution, a gel, and the like. International Patent Application Publication No. WO2011/021195 and WO2011/021196 describe methods and devices for isoelectric focusing proton/hydroxide injectors and also describes display of data. Proton/hydroxide injector technology can be used to affect the pH of the whole solution or to create changes in the pH at specific position or for specific region.

Briefly, in some embodiments, the proton/hydroxide injector comprises a small compartment adjacent to a channel, with a Pt electrode dipped inside it, and a bipolar membrane separating the compartment from the channel. See, e.g., FIGS. 1A-1B. A bipolar membrane is an ion-exchange membrane having a structure in which a cation-exchange membrane and an anion-exchange membrane are joined together, and allows for water molecules to be split into protons and hydroxide ions. Voltage applied between the compartment and the channel divided by the bipolar membrane leads to water splitting and injection of protons or hydroxide ions into the channel. Some advantages of this technology can include, for example, bubble-free water hydrolysis and injection of generated ions directly to the channel, allowing short response time (e.g., if desired, below 1 minute).

BRIEF SUMMARY OF THE INVENTION

In some aspects, an apparatus for controlling pH and/or ionic strength in a vessel is provided. In some embodiments, the apparatus comprises,
a. a vessel in fluid communication with a first side chamber and a second side chamber, wherein the vessel does not comprise an electrode;
b. the first side chamber divided from the vessel by an anion selective membrane or a cation selective membrane, and the first side chamber comprising an electrode; and
c. the second side chamber divided from the vessel by a membrane, the second vessel comprising an electrode, wherein the electrode of the first side chamber and the electrode of the second side chamber are capable of forming a circuit connected via a solution, when present, in the vessel and the first and second side chambers.

In some embodiments, the vessel is a reservoir.
In some embodiments, the vessel is tubing or a channel.
In some embodiments, the vessel is in fluid communication with a reservoir.
In some embodiments, the apparatus further comprises one or more of: a conductivity gauge in fluid communication with the vessel; a pH meter in fluid communication with the vessel; an electronic controller for the electrodes; and a pump positioned to pump a solution through the vessel.

In some embodiments, the vessel is in fluid communication with a chromatography column or other chromatography support, a mass spectrometer, capillary electrophoresis, or other analytical equipment.

In some embodiments, the vessel comprises a molecular weight cutoff membrane that prevents movement of macromolecules into the side chambers. In some embodiments, the vessel comprises a solution. In some embodiments, the solution comprises one or more cell. In some embodiments, the solution comprises macromolecules.

In some embodiments, the apparatus comprises:
i. an anion and proton injector comprising:
  a. the first side chamber in fluid communication with the vessel and divided from the vessel by an anion selective membrane, wherein the electrode of the first side chamber is a first cathode; and
  b. the second side chamber in fluid communication with the vessel and divided from the vessel by a bipolar membrane, wherein the electrode of the second side chamber is a first anode, and wherein the first anode and the first cathode are capable of forming a circuit connected via a solution, when present, in the vessel and the first and second chambers.

In some embodiments, the apparatus further comprises
ii. a cation and hydroxide ion injector comprising:
  a. a third side chamber in fluid communication with the vessel and divided from the vessel by a cation selective membrane, the third side chamber comprising a second anode; and
  b. a fourth side chamber in fluid communication with the vessel and divided from the vessel by a bipolar membrane, the fourth side chamber comprising a second cathode, wherein the second anode and the second cathode are capable of forming a circuit connected via a solution, if present, in the vessel and the third and fourth side chambers.

In some embodiments, the apparatus further comprises
iii. an anion and cation extractor comprising:
  a. the fifth side chamber in fluid communication with the vessel and divided from the vessel by a cation selective membrane, the fifth side chamber comprising a third cathode; and
  b. the sixth side chamber in fluid communication with the vessel and divided from the vessel by an anion selective membrane, the sixth side chamber comprising a third anode, wherein the third anode and the third cathode are capable of forming a circuit connected via a solution, when present, in the vessel and the fifth and second side chambers.

In some embodiments, the apparatus comprises:
i. a cation and hydroxide ion injector comprising:
  a. the first side chamber in fluid communication with the vessel and divided from the vessel by a cation selective membrane, wherein the electrode of the first chamber is a first anode; and
  b. the second side chamber in fluid communication with the vessel and divided from the vessel by a bipolar membrane, wherein the electrode of the second side chamber is a first cathode, wherein the second anode and the second cathode are capable of forming a circuit connected via a solution, if present, in the vessel and the first and second side chambers.

In some embodiments, the apparatus further comprises one or more of: a conductivity gauge in fluid communication with the vessel; a pH meter in fluid communication with the vessel; an electronic controller for the first cathode and first anode, and the second cathode and the second anode, if present; and a pump positioned to pump fluid a solution through the vessel.

In some embodiments, the vessel is in fluid communication with a chromatography column or other chromatography support, a mass spectrometer, capillary electrophoresis, or other analytical equipment.

In some embodiments, the apparatus comprises:
i. an anion and cation injector comprising:
a. the first side chamber in fluid communication with the vessel and divided from the vessel by an anion selective membrane, wherein the electrode of the first side chamber is a first cathode; and
b. the second side chamber in fluid communication with the vessel and divided from the vessel by a cation selective membrane, wherein the electrode of the second side chamber is a first anode, wherein the first anode and the first cathode are capable of forming a circuit connected via a solution, if present, in the vessel and the first and second side chambers.

In some embodiments, the apparatus further comprises one or more of: a conductivity gauge in fluid communication with the vessel downstream of the anion and cation injector; an electronic controller for the first cathode and first anode; and a pump positioned to pump a solution through the vessel.

In some embodiments, the vessel is in fluid communication with a chromatography column or other chromatography support, a mass spectrometer, capillary electrophoresis, or other analytical equipment.

In some embodiments, the apparatus further comprises
iii. an anion and proton injector comprising:
a. a third side chamber in fluid communication with the vessel and divided from the vessel by an anion selective membrane, the third side chamber comprising a second cathode; and
b. a fourth side chamber in fluid communication with the vessel and divided from the vessel by a bipolar membrane, the fourth side chamber comprising a second anode, wherein the second anode and the second cathode are capable of forming a circuit connected via a solution, if present, in the vessel and the third and fourth chambers;
and
iv. a cation and hydroxide ion injector comprising:
a. a fifth side chamber in fluid communication with the vessel and divided from the vessel by an cation selective membrane, the fifth side chamber comprising a third anode; and
b. a sixth side chamber in fluid communication with the vessel and divided from the vessel by a bipolar membrane, the sixth side chamber comprising a third cathode, wherein the third anode and the third cathode form a circuit connected via a solution in the vessel and the fifth and sixth side chambers.

In some embodiments, the apparatus further comprises:
v. a pH gauge in fluid communication with the vessel downstream of the anion and cation injector, the anion and proton injector, and the cation and hydroxide ion injector.

In some embodiments, the apparatus further comprises
ii. a proton injector and cation extractor comprising:
a. a third side chamber in fluid communication with the vessel and divided from the vessel by an cation selective membrane, the third side chamber comprising a second cathode; and
b. a fourth side chamber in fluid communication with the vessel and divided from the vessel by a bipolar membrane, the fourth side chamber comprising a second anode, wherein the second anode and the second cathode are capable of forming a circuit connected via a solution, if present, in the vessel and the third and fourth side chambers;
and
iii. a hydroxide ion injector and anion extractor comprising:
a. a fifth side chamber in fluid communication with the vessel and divided from the vessel by an anion selective membrane, the fifth side chamber comprising a third anode; and
b. a sixth side chamber in fluid communication with the vessel and divided from the vessel by a bipolar membrane, the sixth side chamber comprising a third cathode, wherein the third anode and the third cathode are capable of forming a circuit connected via a solution, if present, in the vessel and the fifth and sixth side chambers.

In some embodiments, the apparatus comprises:
i. a proton injector and cation extractor comprising:
a. the first side chamber in fluid communication with the vessel and divided from the vessel by an cation selective membrane, wherein the electrode of the first side chamber is a first cathode; and
b. a second side chamber in fluid communication with the vessel and divided from the vessel by a bipolar membrane, wherein the electrode of the second side chamber is a first anode, wherein the first anode and the first cathode are capable of forming a circuit connected via a solution, when present, in the vessel and the first and second side chambers.

In some embodiments, the apparatus further comprises:
ii. a hydroxide ion injector and anion extractor comprising:
a. a third side chamber in fluid communication with the vessel and divided from the vessel by an anion selective membrane, the third side chamber comprising a second anode; and
b. a fourth side chamber in fluid communication with the vessel and divided from the vessel by a bipolar membrane, the fourth side chamber comprising a second cathode, wherein the second anode and the second cathode are capable of forming a circuit connected via a solution, if present, in the vessel and the third and fourth side chambers.

In some embodiments, the apparatus comprises:
i. a hydroxide ion injector and anion extractor comprising:
a. the first side chamber in fluid communication with the vessel and divided from the vessel by an anion selective membrane, wherein the electrode of the first chamber is a first anode; and
b. the second side chamber in fluid communication with the vessel and divided from the vessel by a bipolar membrane, wherein the electrode of the second side chamber is a first cathode, wherein the first anode and the first cathode are capable of forming a circuit connected via a solution, if present, in the vessel and the first and second side chambers.

In some embodiments, the apparatus further comprises one or more of: a conductivity gauge in fluid communication with the vessel downstream of the proton injector and cation extractor; a pH meter in fluid communication with the vessel; an electronic controller for the first cathode and first anode; and a pump positioned to pump a solution through the vessel.

In some embodiments, the vessel is in fluid communication with a chromatography column or other chromatography support, a mass spectrometer, capillary electrophoresis, or other analytical equipment.

In some embodiments, the apparatus comprises:
  i. an anion and cation extractor comprising:
    a. the first side chamber in fluid communication with the vessel and divided from the vessel by a cation selective membrane, wherein the electrode of the first chamber is a first cathode; and
    b. the second side chamber in fluid communication with the vessel and divided from the vessel by an anion selective membrane, wherein the electrode of the second side chamber is a first anode, wherein the first anode and the first cathode are capable of forming a circuit connected via a solution, when present, in the vessel and the first and second side chambers.

In some embodiments, the apparatus further comprises one or more of: a conductivity gauge in fluid communication with the vessel downstream of the anion and proton extractor; a pH meter in fluid communication with the vessel; an electronic controller for the first cathode and first anode; and a pump positioned to pump a solution through the vessel.

In some embodiments, the vessel is in fluid communication with a chromatography column or other chromatography support, a mass spectrometer, capillary electrophoresis, or other analytical equipment.

In some embodiments, the vessel (as described in any of the embodiments herein) comprises a solution comprising cells, nucleic acids, or proteins.

In some embodiments, the apparatus (as described in any of the embodiments herein) does not comprise a vacuum or other device for removal of excess gas.

Methods of controlling pH and/or ionic strength of an aqueous solution are also provided. In some embodiments, the method comprises providing the apparatus as described in any of the embodiments described herein, wherein the vessel and the side chambers contain the solution; and applying a current between the electrode in the first side chamber and the electrode in the second side chamber, thereby changing the concentration of ions in the solution in the vessel, thereby controlling pH and/or ionic strength of the solution.

In some embodiments, the apparatus comprises a reservoir containing the solution in fluid communication with the vessel and the method further comprises pumping the solution from the reservoir through the vessel during the applying. In some embodiments, the method comprises after the applying, transferring the solution to a chromatography column or other chromatography support, a mass spectrometer, capillary electrophoresis, or other analytical equipment.

In some embodiments, the vessel comprises a cell or a biological macromolecule and a molecular size cut-off membrane in the vessel prevents the cell or macromolecule from moving out of the vessel.

In some embodiments, the vessel comprises a cell or a biological macromolecule, and the applying of the current results in a reduction of ions in the solution in the vessel. In some embodiments, the ions are selected from the group consisting of peptides, nucleotides, oligonucleotides, ionic detergents and ionic metabolites.

In some embodiments, the vessel comprises a cell or a biological macromolecule, and the applying of the current results in an increase of ions in the solution in the vessel. In some embodiments, the macromolecule is a protein or a nuclei acid.

In some embodiments, the apparatus in the method comprises:
  i. an anion and proton injector comprising:
    a. the first side chamber in fluid communication with the vessel and divided from the vessel by an anion selective membrane, wherein the electrode of the first side chamber is a first cathode; and
    b. the second chamber in fluid communication with the vessel and divided from the vessel by a bipolar membrane, wherein the electrode of the second side chamber is a first anode, and wherein the first anode and the first cathode form a circuit connected via the solution in the vessel and the first and second side chambers; and
the applying comprises applying a current across the first cathode and first anode thereby transporting anions from the first side chamber into the vessel and protons from the second side chamber into the vessel.

In some embodiments, the apparatus in the method further comprises:
  ii. a cation and hydroxide ion injector comprising:
    a. a third side chamber in fluid communication with the vessel and divided from the vessel by a cation selective membrane, the third side chamber comprising a second anode; and
    b. a fourth side chamber in fluid communication with the vessel and divided from the vessel by a bipolar membrane, the fourth side chamber comprising a second cathode, wherein the second anode and the second cathode form a circuit connected via the solution in the vessel and the third and fourth chambers; and
the applying further comprises applying a current across the second cathode and second anode thereby transporting cations from the third side chamber into the vessel and hydroxide ions from the fourth side chamber into the vessel.

In some embodiments, the apparatus in the method further comprises:
  iii. an anion and cation extractor comprising:
    a. the fifth side chamber in fluid communication with the vessel and divided from the vessel by a cation selective membrane, the fifth side chamber comprising a third cathode; and
    b. the sixth side chamber in fluid communication with the vessel and divided from the vessel by an anion selective membrane, the sixth side chamber comprising a third anode, wherein the third anode and the third cathode form a circuit connected via the solution in the vessel and the fifth and second side chambers; and
the applying further comprises applying a current across the third cathode and third anode thereby transporting cations from the vessel into the fifth side chamber and anions from the vessel into the sixth side chamber.

In some embodiments, the apparatus in the method comprises:
  i. a cation and hydroxide ion injector comprising:
    a. the first side chamber in fluid communication with the vessel and divided from the vessel by a cation selective membrane, wherein the electrode of the first side chamber is a first anode; and
    b. the second side chamber in fluid communication with the vessel and divided from the vessel by a bipolar membrane, wherein the electrode of the second side chamber is a first cathode, wherein the second anode and the second cathode form a circuit connected via the solution in the vessel and the first and second side chambers; and the applying comprises applying a current across the first cathode and first anode thereby transporting cations from the first side chamber into the vessel and hydroxide ions from the second side chamber into the vessel.

In some embodiments, the apparatus in the method comprises:

i. an anion and cation injector comprising:
  a. the first side chamber in fluid communication with the vessel and divided from the vessel by an anion selective membrane, wherein the electrode of the first chamber is a first cathode; and
  b. the second side chamber in fluid communication with the vessel and divided from the vessel by a cation selective membrane, wherein the electrode of the second side chamber is a first anode, wherein the first anode and the first cathode form a circuit connected via the solution in the vessel and the first and second side chambers; and the applying comprises applying a current across the first cathode and first anode thereby transporting anions from the first side chamber into the vessel and cations from the second side chamber into the vessel.

In some embodiments, the apparatus in the method further comprises:

iii. an anion and proton injector comprising:
  a. a third side chamber in fluid communication with the vessel and divided from the vessel by an anion selective membrane, the third side chamber comprising a second cathode; and
  b. a fourth side chamber in fluid communication with the vessel and divided from the vessel by a bipolar membrane, the fourth chamber comprising a second anode, wherein the second anode and the second cathode form a circuit connected via a solution in the vessel and the third and fourth side chambers;
and
iv. a cation and hydroxide ion injector comprising:
  a. a fifth side chamber in fluid communication with the vessel and divided from the vessel by an cation selective membrane, the fifth side chamber comprising a third anode; and
  b. a sixth side chamber in fluid communication with the vessel and divided from the vessel by a bipolar membrane, the sixth side chamber comprising a third cathode, wherein the third anode and the third cathode form a circuit connected via a solution in the vessel and the fifth and sixth side chambers; and the applying further comprises:

applying a current across the second cathode and second anode thereby transporting anions from the third side chamber into the vessel and protons from the fourth side chamber into the vessel; and applying a current across the third cathode and third anode thereby transporting cations from the fifth side chamber into the vessel and hydroxide ions from the sixth side chamber into the vessel.

In some embodiments, the apparatus in the method further comprises
  ii. a proton injector and cation extractor comprising:
    a. a third side chamber in fluid communication with the vessel and divided from the vessel by an cation selective membrane, the third side chamber comprising a second cathode; and
    b. a fourth side chamber in fluid communication with the vessel and divided from the vessel by a bipolar membrane, the fourth side chamber comprising a second anode, wherein the second anode and the second cathode form a circuit connected via the solution in the vessel and the third and fourth side chambers;
and
  iii. a hydroxide ion injector and anion extractor comprising:
    a. a fifth side chamber in fluid communication with the vessel and divided from the vessel by an anion selective membrane, the fifth side chamber comprising a third anode; and
    b. a sixth side chamber in fluid communication with the vessel and divided from the vessel by a bipolar membrane, the sixth side chamber comprising a third cathode, wherein the third anode and the third cathode form a circuit connected via the solution in the vessel and the fifth and sixth chambers; and the applying further comprises:

applying a current across the second cathode and second anode thereby transporting cations from the vessel into the third side chamber and protons from the fourth side chamber into the vessel; and applying a current across the third cathode and third anode thereby transporting anions from the vessel into the fifth side chamber and hydroxide ions from the sixth side chamber into the vessel.

In some embodiments, the apparatus in the method the apparatus comprises:

i. a proton injector and cation extractor comprising:
  a. the first side chamber in fluid communication with the vessel and divided from the vessel by an cation selective membrane, wherein the electrode of the first side chamber is a first cathode; and
  b. a second side chamber in fluid communication with the vessel and divided from the vessel by a bipolar membrane, wherein the electrode of the second side chamber is a first anode, wherein the first anode and the first cathode form a circuit connected via the solution in the vessel and the first and second side chambers; and the applying comprises applying a current across the first cathode and first anode thereby transporting cations from the vessel into the first side chamber into the vessel and protons from the second side chamber into the vessel.

In some embodiments, the apparatus in the method further comprises:

ii. a hydroxide ion injector and anion extractor comprising:
  a. a third side chamber in fluid communication with the vessel and divided from the vessel by an anion selective membrane, the third side chamber comprising a second anode; and
  b. a fourth side chamber in fluid communication with the vessel and divided from the vessel by a bipolar membrane, the fourth side chamber comprising a second cathode, wherein the second anode and the second cathode form a circuit connected via the solution in the vessel and the third and fourth side chambers; and the applying further comprises applying a current across the second cathode and second anode thereby transporting anions from the vessel into the third side chamber and hydroxide ions from the fourth side chamber into the vessel.

In some embodiments, the apparatus in the method comprises:
i. a hydroxide ion injector and anion extractor comprising:
  a. the first side chamber in fluid communication with the vessel and divided from the vessel by an anion selective membrane, wherein the electrode of the first side chamber is a first anode; and
  b. the second side chamber in fluid communication with the vessel and divided from the vessel by a bipolar membrane, wherein the electrode of the second side chamber is a first cathode, wherein the second anode and the second cathode form a circuit connected via the solution in the vessel and the third and fourth side chambers; and the applying comprises applying a current across the first cathode and first anode thereby transporting anions from the vessel into the first side chamber and hydroxide ions from the second side chamber into the vessel.

In some embodiments, the apparatus in the method comprises:
i. an anion and cation extractor comprising:
  a. the first side chamber in fluid communication with the vessel and divided from the vessel by a cation selective membrane, wherein the electrode of the first side chamber is a first cathode; and
  b. the second side chamber in fluid communication with the vessel and divided from the vessel by an anion selective membrane, wherein the electrode of the second side chamber is a first anode, wherein the first anode and the first cathode form a circuit connected via the solution in the vessel and the first and second side chambers; and the applying comprises applying a current across the first cathode and first anode thereby transporting cations from the vessel into the first side chamber and anions from the vessel into the second side chamber.

In some embodiments of the methods as described above or elsewhere herein, the cation is selected from the group consisting of sodium, lithium, magnesium, calcium, ammonium, trizma (Tris), and imidazole.

In some embodiments of the methods as described above or elsewhere herein, the anion is selected from the group consisting of chloride, fluoride, bromide, phosphate, citrate, and glutathione.

In some embodiments of the methods as described above or elsewhere herein, the solution comprises a cell, nucleic acid or a protein.

In some embodiments, the solution comprises a chemical or enzymatic reaction (e.g., a DNA or RNA polymerase or other reaction) and the reaction is controlled by changing the pH or ionic strength of the solution.

In some embodiments, the solution comprises at least a first and second component that bind to each other and the pH and/or ionic strength of the solution is changed to regulate binding of the components. In some embodiments, the pH and/or ionic strength of the solution is changed to increase binding of the components. In some embodiments, the pH and/or ionic strength of the solution is changed to decrease binding of the components. In some embodiments, at least one of the components is an affinity agent, e.g., an antibody, aptamer, or nucleic acid.

Methods of delivering a charged molecule to, or removing a charged molecule from, a cell sample are also provided. In some embodiments, the method comprises providing the apparatus as described herein having (i) a sample comprising one or more cell in the vessel and (ii) a charged molecule in a side chamber and/or the vessel; applying a current across the electrodes through an aqueous solution in the vessel thereby (i) delivering the charged molecule from a side chamber into the vessel or (ii) removing the charged molecule from the vessel into a side chamber.

In some embodiments, the method further comprises removing one or more cell from the vessel after the applying.

In some embodiments, the electrode in the first side chamber is a cathode and the electrode in the second side chamber is an anode. In some embodiments, the charged molecule is positively charged and the positively charged molecule is transferred by the current to the vessel from the second side chamber. In some embodiments, the charged molecule is negatively charged and the negatively charged molecule is transferred by the current to the vessel from the first side chamber.

In some embodiments, the electrode in the first side chamber is an anode and the electrode in the second side chamber is a cathode. In some embodiments, the charged molecule is positively charged and the positively charged molecule is transferred by the current from the vessel to the second side chamber. In some embodiments, the charged molecule is negatively charged and the negatively charged molecule is transferred by the current to the vessel from the first side chamber.

In some embodiments, the charged molecule has a mass between 300-1500 daltons.

In some embodiments, the cell is a prokaryotic cell. In some embodiments, the cell is a eukaryotic cell. In some embodiments, the cell is an animal cell. In some embodiments, the cell is a plant cell. In some embodiments, the cell is a fungal cell. In some embodiments, the cell is a human cell.

DEFINITIONS

A side chamber is in "fluid communication" with a vessel if water molecules can pass back and forth between the chamber and vessel. Generally, an orifice or opening in the vessel will connect with an orifice or opening of the side chamber. "Fluid communication" as used here includes situations in which a selective membrane divides the side chamber and the vessel. In this case, the membrane allows water molecules to pass (though possibly significantly impeded) between the side chamber and vessel but may not allow all components (e.g., cations, anions, etc.) to pass through the membrane.

A "vessel" refers to a container capable of holding a fluid. For example, the vessel can be a tubing, channel, or other configuration for moving a fluid from one point to another in a continuous fashion, or can be a "reservoir," i.e., a discrete container, for example such as a beaker, flask, bucket or other container.

An "anion selective membrane" is a membrane that prevents or greatly inhibits movement of cations across the membrane, but allows for movement of anions across the membrane. Examples of anion selective membranes include, e.g., FAB membranes (Fumatech, Germany).

A "cation selective membrane" is a membrane that prevents or greatly inhibits movement of anions across the membrane, but allows for movement of cations across the membrane. Examples of cation selective membranes include, e.g., FKS membranes (Fumatech, Germany).

A "bipolar membrane" refers to a membrane comprising a cation-exchange membrane and an anion-exchange membrane which are joined together and allow for water splitting via electrolysis. See, e.g., International Patent Application Publication No. WO2011/021195 and WO2011/021196.

DETAILED DESCRIPTION OF THE INVENTION

I. Introduction

Figure 1A:
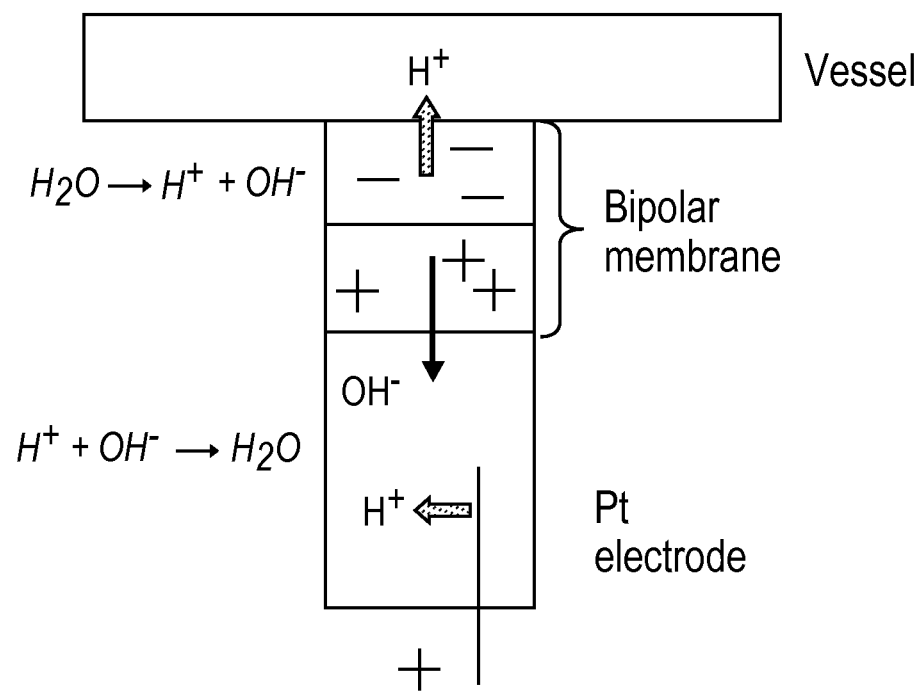
FIGS. 1A and 1B illustrate a proton and hydroxide injector, respectively, comprising a small compartment adjacent to the channel, with a Pt electrode dipped inside it, and a bipolar membrane separating the compartment from the channel.
Figure 1B:
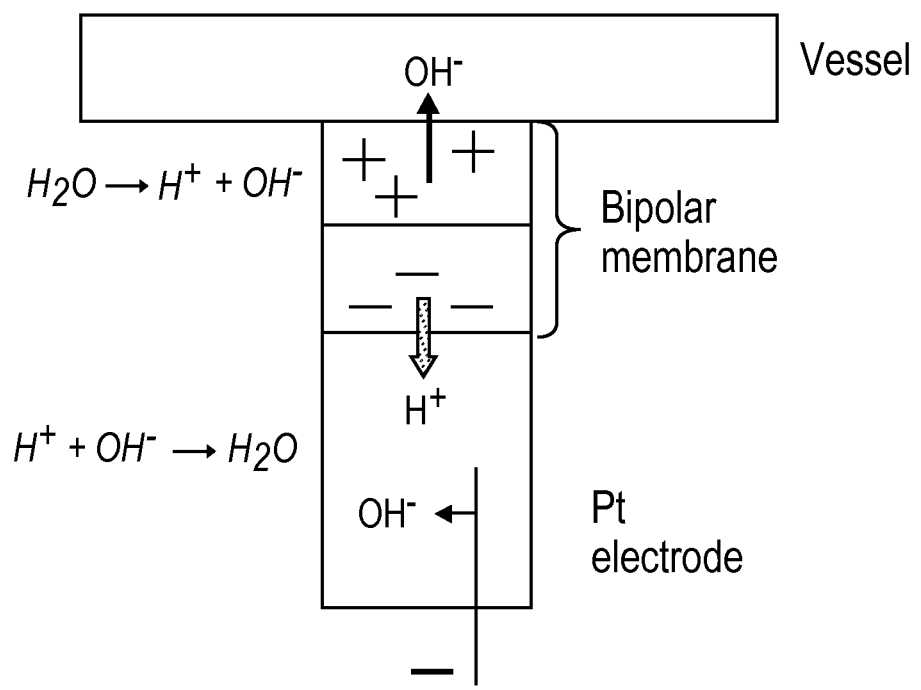

It has been determined that various configurations of electrolysis units in combination with chambers separated from a vessel by anion selective, cation selective, or bipolar membranes allow for control of pH and/or ionic strength within the vessel. By using one of the configurations described herein, or by combing the configurations of side chamber pairs, desired control of pH and/or ionic strength can be achieved. The apparatuses having these configurations are useful for any situation for which the pH or ionic strength is to be controlled, including but not limited to, uses in chromatography. The apparatus can also be used, for example, to set the buffering capacity in a vessel and titrate its pH to a desired value.

In some embodiments, the vessel contains a macromolecule or one or more cells, and ions can be injected into the vessel or extracted from the vessel as desired (and optionally adjusting the pH of the solution in the vessel). In some embodiments, the vessel comprises one or more cells and the ion-selective membranes are sufficient for retaining the cell(s) in the vessel. In some embodiments, the cells or macromolecules are retained in the vessel with a molecular weight cut-off (e.g., a dialysis) membrane, thereby allowing retention of the cell or macromolecules in the vessel or a sub-portion of the vessel defined by the molecular weight cutoff membrane.

Simple salt ions can be extracted from, or injected into, the vessel having the macromolecules or cells, thereby, for example, providing a dialysis function. Alternatively, charged drugs or other charged molecules can be injected into the vessel solution (thereby contacting them to the macromolecules or cells therein). This is useful, for example, for testing the effect of the charged molecules on the cells or macromolecules. In another embodiment, charged molecules (e.g., charged metabolites that otherwise inhibit cell growth or division) can be removed from proximity of the cells in the vessel.

II. Apparatus Configurations

As described in more detail below, various apparatus configurations are provided either that inject ions of various kinds into a solution in a vessel, or that extract ions from the solution in the vessel. In some embodiments in which ions are extracted, other ions are simultaneously injected into the solution in the vessel.

A basic exemplary apparatus configuration comprises a vessel for containing a solution in fluid communication with a first and a second side chamber, wherein the first side chamber is divided from the vessel by a first selective membrane and the second side chamber is divided from the vessel by a second selective membrane. Selective membranes allows for movement of certain ions (e.g., cations or anions or protons and hydroxide ions) while inhibiting transport of other ion types across the membrane. In many embodiments, the first and second selective membranes have different selective properties. Examples of selective membranes include, e.g., anion selective membranes, cation selective membranes, and bipolar selective membranes. The first and second side chambers comprise an electrode (an anode in one side chamber and a cathode in the other side chamber) to form a circuit via the solution in the side chambers and the vessel. Two side chambers that form a circuit are referred to herein as a "side chamber pair" or a "pair of side chambers." In some embodiments, a third or further additional side chamber can interact with the pair, for example, where a cathode of one side chamber generates current for two or more different anode-containing side chambers (or vice versa in which there is one anode and two or more cathodes). Depending on the direction of the current and the type of selective membrane dividing the side chambers from the vessel, the solution in the vessel will accumulate protons, hydroxide ions, other anions or cations, or in some configurations will transfer cations and/or anions to the side vessels. By controlling the current and configuration, one can thereby control the pH and/or ionic strength of the solution in the vessel.

Pairs of side chambers, each forming a separate circuit through the solution in the vessel and having different configurations of selective membranes, can be combined, to achieve desired results. For example, a first and second side chamber can form a circuit and inject chloride anions and protons into the solution while a third and fourth side chamber can form a separate circuit and inject hydroxide and sodium cations into the solution in the vessel, thereby raising the ionic strength, and depending on the relative flow of protons and hydroxide ions, altering the pH. As explained below, many other configurations are possible. The use of "first," "second," "third," etc., is used for convenience in labeling and is not intended to impart any other meaning In some embodiments, only one side chamber is in fluid communication with the vessel and separated by a membrane (e.g., a bipolar, cation-exchange, or anion-exchange membrane) In some aspects a second side chamber can also be in fluid communication with the vessel wherein the second side chamber is separated by a neutral (passing anions and cations) membrane.

The membranes "divide" the side chambers from the vessel by forming a barrier that separates solution in a side chamber from the vessel, e.g., at least to the level of solution in the vessel. For example, in embodiments in which the vessel is open at the top (or alternatively, has a top cover that can be removed), the membranes can be designed to completely divide a side chamber from the vessel at least up to the level of solution in the vessel and/or side chamber, or to a level designated as a maximum for solution loading. As desired, the membranes can be designed to be higher than the solution level so as to avoid accidental transfer (e.g., splashing) from one portion to another. If desired, the membranes can be "framed" by a solid material (e.g., plastic) or otherwise anchored between the vessel and the side chamber. The ion specific membranes can be further supplemented with neutral membranes such as dialysis membranes to prevent, e.g., contact of molecules in the solution with the ion specific or bipolar membranes.

The electrodes can be formed from any conducting or semi-conducting substance. For example, in some embodiments, one or more electrode comprises a metal. In some embodiments, the metal is zinc, copper, or platinum. For example, the electrodes can be platinum or can be platinum-plated. Generally, maximal surface area for electrodes is desirable. A flattened electrode, for example, provides more surface area than a wire.

The vessel can be any container capable of holding or moving a solution (e.g., a flow cell or a tube). The vessel size will be selected to the desired use of the resulting solution. For example, vessel capacity can range from the nano to microliter range, to the 10 s of liters or more. In some embodiments, the vessel acts as a reservoir, and in some embodiments, can include a stirring device to circulate the solution. In some embodiments, the vessel is tubing or a channel, thereby allowing for flow of the solution, e.g., from a reservoir to a destination. In these embodiments, it is possible, for example, for the solution to receive cations or anions or have cations or anions extracted from the solution as the solution moves passed the side chambers. The side chamber capacity can be adapted as needed, and can similarly be capable of holding or moving a solution (e.g., flow cell or a tube). For example, in some embodiments, side chamber capacity can be between 100 micro liter and 10 s of liters.

In some embodiments, the system includes a mixing system such that the pH of the solution is uniform. Examples of mixing systems include, e.g., a magnetic stir-bar or a sonic/ultrasonic mixer. This system also can involve a feedback between the absolute electrode and the proton/hydroxide injector system in which one is measuring the pH while the other is adjusting it. The feedback exists, for instance, to ensure that the proton/hydroxide injector technology stops injecting ions when the correct pH is reached. Volumes of the target solution can vary as desired. In some embodiments, the method is applied to small solution volumes (0.1-10 mL) however the volume can also be significantly larger for some applications. This could also be made as a sterile attachment to the base to enable adjusting the pH of sterile solutions without contaminating them.

In some embodiments, the vessel can be designed to be loaded with a sample or at least part of the vessel will be designed to accept a sample. For example, in some embodiments, the apparatus is designed to rest on a lab bench or table top, and the top of the apparatus, or at least the vessel, is removable so that a sample can be loaded into the vessel. The area of the vessel designed for receipt of the sample will be enclosed by a molecular weight cutoff membrane such that, when a sample is loaded into the vessel, molecules having a mass larger than the cutoff cannot escape. The molecular weight cutoff of the molecular weight cutoff membrane can be selected as desired, for example, selected such that a macromolecule in the sample is retained. A variety of dialysis membranes are commercially available for such purposes but one can consider also gels, molecular sieves, etc. In some embodiments, the vessel is a tube, channel or flow cell, thereby allowing for movement of the solution in the vessel to a subsequent destination following adjustment of the ion concentration and/or pH of the solution. Optionally, the dialysis membrane mentioned above can be in the form of a channel, tube, or otherwise to allow for macromolecule flow during the process.

In some embodiments, the molecular cutoff membrane is simply a bag placed in the vessel, where the bag comprises the sample. The apparatus can be implemented with various forms and shapes of the ion exchange and dialysis membrane. For example, instead of a dialysis bag, the molecular cutoff membrane can be applied as a layer on the surface of the ion-exchange membranes and/or as a membrane across the vessel. In some embodiments, the vessel is lined with the molecular cutoff membrane such that the entire vessel can function as a sample loading area.

Generally, it is contemplated that the vessel itself will not contain, or be in contact with, an electrode capable of forming a circuit with the side chamber electrodes (electrodes will be in the side chambers, separated by one or more membrane from the vessel). This will avoid possible interference by an electrode with components of the solution in the vessel. For example, it is otherwise possible that an electrode in the vessel would unduly attract or denature molecules (e.g., biomolecules) in the vessel. A lack of an electrode in the vessel also helps avoidance of bubbles, which might otherwise form, e.g., via electrolysis. Thus, in some embodiments, the apparatus does not include a vacuum or other device for removal of gas (e.g., $H_2$ and $O_2$ generated by electrolysis).

In some embodiments, a pump can be included to move the solution through the vessel, e.g., from a reservoir through the vessel, passed the side chambers, to a destination. The precise position of the pump can vary as desired, and can be located, for example, between a reservoir and the side chambers, between side chambers, or between the destination and the side chambers. In some embodiments fluids are circulated by electro-osmotic pumping.

In some embodiments, the apparatus can comprise a conductivity gauge, a pH gauge, or both. The precise position of the gauge(s) can vary as desired. For embodiments where the solution flows passed the pair(s) of side chambers, the gauges will be downstream of the side chambers to monitor the conductivity and/or pH of the output. Signals from the gauges can be transferred back to a central electronic controller thereby allowing for modification of the side chamber(s) current to regulate pH and conductivity as desired. Independent electronic control of the voltage and/or current of each side chamber pair can be controlled via an electronic controller, which can comprise a computer, microprocessor, etc. For example, as shown in FIGS. 2-10, terminal 1 controls the buffer pumping rate from the reservoir into the destination (a chromatography column in the figures). In some embodiments the resulting pH and salt concentration can be tuned by varying the fluid flow rate at given electrical injection currents.

Figure 32:
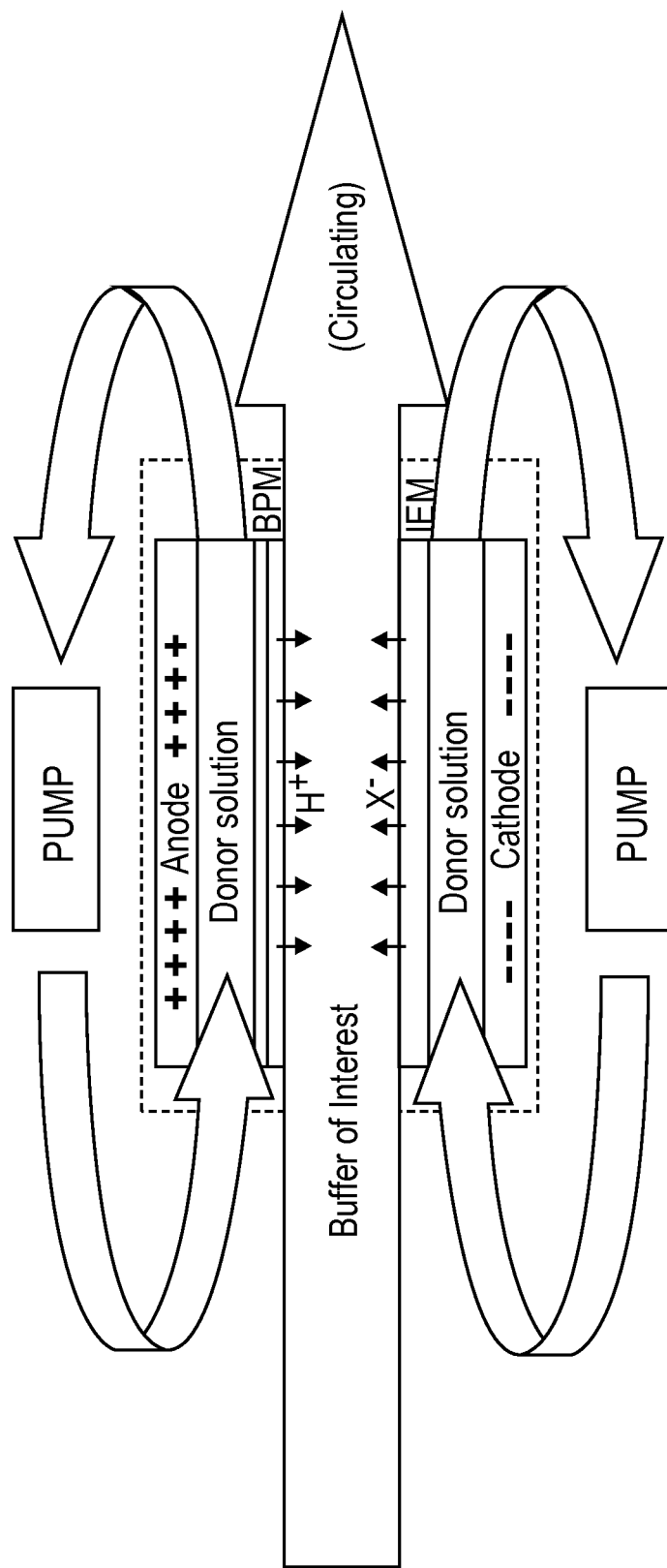
FIG. 32 illustrates a configuration for vessel and side chambers. The particular membrane types and electrode orientation can be changed as described herein.
Figure 33:
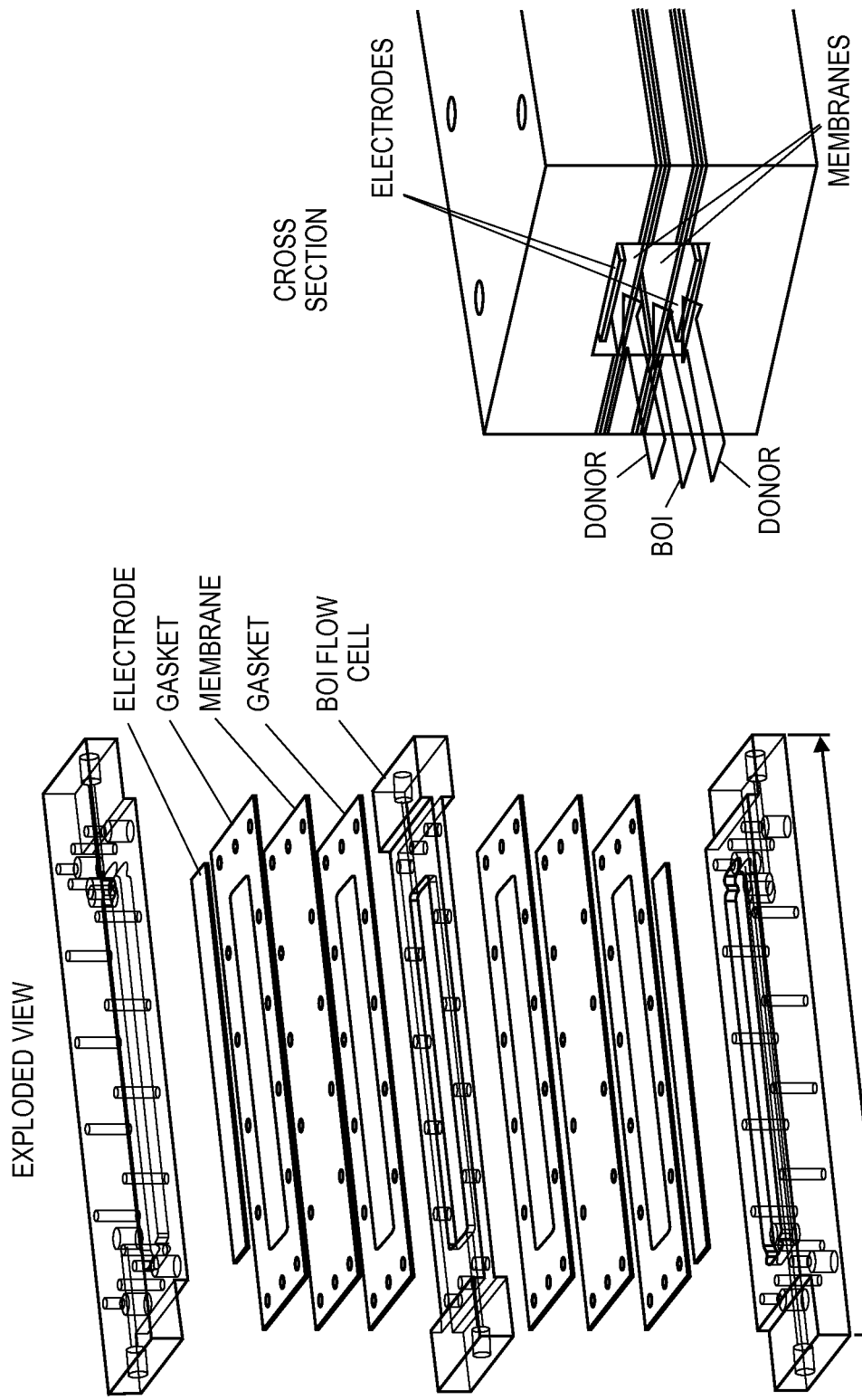
FIG. 33 illustrates schematic configuration for the configuration depicted in FIG. 32.

In some embodiments the fluid in the side chambers and/or vessel is circulated or replenished continuously. For example, FIG. 32 depicts an embodiments in which solution from side chambers on either side of the vessel are circulated with a pump, thereby continuously flowing the solution within the side chambers. Similarly, the solution in the vessel itself can be circulated—either recycled or from a reservoir to a destination, flowing passed the side chambers. While FIG. 32 depicts a bipolar membrane separating one side chamber, and an anion exchange membrane separating a second side chamber from the vessel, it should be appreciated that any combination of membranes, as well as any orientation of electrodes are possible and are provided for herein. FIG. 33 depicts one possible design for such an "in-line" pH and/or ionic strength tuner.

In some embodiments the cathode and anode electrodes are further separated from the side chambers by additional ion selective or bipolar membranes. To the extent chlorine emission from exposure of the solution to the electrodes is an issue, an extra cation-exchange membrane can be employed as a restriction membrane to isolate the anode. This membrane restricts Cl− ions from reaching the anode and turning into chlorine gas. In some embodiments, a high concentration salt solution in the donor solution (i.e., in a side chamber) was found to eliminate chlorine formation.

By applying the appropriate voltage to the anode and cathode and therefore a current across the solution in the side chambers and vessel, charged molecules will move accordingly. In some embodiments, the charged molecules can be added to the anode or cathode side chamber, and subsequently the voltage is applied, thereby delivering the charged molecule to the vessel at a time determined by the user.

Figure 11:
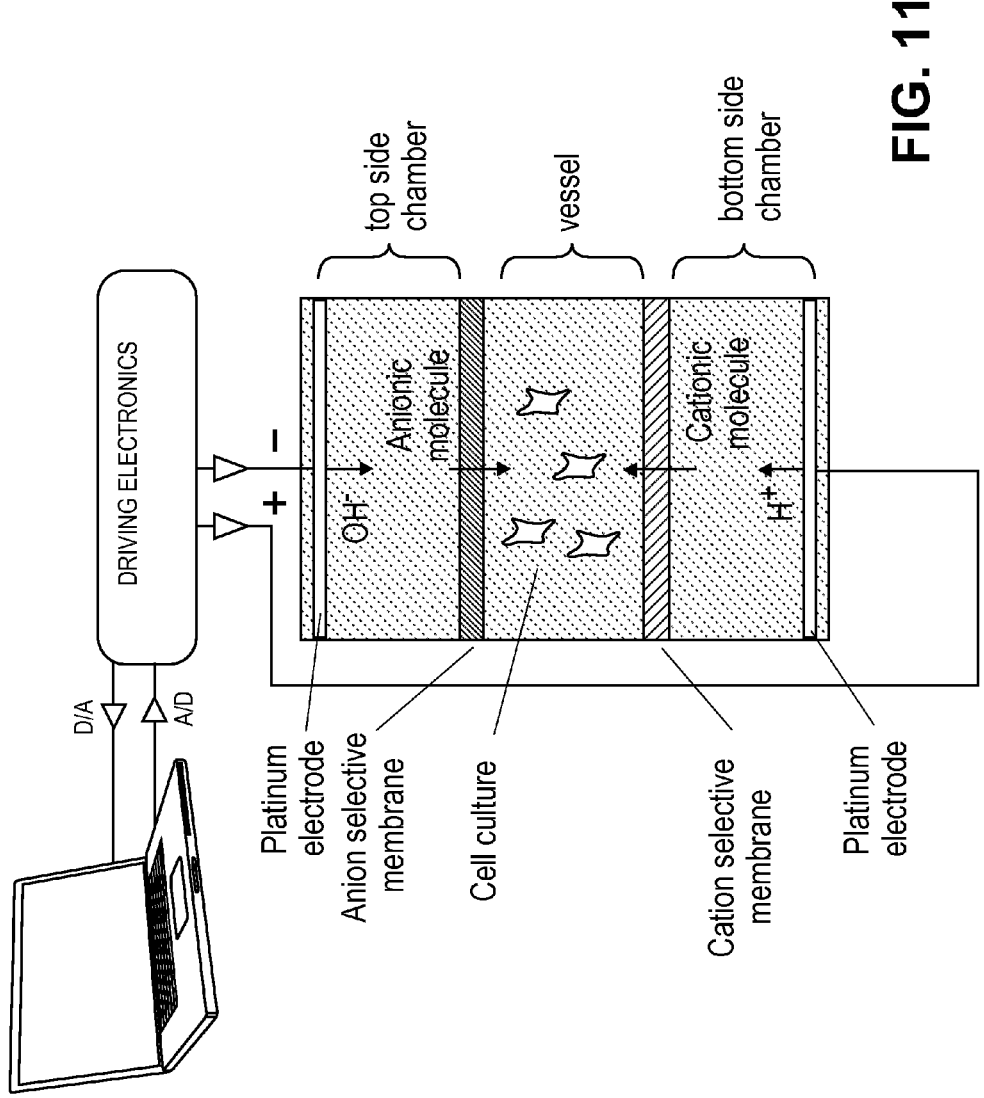
FIG. 11 depicts an apparatus that delivers charged molecules (anion or cation molecules) into a vessel comprising cells. As shown in the Figure, anionic molecules, if present, will flow into the vessel (i.e., the middle compartment) from the cathode side chamber (top compartment) upon application of an electric current. Similarly, cationic molecules, if present, will flow into the vessel from the anode side chamber (bottom compartment) upon application of an electric current.

The direction of movement of the molecule will depend on the charge of the molecule and the polarity of the applied voltage. In the configuration of FIG. 11, for example, positively charged molecules positioned in the anode side chamber will move through the cation selective membrane between the anode side chamber and vessel and will thus enter the vessel upon application of sufficient current. Because the membrane separating the cathode side chamber and the vessel is an anion selective membrane, the positively charged molecules will remain in the vessel and will not continue into the cathode side chamber.

Movement of a negatively-charged molecule works the same way, but in a reverse direction. Thus, a negatively-charged molecule in the cathode side chamber, upon application of a current between the anode and the cathode, will move through the anion selective membrane dividing the cathode side chamber and the vessel, and will enter the vessel. Because the membrane between the vessel and the anode side chamber is a cation selective ion, the negatively-charged molecule will not pass through and thus will remain in the vessel.

Accordingly, one can place cells in the vessel, and depending on the charge of the molecule of interest, charged molecules can be placed in the anode or cathode side chamber. Once voltage is applied, the charged molecules will move into the vessel, thereby bringing the charged molecules into proximity to the cells. If desired, cells can be subsequently removed from the vessel (e.g., after a specific amount of time following administration of the current) and, if desired, analyzed.

Any charged molecule can be brought into proximity of cells in the vessel as outlined above. In some embodiments, the charged molecule is a drug or other bioactive molecule. While simple ions will also move in the apparatus described, in many embodiments, the charged molecule will be larger than simple ions. Thus, in some embodiments, the charged molecule will have a molecular mass of more than 50, 100, 150, 200, or 250 daltons, e.g., 200-20,000 daltons, e.g., 200-1,000 daltons, e.g., 300-1500 daltons, etc.

Figure 12:
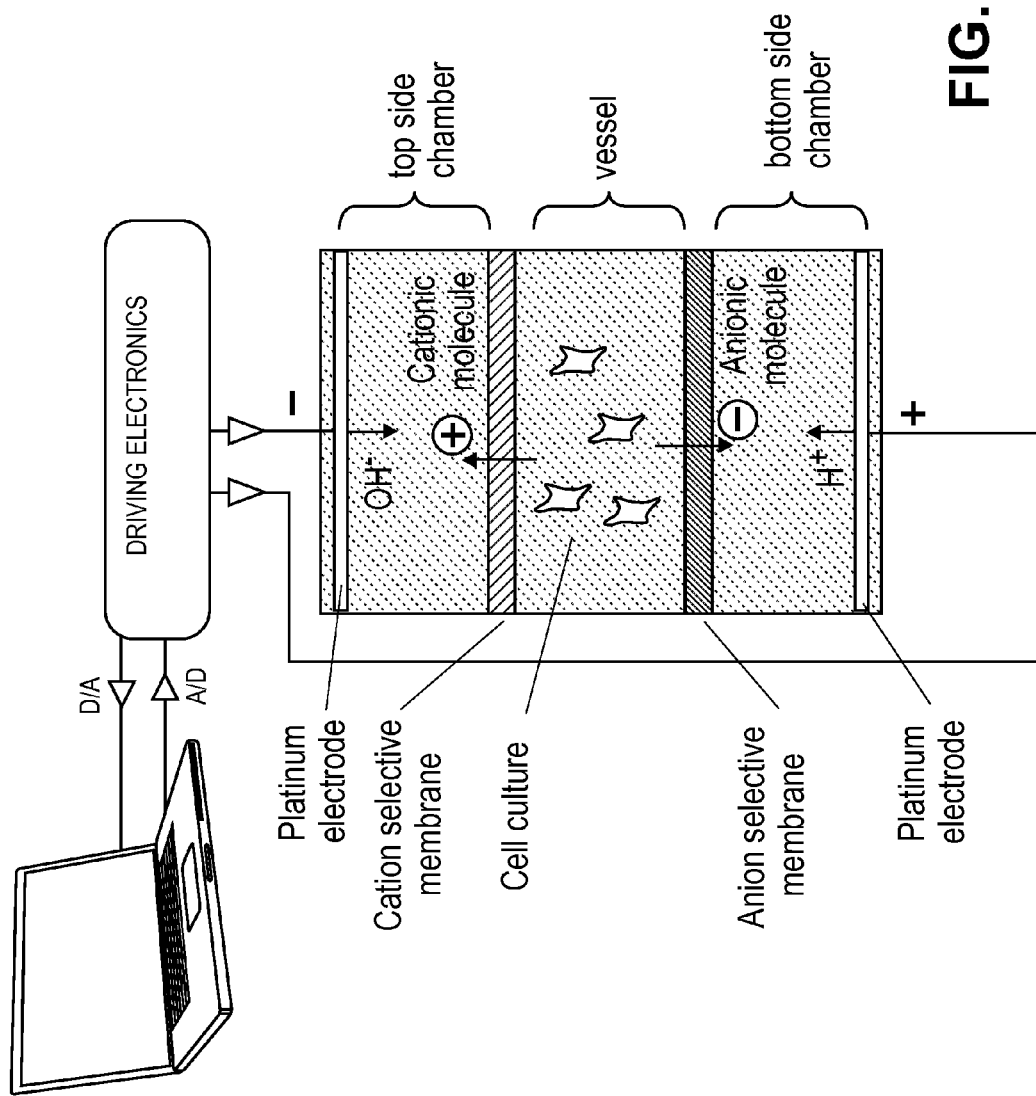
FIG. 12 depicts an apparatus that removes charged molecules (anionic or cation molecules) from the vessel (e.g., the middle compartment) comprising cells. As shown in the Figure, cationic molecules, if present, will flow from the vessel into the cathode (top) side chamber upon application of an electric current. Similarly, anionic molecules, if present, will flow from the vessel into the anode (bottom) side chamber upon application of an electric current.
Figure 13:
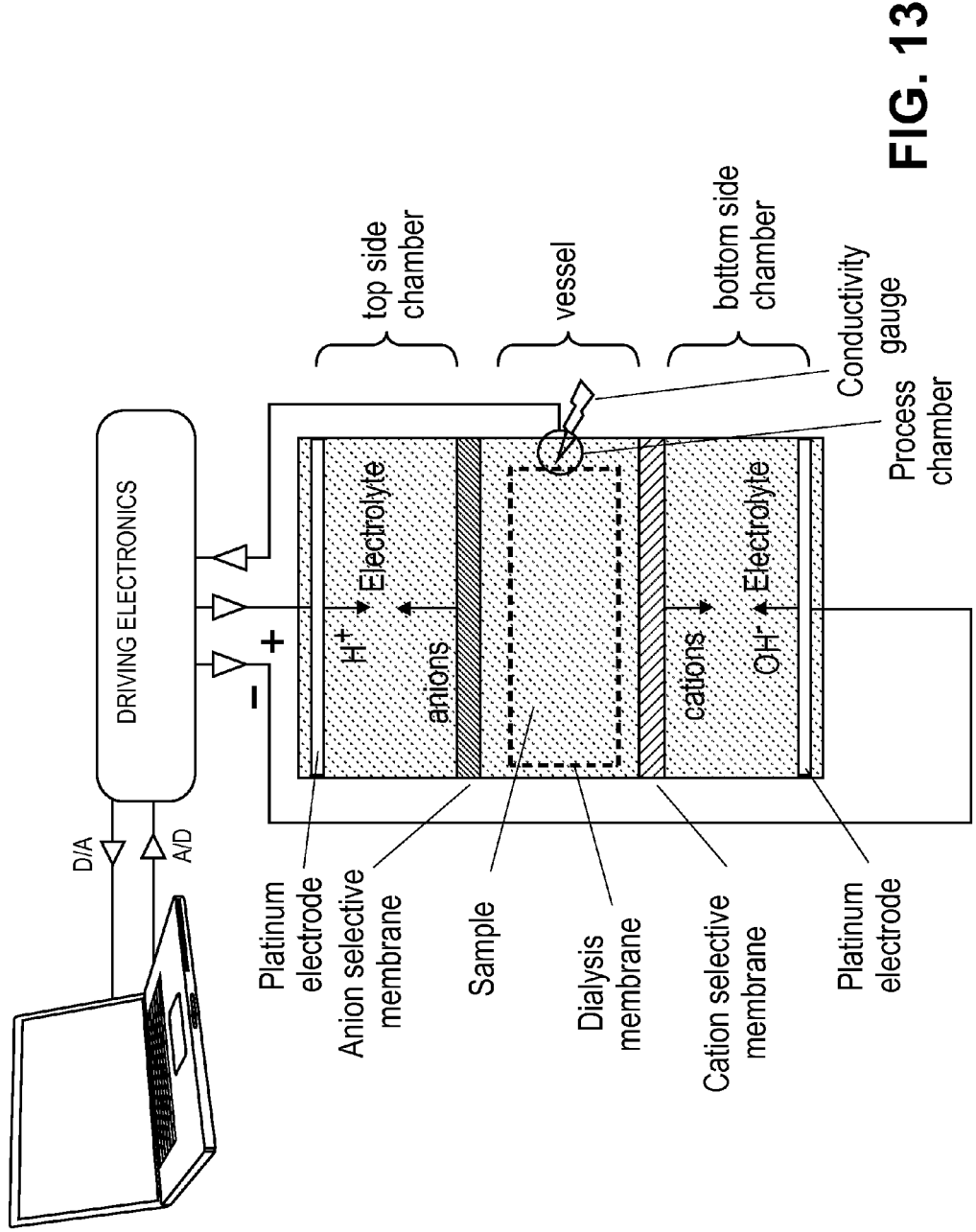
FIG. 13 illustrates an exemplary apparatus configuration for desalting a macromolecule sample.

In other configurations, the apparatus can be used to remove charged molecules from the vessel, thereby removing charged molecules from proximity of one or more cell in the vessel. In these embodiments, the apparatus configured such that the cathode side chamber is divided from the vessel by a cation selective membrane and the vessel is divided from the anode side chamber by an anion selective membrane. In these embodiments, the cathode and anode are capable of forming a circuit via a solution in the apparatus, through the cathode side chamber, vessel, and anode side chamber. In these embodiments, the vessel can be designed to hold one or more cells (e.g., a cell culture, suspension or adherent, etc.), thereby positioning the cells in the circuit between the side chambers. An example of this conformation is depicted in FIG. 12.

By applying the appropriate voltage to the anode and cathode and therefore a current across the solution in the apparatus, charged molecules in the vessel will move accordingly. In some embodiments, the charged molecules can be added to the vessel (e.g., to incubate with the one or more cell present in the second portion), and subsequently the voltage can be applied, thereby moving the charged molecule from the vessel at a time determined by the user.

Again, the direction of movement of the molecule will depend on the charge of the molecule. For example, in the example depicted in FIG. 12, positively charged molecules positioned in the vessel will move through the cation selective membrane between the vessel and cathode side chamber upon application of sufficient current and will enter the cathode side chamber.

Movement of a negatively-charged molecule works the same way, but in a reverse direction. Thus, a negatively-charged molecule in the vessel, upon application of a current between the anode and the cathode, will move through the anion selective membrane dividing the vessel and anode side chamber, and will enter the anode side chamber.

Any charged molecule can be removed from proximity of cells in the vessel as outlined above. In some embodiments, the charged molecule is a drug or other bioactive molecule. While simple ions will also move in the apparatus described, in many embodiments, the charged molecule will be larger than simple ions. Thus, in some embodiments, the charged molecule will have a molecular mass of more than 50, 100, 150, 200, or 250 daltons, e.g., 200-20,000 daltons, e.g., 200-1,000 daltons, e.g., 300-1500 daltons, etc. In some embodiments, the charged are metabolites of the cell. In some processes, removal of metabolites may be advantageous if the metabolite is suppressing the further growth or production of the desired product or is the product itself (for example production of amino acids).

The precise size, shape, and volume of the vessel and side chambers thereof can vary as desired. The vessel volume can range from the nano to microliter range, to the 10s of liters or more. It is generally expected that the vessel will be made from non-conducting material (e.g., plastic).

Any type of cells or cell source can be used in the apparatus. For example, the cells can be from a cell culture, can be primary cells derived from tissue, or can be tissue. Cells can be in suspension or adherent. Cells from any species can be used. For example, the cells can be eukaryotic cells or prokaryotic cells. Exemplary eukaryotic cells can include plant, animal, or fungal cells. Exemplary animal cells include, but are not limited to, human, primate, bovine, mouse, insect, or rat cells. Alternatively, the cells can be bacterial cells, e.g., gram positive or gram negative bacterial cells.

A. Ion Injectors

A number of different ion injectors can be designed.

Figure 2:
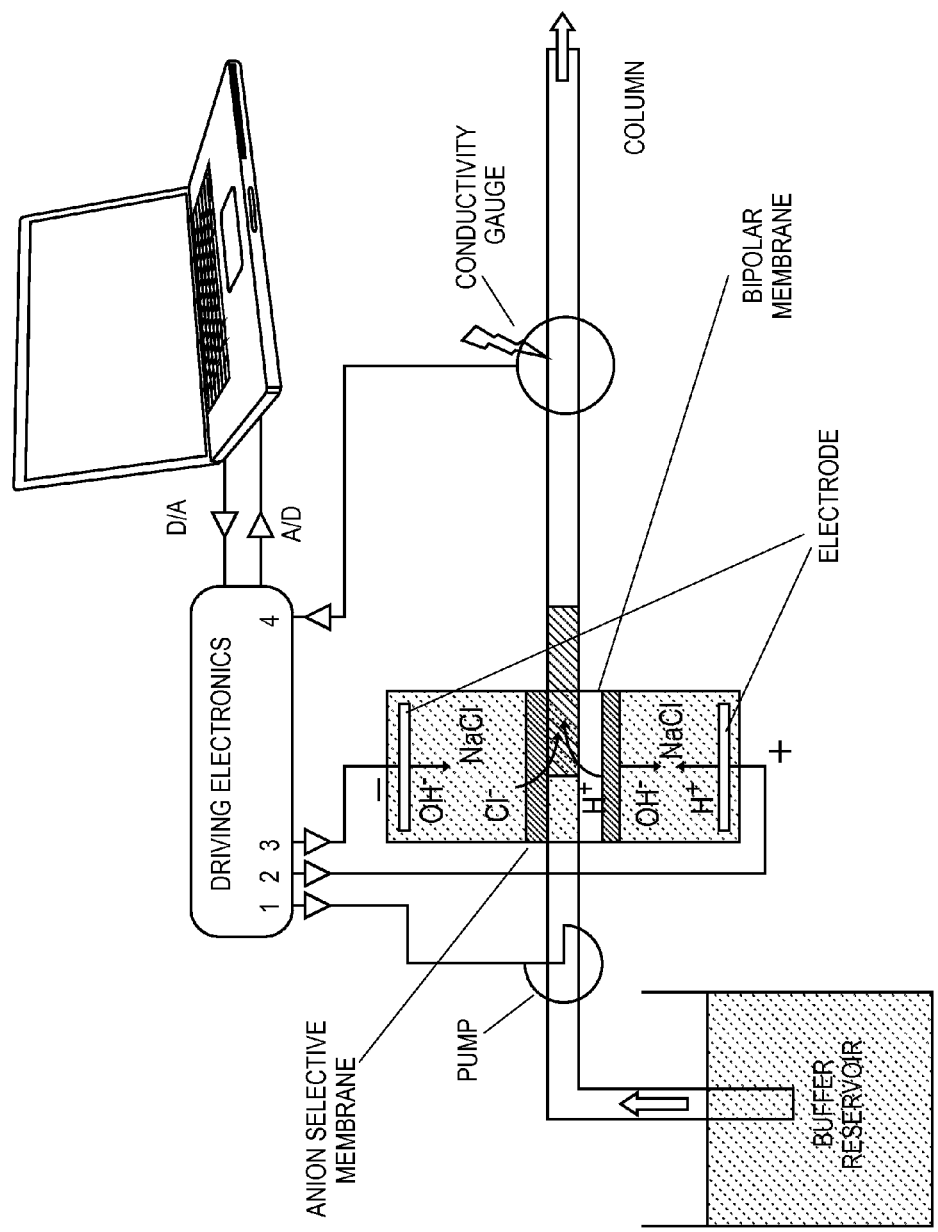
FIG. 2 depicts an apparatus that injects anions (chloride ions depicted) and protons into a vessel. The vessel depicted is a tubing or channel that transfers a solution from a reservoir to a chromatography column destination. However, it will be appreciated that the precise vessel shape can be varied. For example, the side chambers could be placed in contact with a reservoir vessel rather than a channel or tubing as depicted. Similarly, while the Figure depicts a pump and conductivity gauge, the configuration of the two side chambers does not require a pump or conductivity gauge in a particular location, or indeed, at all in some aspects. As noted above, the figures illustrate particular cations and anions (sodium and chloride, respectively). However, for all aspects described herein, it will be appreciated that other ions (e.g., cations including but not limited to, $Li^+$, $K^+$, $Mg^{++}$, $Ca^{++}$, $NH_4^+$, etc., and anions, including but not limited to, $Fl^-$, $Br^-$, $PO_4^-$, etc.) can also be similarly transferred if present.

Injection of a non-proton, non-hydroxide ion from a side chamber into the vessel can be achieved, for example, by pairing a first side chamber comprising a cathode in the side chamber and an anion selective membrane dividing the first side chamber and the vessel with a second side chamber having an anode. In this configuration, the first side chamber will inject anions present in the first side chamber solution in the presence of a current between the cathode and the anode and thus is referred to as an "anion injector." For example, if the side chamber solution comprises chloride anions, the chloride anions will be transferred across the anion selective membrane into the vessel in the presence of a current between the cathode and the anode. An embodiment of this aspect is depicted in FIG. 2, in which the top side chamber in the Figure injects chloride ions in the presence of a current through the top and bottom chamber ("top" and "bottom" as used with reference to figures, refer to the top and bottom of the figure, and not necessarily the top and bottom of the apparatus). However, it should be appreciated that this configuration is not limited to injection of chloride ions. Any anion present and capable of passing through the anion selective membrane can be transferred from the side chamber into the vessel. FIG. 2 further depicts an aspect in which the first side chamber is paired in a circuit with a second side chamber, the second side chamber divided from the vessel by a bipolar membrane. In this aspect, the second chamber injects protons into the vessel and thus is referred to as a "proton injector."

As shown in FIG. 2, application of a voltage between the anode and cathode leads to water splitting by the bipolar membrane (bottom side chamber). Protons are injected into the vessel and titrate the solution flowing in the vessel to the desired reduced pH. Hydroxide ions generated in the splitting process recombine with protons generated by water hydrolysis in the anode. Because the current is the same across the bottom side chamber, the pH in the anode compartment is maintained (in the absence of further electrochemistry) in its initial value. Due to charge neutrality and the anion selective membrane separating the cathode (top as depicted) side chamber from the vessel, anions (e.g., chloride ions) are injected from the cathode (top) side chamber to the vessel. Thus, the solution in the vessel as depicted in FIG. 2 is titrated with HCl.

However, it is also possible for a chamber having an anion selective membrane to inject hydroxide ions into the vessel. This can be achieved, for example, by raising the concentration of hydroxide ions (i.e., raising the pH) in the chamber, thereby allowing for a higher concentration of hydroxide ions to be available to move into the vessel when the current is applied (when the solution in the chamber is neutral, the concentration of hydroxide ions is negligible). An embodiment of this option would be a configuration as shown in FIG. 2, but with the solution in the top chamber being basic.

Figure 3:
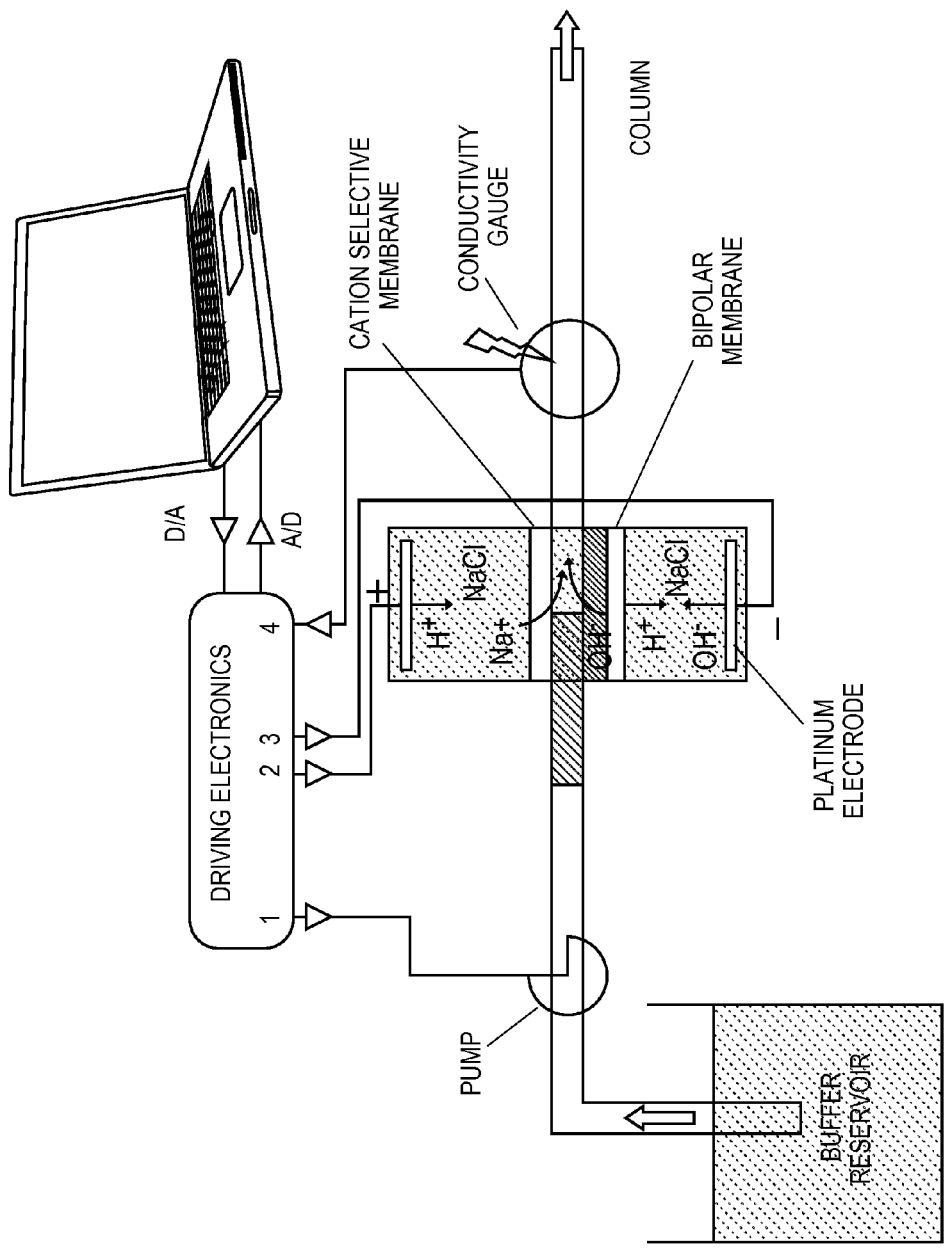
FIG. 3 depicts an apparatus that injects cations (sodium ions depicted) and hydroxide ions into a vessel. The vessel depicted is a tubing that transfers a solution from a reservoir to a chromatography column destination. However, it will be appreciated that the precise vessel shape can be varied. For example, the side chambers could be placed in contact with a reservoir vessel rather than a channel or tubing as depicted. Similarly, while the Figure depicts a pump and conductivity gauge, the configuration of the two side chambers does not require a pump or conductivity gauge in a particular location, or indeed, at all in some aspects.

Alternatively, injection of a non-proton, non-hydroxide ion from a side chamber into the vessel can be achieved, for example, by pairing a first side chamber comprising an anode in the side chamber and a cation selective membrane dividing the first side chamber and the vessel with a second side chamber. In this configuration, the first side chamber will inject cations present in the first side chamber solution into the vessel in the presence of a current between the cathode and the anode and thus is referred to as a "cation injector." For example, if the side chamber solution comprises sodium cations, the sodium cations will be transferred across the cation selective membrane into the vessel. An embodiment of this aspect is depicted in FIG. 3, in which the top side chamber in the Figure injects sodium ions in the presence of a current through the top and bottom chamber. However, it should be appreciated that this configuration is not limited to injection of sodium ions. Any cation present and capable of passing through the cation selective membrane can be transferred from the side chamber into the vessel. FIG. 3 further depicts an aspect in which the first side chamber is paired in a circuit with a second side chamber, the second side chamber divided from the vessel by a bipolar membrane. In this aspect, the second chamber injects hydroxide ions into the vessel and thus is referred to as a "hydroxide ion injector."

In contrast to the aspect depicted in FIG. 2, in FIG. 3 hydroxide ions are injected into the vessel and titrate the solution flowing in the vessel to the desired increased pH. Protons generated in the splitting process recombine with hydroxide ions generated by water hydrolysis in the cathode. Because the current is the same across the bottom side chamber the pH in the cathode side chamber is maintained in its initial value in the absence of other electrochemical processes. Due to charge neutrality and the cation selective membrane separating the anode (top as depicted) side chamber from the vessel, cations (e.g., sodium ions) are injected from the anode (top) side chamber into the vessel. Thus, the solution in the vessel as depicted in FIG. 3 is titrated with NaOH.

However, it is also possible for a chamber having a cation selective membrane to inject hydrogen ions into the vessel. This can be achieved, for example, by raising the concentration of hydrogen ions (i.e., lowering the pH) in the chamber, thereby allowing for a higher concentration of hydrogen ions to be available to move into the vessel when the current is applied (when the solution in the chamber is neutral, the concentration of hydrogen ions is negligible). An embodiment of this option would be a configuration as shown in FIG. 3, but with the solution in the top chamber being acidic.

Figure 5:
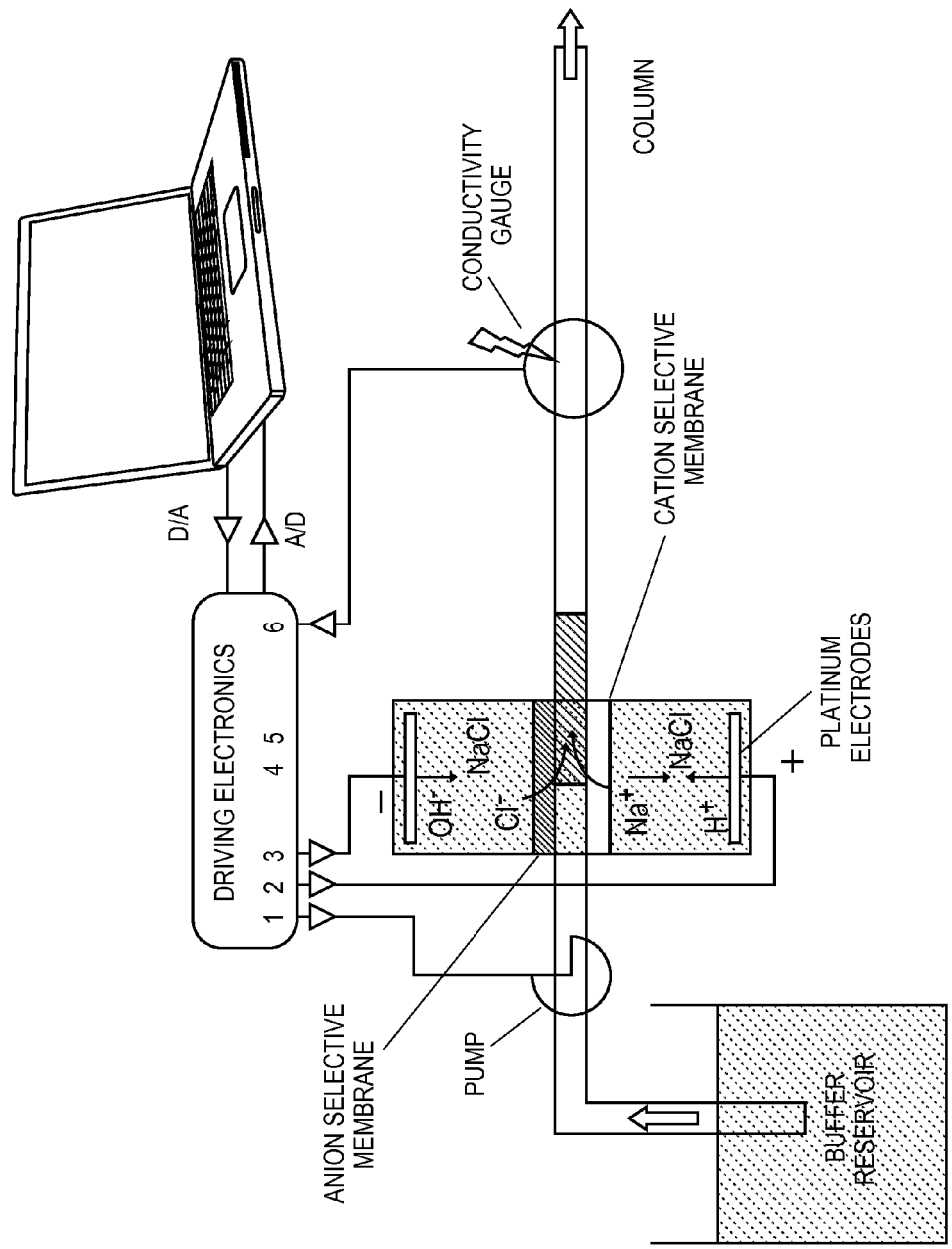
FIG. 5 depicts an apparatus that injects cations (sodium ions depicted) and anions (chloride ions depicted) into a vessel. The vessel depicted is a tubing that transfers a solution from a reservoir to a chromatography column destination. However, it will be appreciated that the precise vessel shape can be varied. For example, the side chambers could be placed in contact with a reservoir vessel rather than a channel or tubing as depicted. Similarly, while the Figure depicts a pump and conductivity gauge, the configuration of the two side chambers does not require a pump or conductivity gauge in a particular location, or indeed, at all in some aspects. In some embodiments, the conductivity of the solution in the vessel is measured by a conductivity gauge connected to terminal 6 and the read value serves to adjust the cation and anion injection currents to yield the desired ion concentrations.

As another alternative, the "first" side chambers in the above two paragraphs (for example, rather than as paired in FIGS. 2-3) can be paired to form a circuit that injects both non-proton cations and non-hydroxide anions into the vessel solution. An example of this aspect is depicted in FIG. 5 (showing chloride and sodium ions). This aspect is useful, for example, for increasing ionic strength or buffering capacity of the vessel solution.

Any number of side chamber circuit pairs can be combined depending on the goal to be achieved. In these embodiments, electrodes in different pairs of side chambers can be controlled independently so that different voltage or current can be applied to different pairs, as desired. Thus, for example, one possible combination of side chambers in fluid contact with a vessel is as follows:

(1) a pair of side chambers that inject anions and protons; and (2) a pair of side chambers that inject cations and hydroxide ions.

Figure 4:
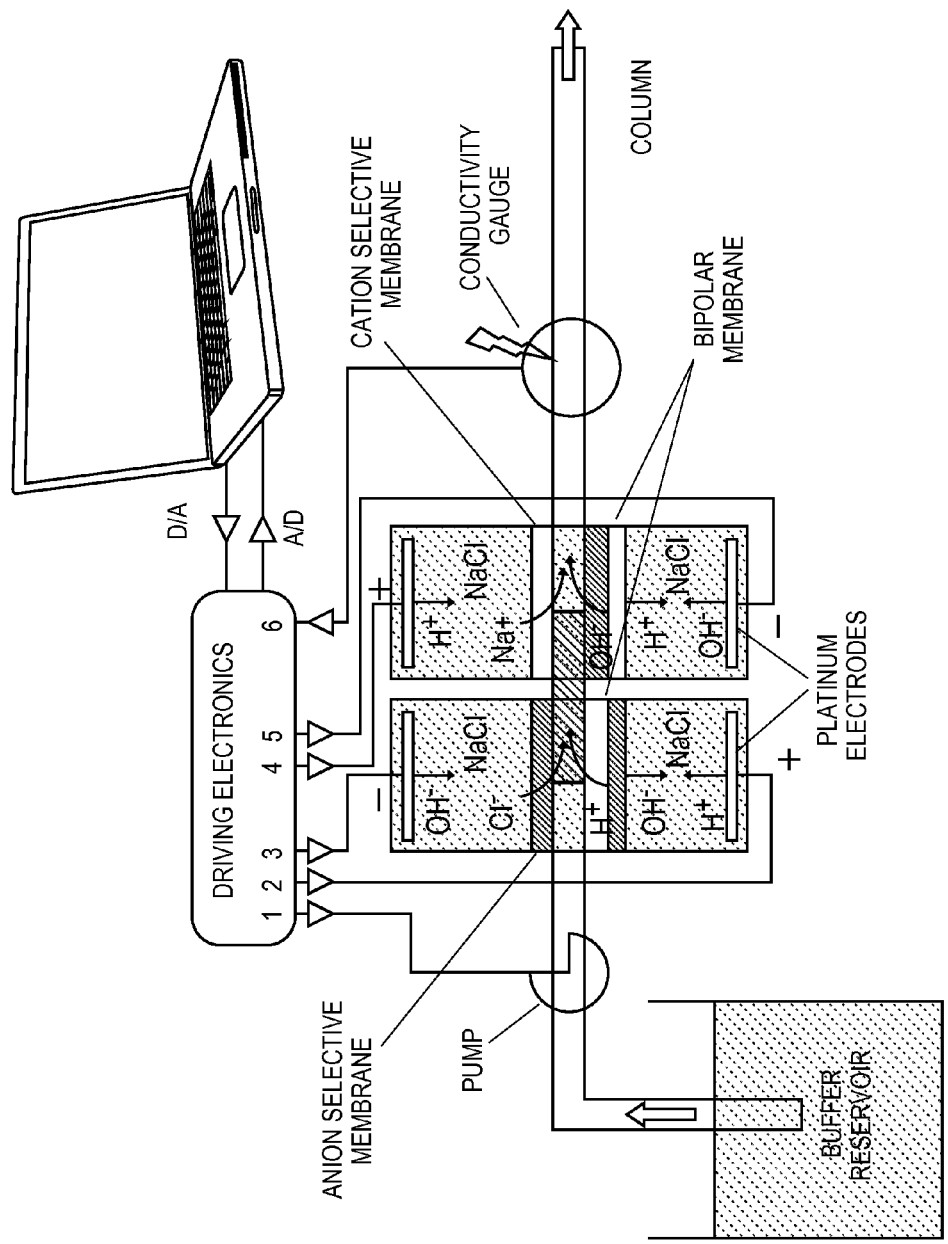
FIG. 4 depicts an apparatus that injects anions (chloride ions depicted) and protons into a vessel with one pair of side chambers and cations (sodium ions depicted) and hydroxide ions into the vessel with a second pair of side chambers. The vessel depicted is a tubing that transfers a solution from a reservoir to a chromatography column destination. However, it will be appreciated that the precise vessel shape can be varied. For example, the side chambers could be placed in contact with a reservoir vessel rather than a channel or tubing as depicted. Similarly, while the Figure depicts a pump and conductivity gauge, the configuration of the two side chambers does not require a pump or conductivity gauge in a particular location, or indeed, at all in some aspects.

An example of the above embodiment is depicted in FIG. 4 (chloride depicted as the anion and sodium depicted as the cation).

Figure 10:
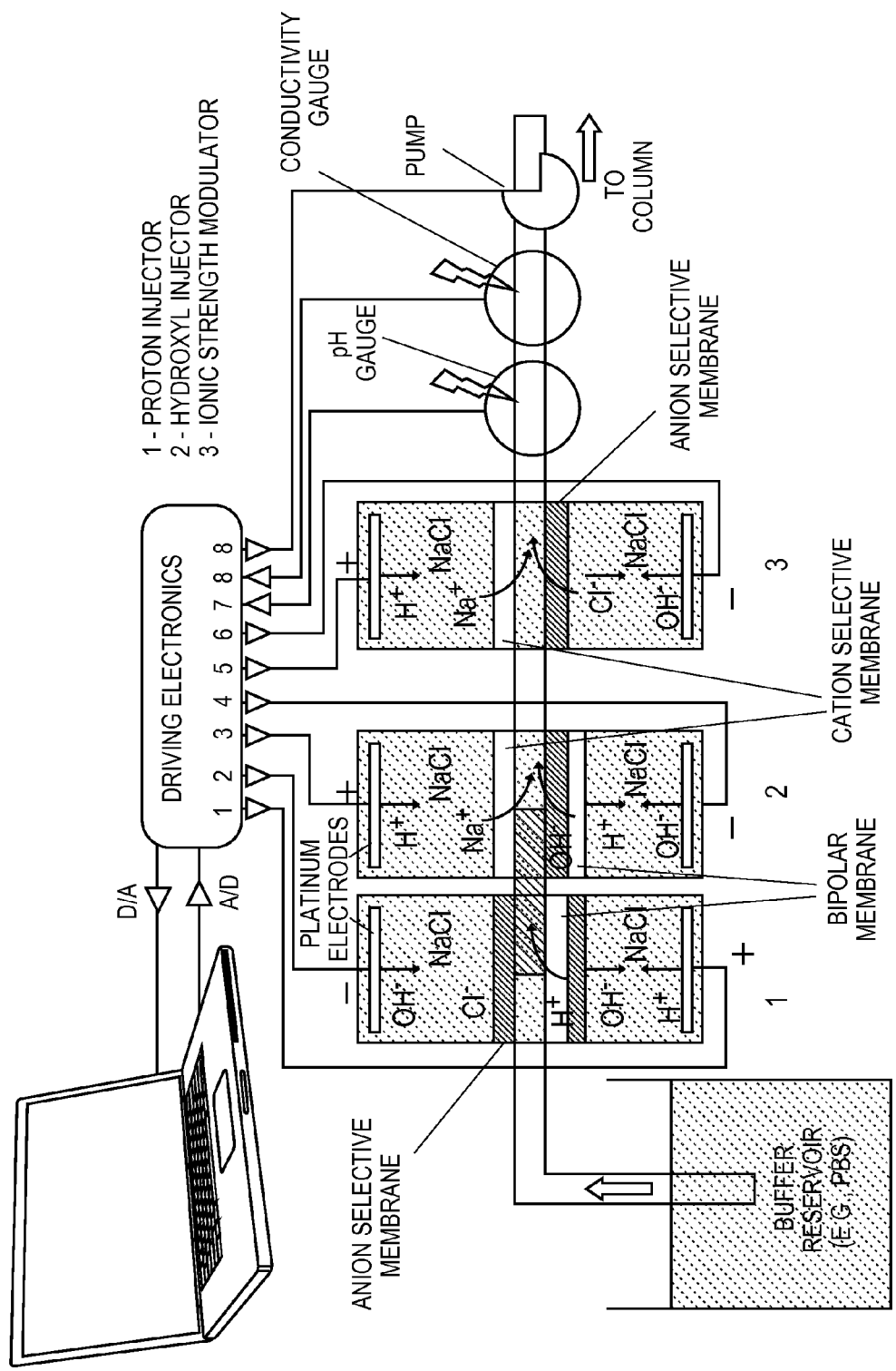
FIG. 10 depicts an apparatus that injects anions (chloride ions depicted) and protons into a vessel with one pair of side chambers and cations (sodium ions depicted) and hydroxide ions into the vessel with a second pair of side chambers and injects cations and anions (sodium and chloride ions, respectively, depicted) into the vessel with a third pair of side chambers. The vessel depicted is a tubing that transfers a solution from a reservoir to a chromatography column destination. However, it will be appreciated that the precise vessel shape can be varied. For example, the side chambers could be placed in contact with a reservoir vessel rather than a channel or tubing as depicted. Similarly, while the Figure depicts a pump, conductivity gauge, and pH gauge, the configuration of the two side chambers does not require a pump or gauge(s) in a particular location, or indeed, at all in some aspects. In some embodiments, the conductivity and pH of the solution in the vessel is measured by conductivity and pH gauges connected to terminals 7,8 and the read values serve to adjust the cation and anion injection currents as well as the proton and hydroxide injection currents to yield the desired ion concentrations and pH value.

In another example of combination of pairs of side channels, FIG. 10 depicts a combination of three pairs of side chambers in fluid contact with a vessel as follows:

(1) a pair of side chambers that inject anions (chloride depicted) and protons;

(2) a pair of side chambers that inject cations (sodium depicted) and hydroxide ions; and (3) a pair of side chambers that inject cations (sodium depicted) and anions (chloride depicted).

This combination allows for increasing the ionic strength of the solution in the vessel (primarily via the third pair of side chambers) while controlling the pH with the first pair of side chambers (decreasing pH and marginally increasing ionic strength) and the second pair of side chambers (increasing pH and marginally increasing ionic strength). The injectors can be operated in various ways to manipulate only pH, ionic strength or both. If each injector is turned on one at a time the pH will be decreased or increased. If both are turned on at the same time with equal current, the ionic strength will change but not pH. If one is operating with higher current than the other than pH and ionic strength will change at the same time. It is also possible to bias two or more cation injectors relative to a single anion injector thus injecting simultaneously two different cations and a single anion into the vessel. Or alternatively, to bias two or more anion injectors relative to a single cation injector thus injecting simultaneously two different anions and a single cation into the vessel. Any combination of two or more injectors can be used this way. It is also possible to use a single ion injector or more with the other electrode connected to the vessel.

B. Ion Extractors

Also provided are combinations of side chambers that transfer ions from the solution in the vessel into the side chambers (i.e., acting as ion extractors).

Figure 6:
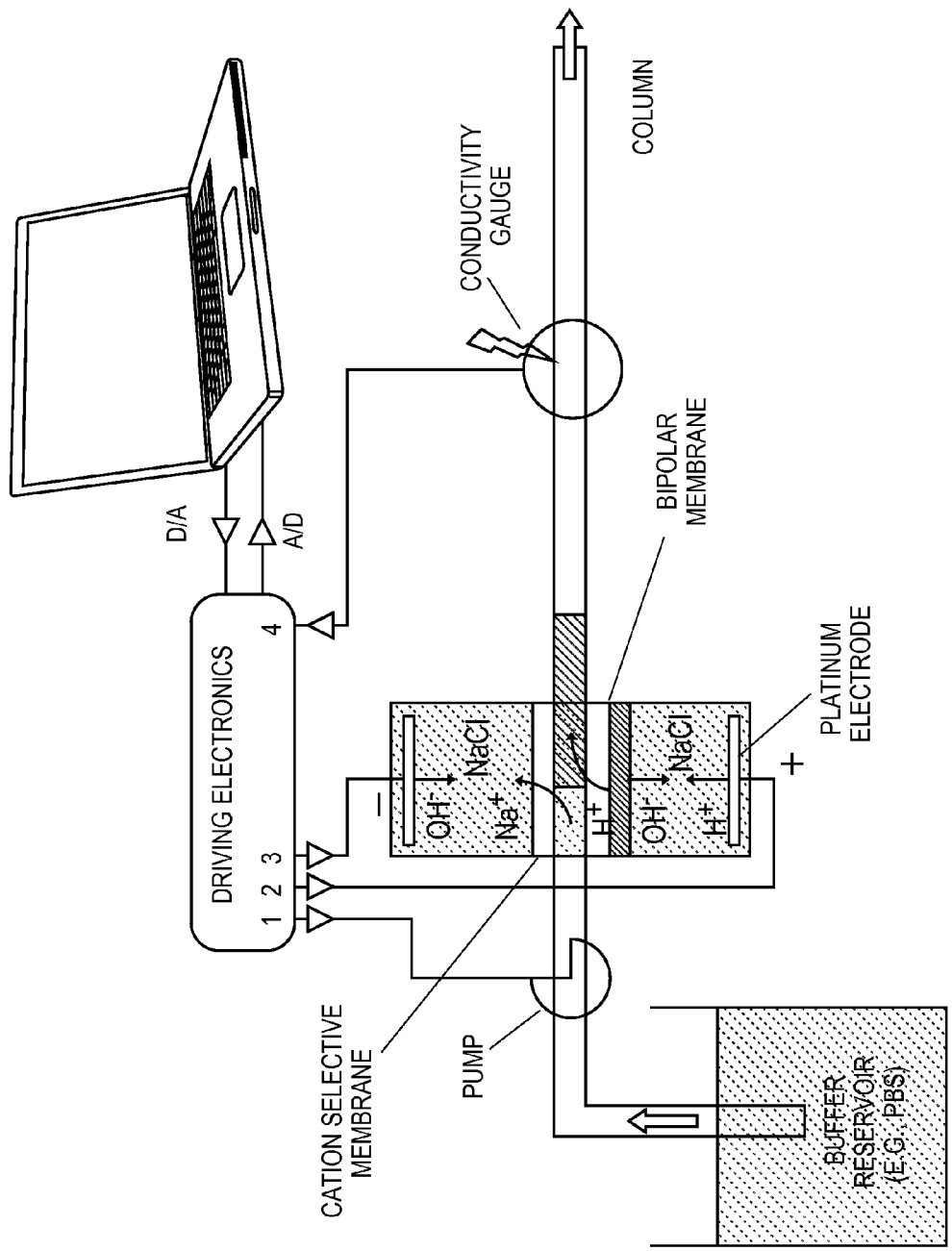
FIG. 6 depicts an apparatus that injects protons into a vessel while extracting cations (sodium ions depicted) from the vessel. The vessel depicted is a tubing that transfers a solution from a reservoir to a chromatography column destination. However, it will be appreciated that the precise vessel shape can be varied. For example, the side chambers could be placed in contact with a reservoir vessel rather than a channel or tubing as depicted. Similarly, while the Figure depicts a pump and conductivity gauge, the configuration of the two side chambers does not require a pump or conductivity gauge in a particular location, or indeed, at all in some aspects.

In some aspects, a pair of side chambers extract a non-proton, non-hydroxide ion from the vessel into a side chamber while adding a proton or hydroxide ion into the vessel from a different side chamber. This can be achieved, for example, by pairing a first side chamber comprising a cathode in the side chamber and a cation selective membrane dividing the first side chamber and the vessel with a second side chamber having an anode. In this configuration, the first side chamber will extract cations present in the vessel and transfer the cations into the first side chamber and thus is referred to as a "cation extractor." For example, if the vessel solution comprises sodium ions, the sodium ions will be transferred across the cation selective membrane from the vessel in the presence of a current between the cathode and the anode. An embodiment of this aspect is depicted in FIG. 6, in which the top side chamber in the Figure extracts cations (sodium ions depicted) from the vessel in the presence of a current through the top and bottom chamber. However, it should be appreciated that this configuration is not limited to extraction of sodium ions. Any cation present and capable of passing through the cation selective membrane can be transferred from the vessel into the side chamber. FIG. 6 further depicts an aspect in which the first side chamber is paired in a circuit with a second side chamber, the second side chamber divided from the vessel by a bipolar membrane. In this aspect, the second chamber injects protons into the vessel while the first chamber extracts sodium cations.

Figure 7:
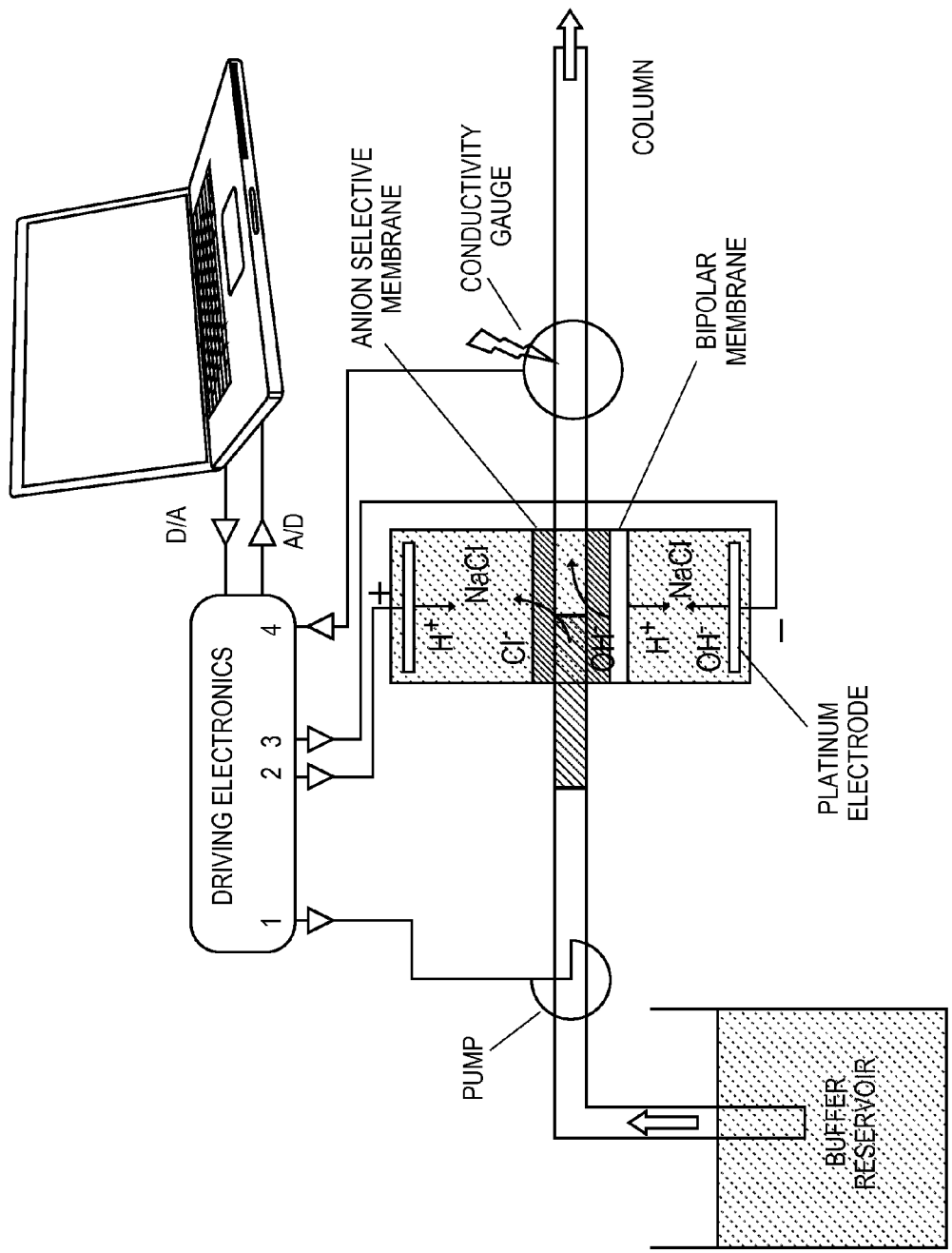
FIG. 7 depicts an apparatus that injects hydroxide ions into a vessel while extracting anions (chloride ions depicted) from the vessel. The vessel depicted is a tubing that transfers a solution from a reservoir to a chromatography column destination. However, it will be appreciated that the precise vessel shape can be varied. For example, the side chambers could be placed in contact with a reservoir vessel rather than a channel or tubing as depicted. Similarly, while the Figure depicts a pump and conductivity gauge, the configuration of the two side chambers does not require a pump or conductivity gauge in a particular location, or indeed, at all in some aspects.

Alternatively, extraction of a non-proton, non-hydroxide ion from the vessel into a side chamber while adding a proton or hydroxide ion into the vessel from a different side chamber can be achieved, for example, by pairing a first side chamber comprising an anode in the side chamber and an anion selective membrane dividing the first side chamber and the vessel with a second side chamber. In this configuration, the first side chamber will extract anions present in the vessel and transfer the anions into the first side chamber and thus is referred to as an "anion extractor." For example, if the vessel solution comprises chloride ions, the chloride ions will be transferred across the anion selective membrane out of the vessel in the presence of a current between the cathode and the anode. An embodiment of this aspect is depicted in FIG. 7, in which the top side chamber in the Figure extracts anions (chloride ions depicted) from the vessel in the presence of a current through the top and bottom chamber. However, it should be appreciated that this configuration is not limited to extraction of chloride ions. Any anion present and capable of passing through the anion selective membrane can be transferred from the vessel into the side chamber. FIG. 7 further depicts an aspect in which the first side chamber is paired in a circuit with a second side chamber, the second side chamber divided from the vessel by a bipolar membrane. In this aspect, the second chamber injects hydroxide ions into the vessel.

Figure 9:
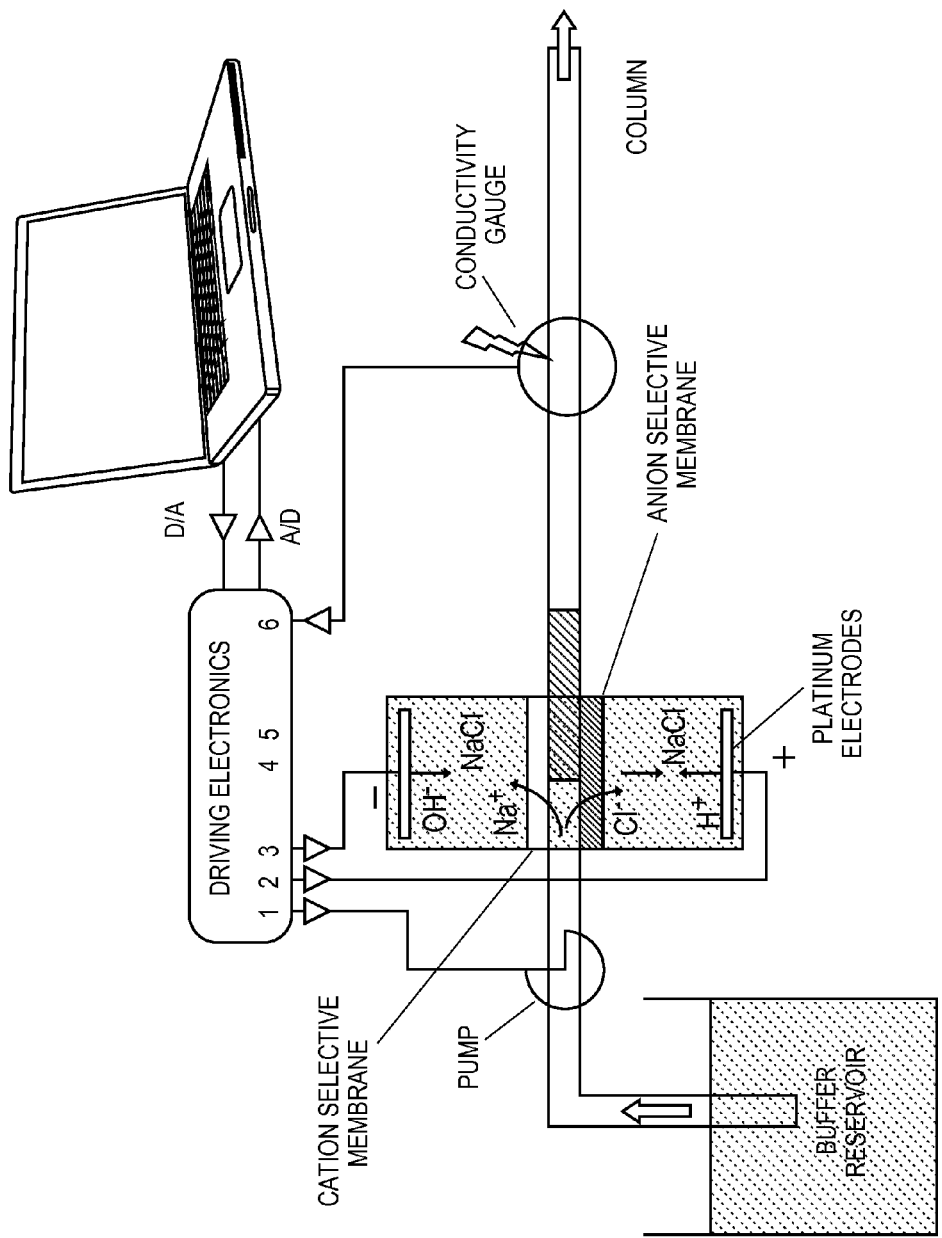
FIG. 9 depicts an apparatus that extracts cations (sodium ions depicted) and anions (chloride ions depicted) from the vessel. The vessel depicted is a tubing that transfers a solution from a reservoir to a chromatography column destination. However, it will be appreciated that the precise vessel shape can be varied. For example, the side chambers could be places in contact with a reservoir vessel rather than a channel or tubing as depicted. Similarly, while the Figure depicts a pump and conductivity gauge, the configuration of the two side chambers does not require a pump or conductivity gauge in a particular location, or indeed, at all in some aspects. In some embodiments, the conductivity of the solution in the vessel is measured by a conductivity gauge connected to terminal 6 and the read value serves to adjust the cation and anion injection currents to yield the desired ion concentrations.

Alternatively, the "first" side chambers in the above two paragraphs can be combined to form a circuit that extracts both anions and cations from the vessel solution. An example of this aspect is depicted in FIG. 9 (chloride and sodium ions depicted). This aspect is useful, for example, for decreasing ionic strength of the vessel solution.

Side chamber circuit pairs that extract ions from the vessel can also be combined with each other or with the injectors listed above. Thus, for example, one possible combination of side chambers in fluid contact with a vessel is as follows:

(1) a pair of side chambers that extract cations from the vessel and inject protons into the vessel; and (2) a pair of side chambers that extract anions from the vessel and inject hydroxide ions into the vessel.

(3) a pair of side chambers that extract one type of anions from the vessel and inject another type of anions into the vessel (anion exchange)

Figure 8:
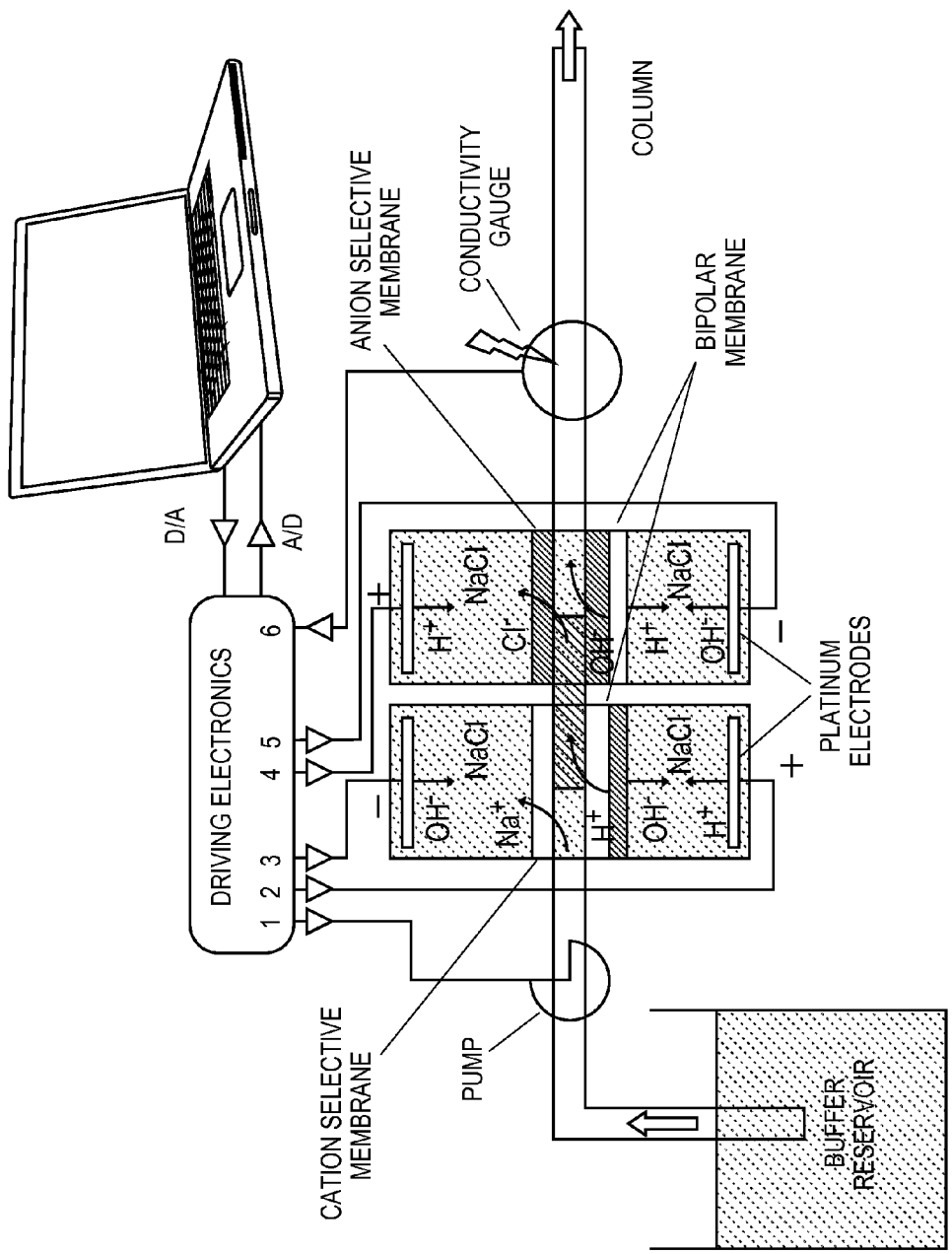
FIG. 8 depicts an apparatus that injects protons into a vessel while extracting cations (sodium ions depicted) from the vessel with one pair of side chambers and injects hydroxide ions into a vessel while extracting anions (chloride ions depicted) from the vessel with a second pair of side chambers. The vessel depicted is a tubing that transfers a solution from a reservoir to a chromatography column destination. However, it will be appreciated that the precise vessel shape can be varied. For example, the side chambers could be placed in contact with a reservoir vessel rather than a channel or tubing as depicted. In some embodiments, the pH of the solution in the vessel is measured by a pH gauge connected to terminal 6 and the read value serves to adjust the proton and/or hydroxide injection currents to yield the desired pH value. While the Figure depicts a pump and pH gauge, the configuration of the two side chambers does not require a pump or pH gauge in a particular location, or indeed, at all in some aspects.

An example of the above embodiment is depicted in FIG. 8 (chloride depicted as the anion and sodium depicted as the cation).

Additional embodiments can include configurations in which one, two, or more types of ions are extracted from the vessel using one or more pair of side chambers while a separate pair (or more) of side channels is used to inject one, two, or more other types of ions into the vessel. For example, in some embodiments, chloride and sodium are extracted from the vessel using in a first pair of side chambers and sulfate and sodium are injected into the vessel using a second pair of side chambers.

B. Solutions

Any type of solution that can support an electrical current can be used with the invention. The solution will generally comprise one or more ions, one or more buffers, and can optionally include a biological product or sample. For example, in some embodiments, the solution will comprise one or more cell or biomolecule (e.g., protein, nucleic acid, or other product from a cell).

Figure 31:
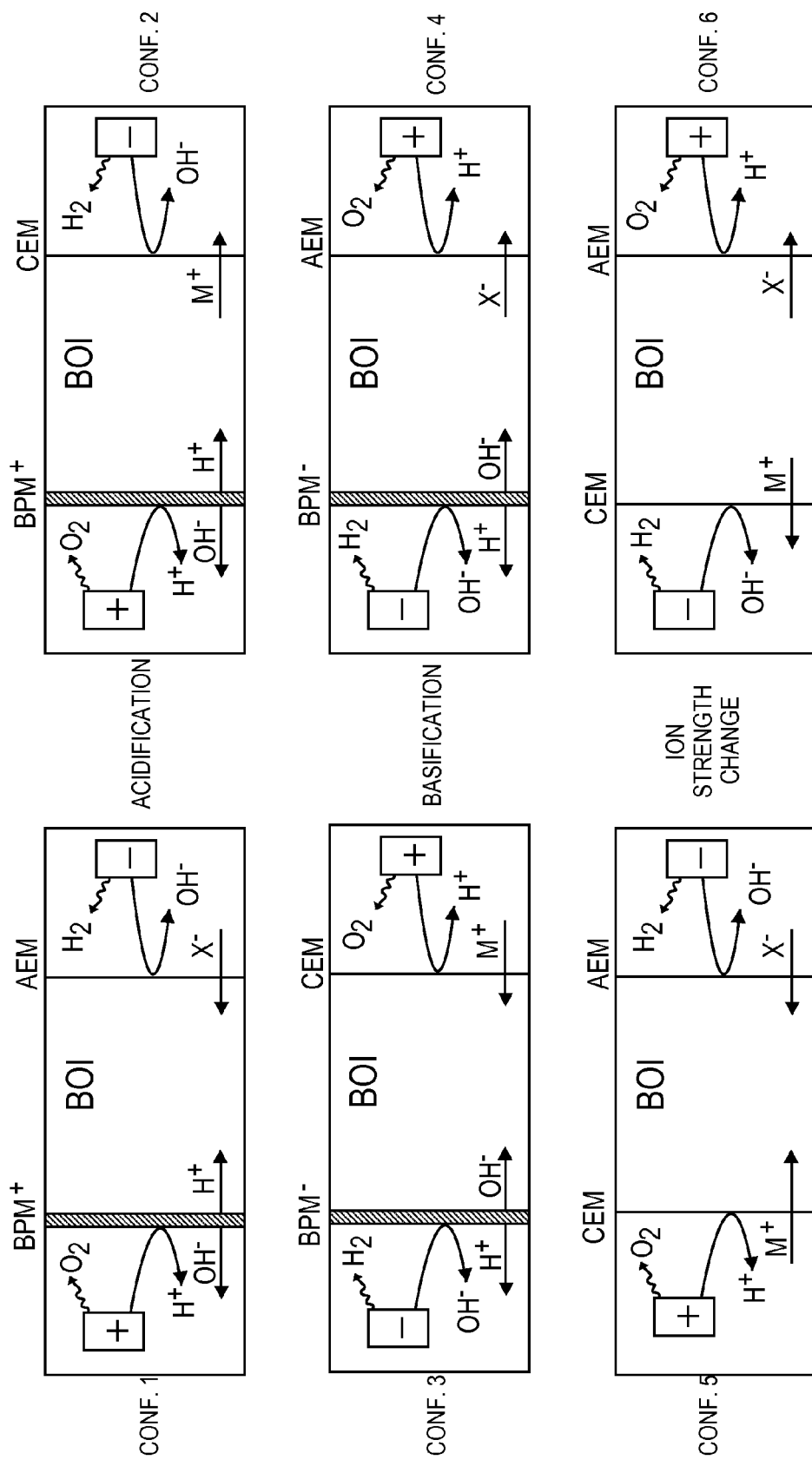
FIG. 31 illustrates a variety of tuner configurations.

Selection of a preferred buffer will depend on the configuration of pH/ionic strength tuner used. A variety of tuner configurations are depicted in FIG. 31 (with configuration numbers on the left sides of the various configurations). The table below illustrates some possible configuration/buffer combinations.

contains $Cl^-$, TEA/HCl 1M buffer can be used in the AEM donors (configuration 1, 5). For configuration 3 and 5 (CEM donor) the cation component of the buffer can be introduced from donor to the BOI, i.e. phosphate buffer can be used, while the cation component of the donor buffer can be the same as the composition of the BOI. For example, if the desired buffer contains $Na^+$, $Na_2HPO_4/NaH_2PO_4$ (e.g., 1 M) buffer can be used in the CEM donors (configuration 3, 5).

In some embodiments, the solution is treated by the side chambers to remove or add ions and optionally to adjust the pH so that the sample is appropriate to add directly to a chromatographic or analytical device. Examples of chromatographic devices include chromatography columns, include, but not limited to ion exchange columns. Exemplary analytical devices include, but are not limited to a mass spectrometer or a capillary electrophoresis. In some embodiments, the apparatus is adapted to apply the sample, after the ions and/or pH is adjusted, to a chromatographic or analytical device.

III. Methods

One can adjust the pH or ionic strength of a solution in a vessel as desired using an apparatus as described above. The particular configuration selected will depend on the goal to be achieved (e.g., increase ionic strength only, adjust pH and ionic strength, exchange ions, etc.) as well the desired simplicity and cost of the device, etc. As noted above, by controlling the relative and absolute level of current of the various side chamber pairs, one can achieve a desired pH and/or ionic strength. If desired, a pH and/or conductivity gauge can be placed in the apparatus to measure the pH or ionic strength of the solution and that information can be fed back to an electronic controller to adjust the pH or ionic strength. In some embodiments, the pH gauge is an absolute pH electrode. Examples of absolute pH electrodes are described in, e.g., PCT WO/2005085825 and are commercially available from e.g., a Senova. Alternatively, adjustment of current in each side chamber pair can be performed manually.

| Configuration | 1 | 3 | 5 | 2, 4, 6 |
|---|---|---|---|---|
| BPM donor | Phosphate buffer (e.g., 1M at pH 7.0) | Phosphate buffer (e.g., 1M at pH 7.0) | Phosphate buffer (e.g., 1M) containing the relevant cation | 1M phosphate buffer pH 7.0 |
| Ion exchange donor | Amine based buffer (e.g., 1M) acidified with appropriate acid | Phosphate buffer (e.g., 1M) containing the relevant cation | Amine based buffer (e.g., 1M) acidified with appropriate acid | 1M phosphate buffer pH 7.0 |

In some embodiments, donor solutions (i.e., a solution in a side chamber to donate protons, hydroxide ions, or other ions, are filled with high capacity buffers (e.g., 1 M) to prevent leakage of ions through membranes. The type of buffer filled in the bipolar membrane (BPM) donor side chamber is not particularly important because no ions except H+ and OH− pass the membrane (for configurations 1-4). Similarly, in configurations 2, 4 and 6 ions are depleted from the buffer of interest (BOI) to the donor cells via ion selective membranes (ISM), and therefore the buffer type filled in those donors is not particularly important. However, in configurations 1, 3, 5 selection of a buffer can affect performance. For configurations 1 and 5, anions are pumped from AEM donor side chambers to the BOI, therefore ideally the anionic component of the donor buffer is the same as the composition of the BOI. For example: if the desired buffer In some aspects, the vessel of the apparatus is connected to a chromatography support. In many types of chromatography, adjustment of pH or ionic strength can result in differential binding or elution of target molecules, or contaminants, from a sample. The methods therefore allow for generation of concentration and/or pH gradients without mixing, for example, starting point and end point solutions as has historically been used to generate gradients. By the same token they can also be used to adjust the type and concentration of ions, as well as pH value following chromatographic separation.

In some embodiments, the chromatography is ion exchange chromatography (e.g., anion exchange, cation exchange, or mixed mode). In some embodiments, the chromatography is affinity chromatography. In some embodiments, the chromatography is displacement chromatography. Thus, in some methods described herein, the cations and/or anions include cations and/or anions used in displacement chromatography, including but not limited to imidazole as a cation and glutathione as an anion.

It will be appreciated that the apparatuses and methods described herein are not limited to uses with chromatography and can be applied to any system or use for which the ionic strength and/or pH of a solution is to be adjusted. For instance, the ion type, concentration, and pH can be adjusted in preparation for mass spectroscopy analysis.

As discussed above, the methods can be used to adjust pH or ion concentration of a sample (e.g., a cell or macromolecule (e.g., protein or nucleic acid sample), optionally retained in a molecular weight cut-off membrane. The method can be used to desalt samples comprising macromolecules, e.g., proteins, DNA, RNA, oligonucleotides, peptides, etc. In some embodiments, charged molecules smaller than the cutoff of the pores in the dialysis membrane are removed, or at least reduced in concentration. The method can also be used, for example, for cleanup of proteins and/or DNA from smaller fragments of proteins/peptides and DNA (e.g., oligonucleotides) by selecting a molecular cutoff membrane having a sufficiently large cutoff to allow peptides and/or oligonucleotides to pass through the membrane(s) but blocking movement of the larger proteins and/or DNA.

Moreover, by reversing the polarity of the voltage, namely turning the anode into cathode and vice versa it is possible to enhance the salt concentration in the macromolecule sample. Other configurations are also possible. One can for instance use two anionic or two cationic membranes to exchange one type of anions with another type (the case of two anionic membranes) or exchange one type of cations with different cations. One can also introduce, remove, or exchange buffer. The same device can also be used to concentrate or dilute a macromolecule or cell sample. To concentrate the sample, ions are injected into the vessel. As a result of the ion concentration increase water will diffuse through the dialysis membrane into the chamber, thus concentrating the molecules in the dialysis bag. Conversely, removal of ions from the vessel will lead to water flow into the dialysis bag.

In some embodiments, one or more ion injector (e.g., a proton injector and/or a hydroxide injector) is applied to alter an enzymatic or chemical reaction by controlling the pH and/or ionic strength of a reaction mixture. The majority of the chemical and biochemical (enzyme) reactions are pH dependent. The pH during the reaction is normally controlled by using buffers. However there are situations when the reaction conditions are desired to be controlled so the reaction proceeds at certain speed, or starts or stops at specific time or point of the reaction, or is modified in some pattern in time, or so that the pH does not drift during a reaction. In such situations pH control using a proton injector or hydroxide injector can be applied to increase or decrease the activity of the enzyme or to completely stop or pause the reaction. An example of an enzymatic reaction useful for the methods, include but is not limited to, a template-dependent nucleotide incorporation reaction, e.g., using a DNA or RNA polymerase. Similarly, the pH can also be used to start, stop or change the rate of chemical reactions. This can be accomplished by using the bipolar membrane system to inject protons or hydroxide ions as needed to increase or decrease the pH. It can also be used to maintain optimal reaction conditions in reactions that lead to pH change. See, e.g., FIGS. 23 and 24.

Figure 23:
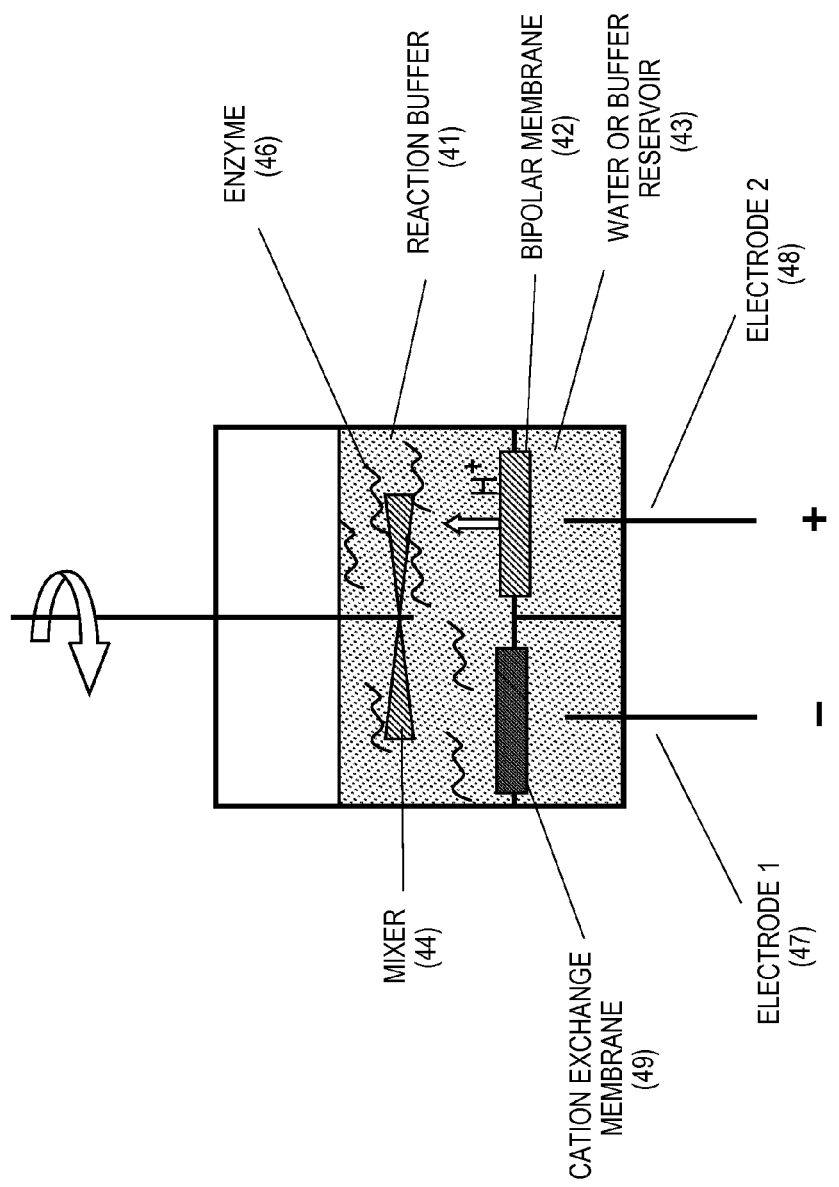
FIG. 23 illustrates an embodiment for controlling pH of a chemical or enzymatic reaction with a proton injector.
Figure 24:
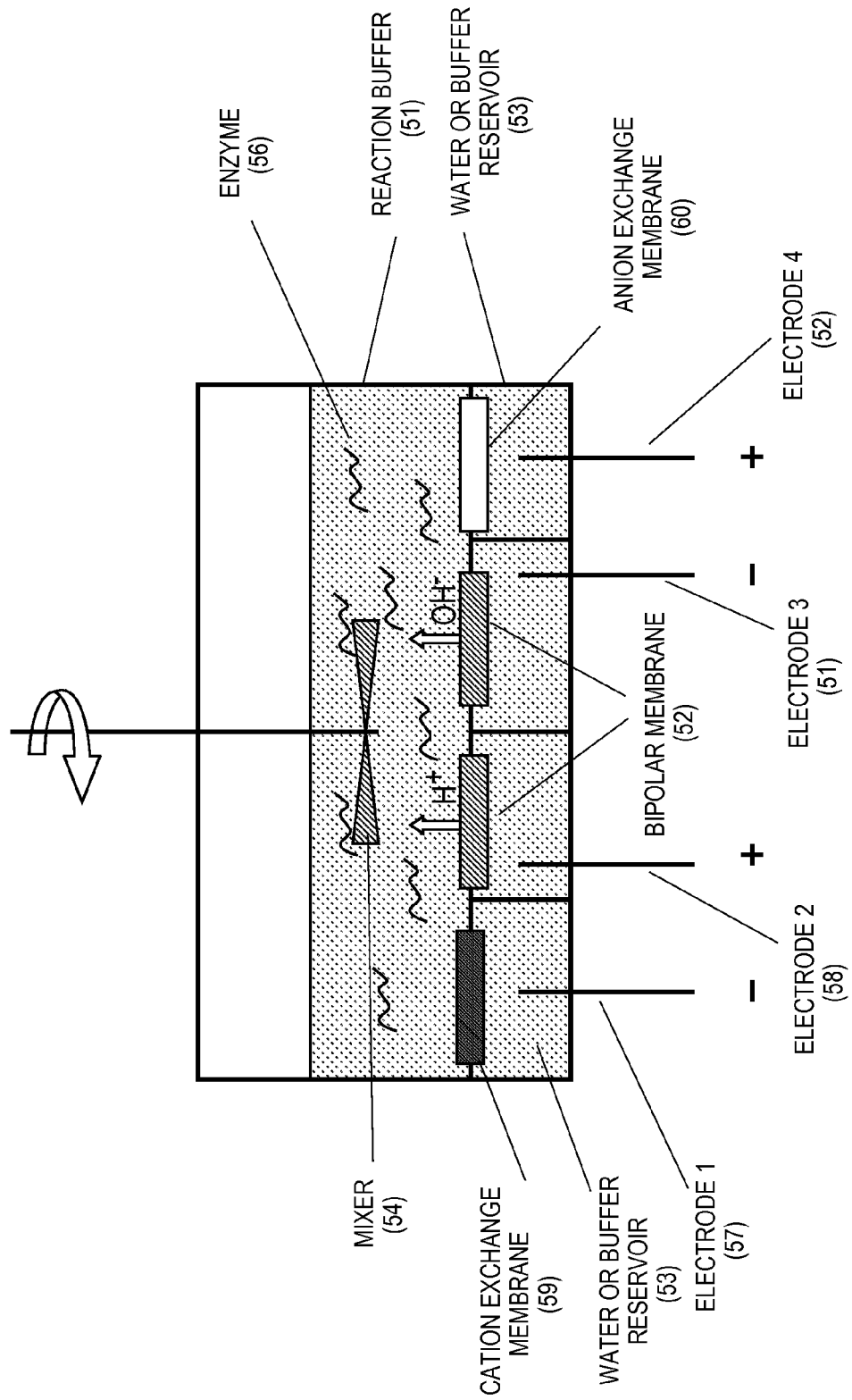
FIG. 24 illustrates an embodiment for controlling pH of a chemical or enzymatic reaction with a proton injector and a hydroxide ion injector.

Referring to FIG. 23, the pH of the reaction buffer (41) can be adjusted by using the bipolar membrane (42) to split the water or buffer (43) and selectively inject protons. In some embodiments, the system may also have mixer (44) or create circulation using a pump, in order to ensure uniformity of the pH across the whole reaction vessel. In some embodiments, a proton injector and a hydroxide ion injector can be used to control the pH of the solution. An embodiment comprising both types of injectors is shown in FIG. 24.

In some embodiments, two or more components can be present in the chamber and their binding to each other can be controlled and monitored while or after the pH in the chamber is changed. Exemplary components include, but are not limited to, one or more affinity agent and a target molecule. Exemplary affinity agents include, e.g., an antibody, antibody fragment, or aptamer. For example, the affinity agent(s) can be labeled and used in the format of an immunoassay to detect the presence or absence of a target molecule.

For a review of immunological and immunoassay procedures, see *Basic and Clinical Immunology* (Stites & Terr eds., 7th ed. 1991). Immunoassays can be performed in any of several configurations, which are reviewed extensively in *Enzyme Immunoassay* (Maggio, ed., 1980); and Harlow & Lane, supra).

Immunoassays also often use a labeling agent to specifically bind to and label the complex formed by the antibody and target molecule(s). The labeling agent may itself be one of the moieties comprising the antibody/antigen complex. Thus, the labeling agent may be a labeled polypeptide or a labeled (e.g., biotinylated) antibody that binds the target of interest. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135: 2589-2542 (1985)). The labeling agent can be modified with a detectable moiety, such as biotin, to which another molecule can specifically bind, such as avidin or streptavidin. A variety of detectable moieties are well known to those skilled in the art.

Immunoassays include noncompetitive assays and competitive assays. In competitive assays, the amount of polypeptide present in the sample is measured indirectly by measuring the amount of a known, added (exogenous) polypeptide of interest displaced (competed away) from an antibody that binds by the unknown polypeptide present in a sample.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes (e.g., fluorescein isothiocyanate, Texas red, rhodamine, and the like), radiolabels, enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component (e.g., the primary detection antibody) of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize the polypeptide of interest, or secondary antibodies that recognize an antibody that binds the polypeptide.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Methods of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

In some embodiments, two or more components can be present in the chamber and their binding to each other can be controlled and monitored while or after the pH or ionic strength in the chamber is changed. In some embodiments, binding of one or more nucleic acid components is controlled and monitored while or after the pH or ionic strength in the chamber is changed. Exemplary nucleic acids include, e.g., DNA and RNA, though nucleic acid mimetics may also be used. In some embodiments, at least one of the nucleic acids is a nucleic acid probe or primer. An "olignucleotide primer" or "primer" refers to an oligonucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides in length. In some embodiments, the components are complementary nucleic acids.

Methods and devices for chromatographic separation using a ion injectors as described herein are provided. In chromatography separations such as ion exchange and affinity chromatography, analytes are frequently eluted by utilizing a pH and/or ionic strength gradient. The change in pH leads to changes in the charge of the molecules or their native state therefore changing the interaction with the matrix. In traditional chromatography systems, gradients are created by mixing at least two pre-made solutions (two buffers with different pH or a buffer and an acid or a base). Besides the need for preparing at least two different solutions, these type of systems need to have either two pumps or a valve and a mixer.

In contrast, the methods and devices described here provide for a separation buffer that is pumped by the pump, or otherwise moved, through the vessel to the chromatography support. Ions are injected into the buffer therefore changing the pH of the buffer flowing through the chromatography support or other binding media, chromatographic support/material, etc. The rate of injection of the ions (e.g., protons, hydroxides or other ions) can be regulated by the voltage potential applied to the bipolar membranes and therefore creating a change in pH and/or ionic strength. The proton, hydroxide, or ion injection system may be positioned before or after the pump used to transport the buffer. The buffer may be transported using variety of ways such as for example but not limited to a pump, pressure, vacuum, gravity or others. The device can be configured for direct or indirect attachment to a chromatographic material container, including but not limited to a chromatographic column, thereby allowing the buffer in the chamber/channel to be moved continuously to the chromatography material, allowing for step or gradient changes to the pH, e.g., for elution or washing during chromatography.

Depending on the need the pH of the buffer can be decreased by injecting protons or increased by injecting hydroxide ions. In some embodiments, two bipolar membranes can be used (one to increase and one to decrease the pH when needed). The bipolar membrane can have different configurations, such as a tubing, a coil or other shape in order to increase the surface area and therefore the capacity of the system to generate ions. This approach allows for simplified design of a chromatography system allowing to make pH gradient capable system that is much simpler and cheaper, while at the same time allowing the system to have pH gradient capabilities. The system may also be implemented as a batch purification where the chromatography media is in a container (not a column) and the molecules of interest are added, allowing for binding to take place, and then eluted, for example, with a change of the pH.

The binding media can be a chromatography or affinity media that can be implemented in variety of ways such as for example but not limited to chromatography beads, magnetic beads, cross-linked polymer beads, a membrane, a linear polymer with suitable interaction groups bound to the polymer and others.

In other embodiments, the apparatus can be used for, e.g., selective precipitation of proteins or chromatography conditions testing (in either case, by changing pH and/or ionic strength) or DNA or protein denaturation (e.g., instead of raising the temperature of the solution).

EXAMPLES

The following examples are offered to illustrate, but not to limit the claimed invention.

Example 1

Figure 14:
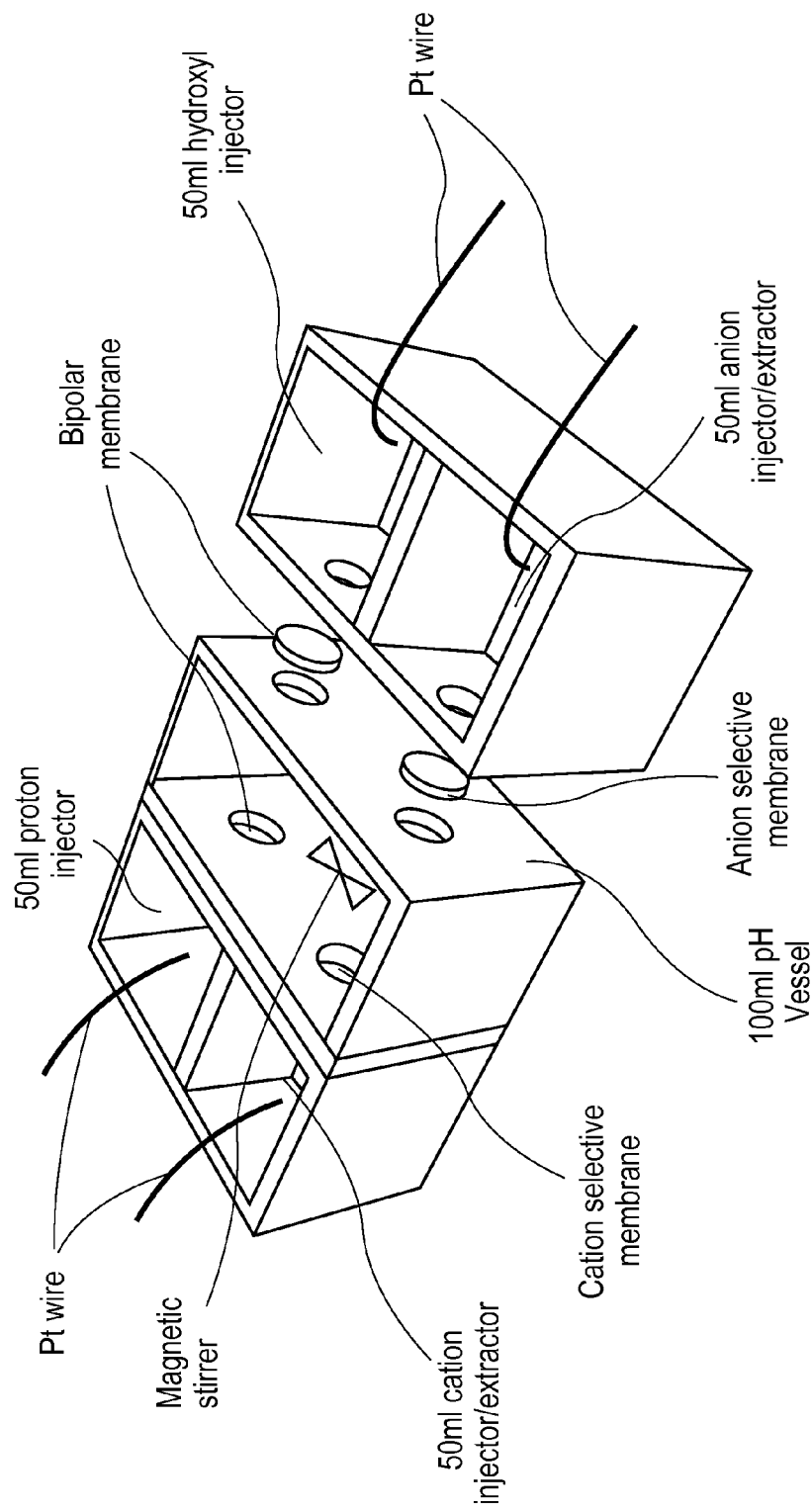
FIG. 14 illustrates an apparatus configuration for modifying pH or ion concentration in a vessel.
Figure 15:
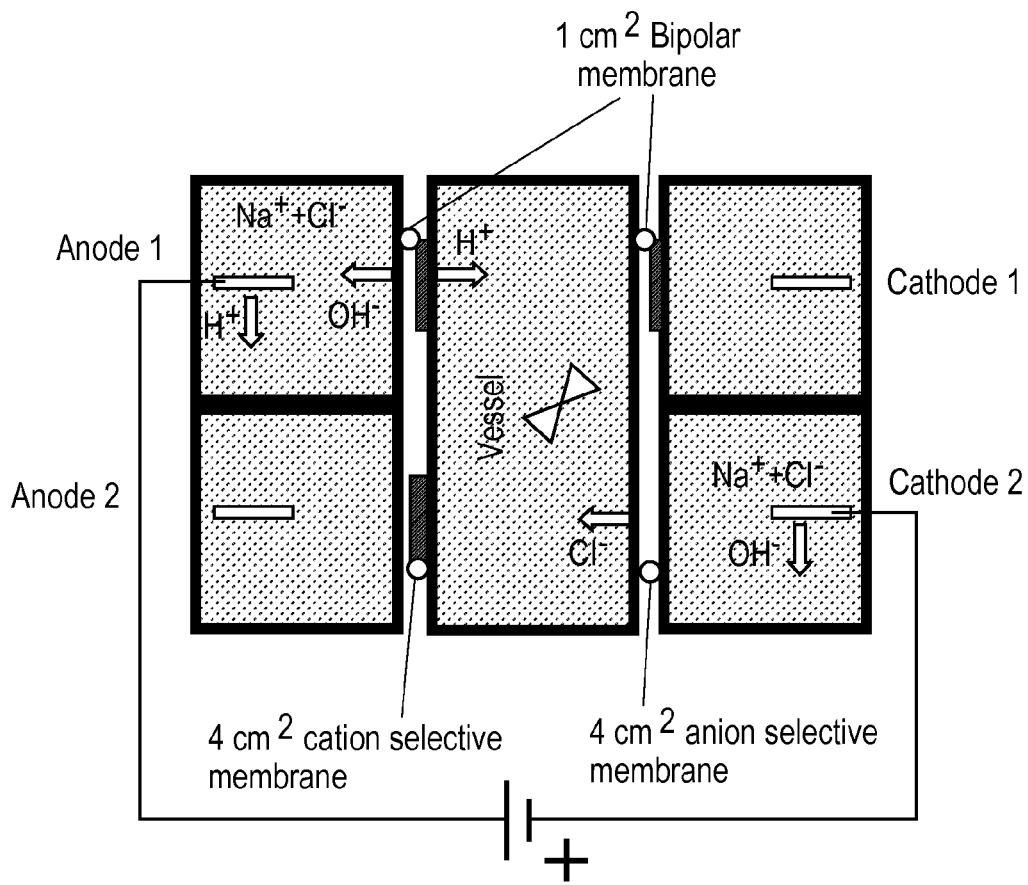
FIG. 15 illustrates an apparatus configuration for titrating a solution in the vessel with HCl.
Figure 16:
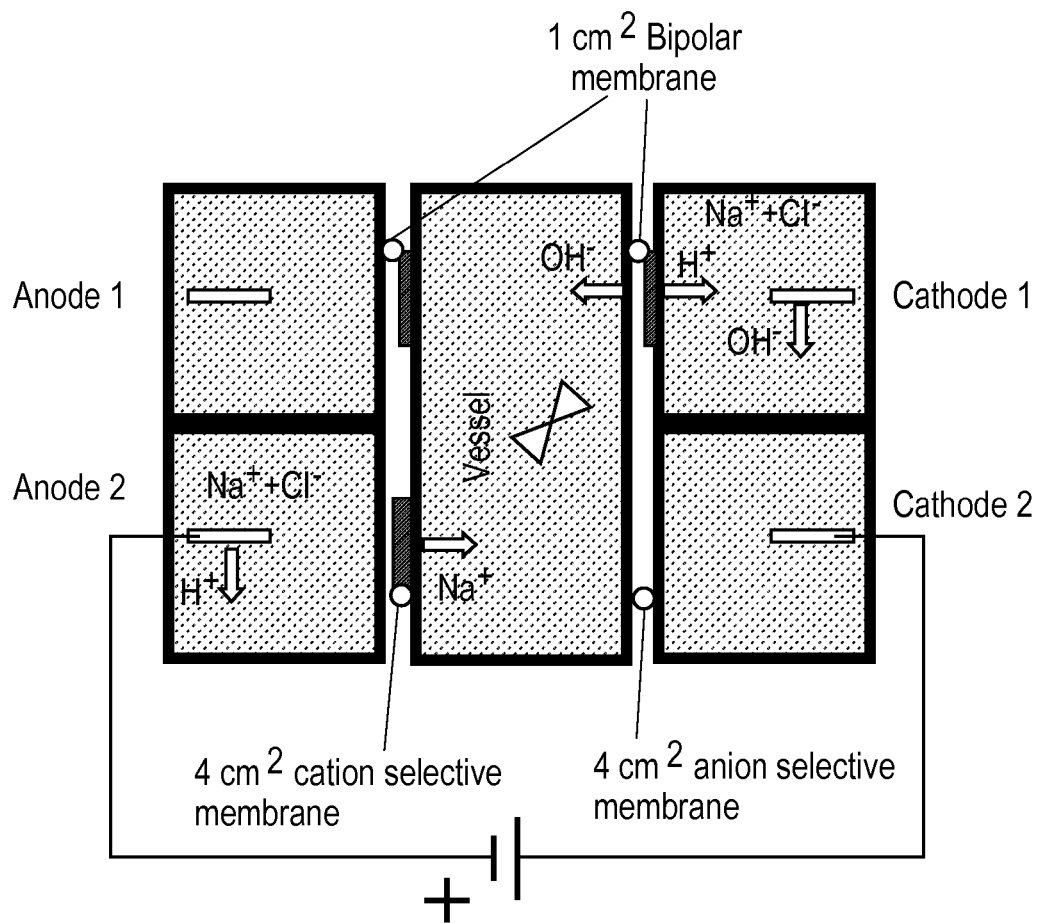
FIG. 16 illustrates an apparatus configuration for titrating a solution in the vessel with NaOH.

An apparatus for modifying the pH and ion concentration in a central vessel was designed and tested. The apparatus is depicted in FIG. 14. The apparatus was configured by placement of different membranes at different locations as shown as shown in FIGS. 15 and 16. FIG. 15 illustrates a configuration used for co-injection of protons and chloride ions into the vessel. FIG. 16 illustrates a configuration used for co-injection of hydroxide and sodium ions into the vessel.

Figure 17:
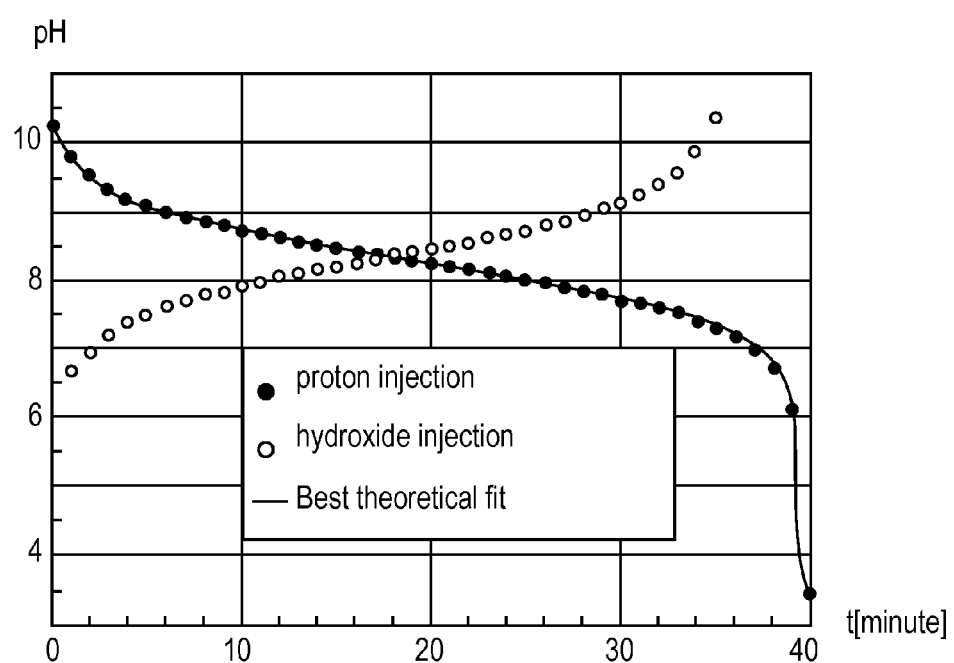
FIG. 17 illustrates electrical titration of a Tris buffer.

Electrical titration of a 20 mM Tris buffer in the 100 ml Vessel was achieved with HCL using the configuration of FIG. 15 and titration of the same buffer with NaOH using the configuration of FIG. 16. Briefly, in the FIG. 15 configuration, the top-right hydroxide injector and the bottom-left cation injector/extractor were muted when the vessel was titrated with HCl and the current applied as shown. Specifically, the electrical current was driven from Anode 1 to Cathode 2 in FIG. 15. The starting solutions were as follows: 20 mM Tris base in 500 mM NaCl in the vessel and 500 mM NaCl in the side chambers. The starting pH in the vessel was 10.45. An injection current was set at 100 mA in the FIG. 15 configuration and pH in the vessel was measured with a glass pH meter. As shown in FIG. 17 ("proton injection," shown in graph from top left to bottom right), 40 minutes of co-injection of protons and chloride ions in the configuration of FIG. 15 reduce 4 the pH to 3.5. At the 40-minute point, the configuration was changed to that of FIG. 16. In the FIG. 16 configuration, the top-left proton injector and the bottom-right anion injector/extractor are muted when the vessel is titrated with NaOH. In the FIG. 16 configuration, electrical current (100 mA) was driven from Anode 2 to Cathode 1. As seen in FIG. 17 ("hydroxide injection," shown in graph from bottom left to top right), application of current in the FIG. 16 configuration for 35 additional minutes titrated the solution in the vessel back to pH 10.45. This demonstrated the feasibility of increasing and decreasing the pH in the vessel.

Example 2

Figure 18:
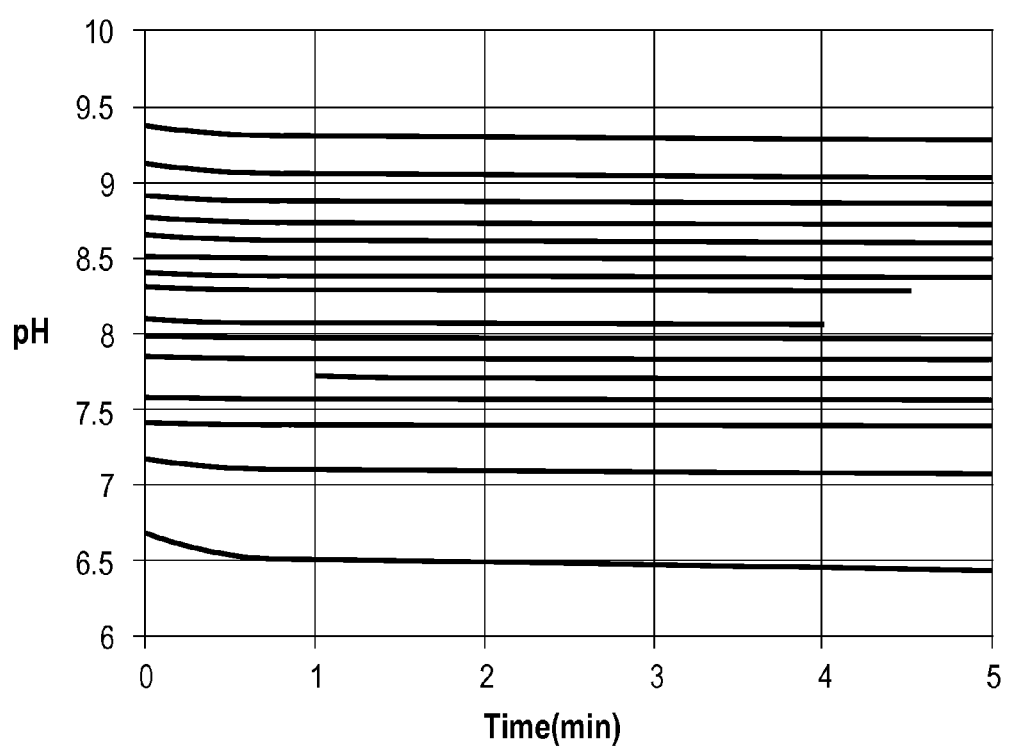
FIG. 18 illustrates pH stability of a solution in a vessel.
Figure 19:
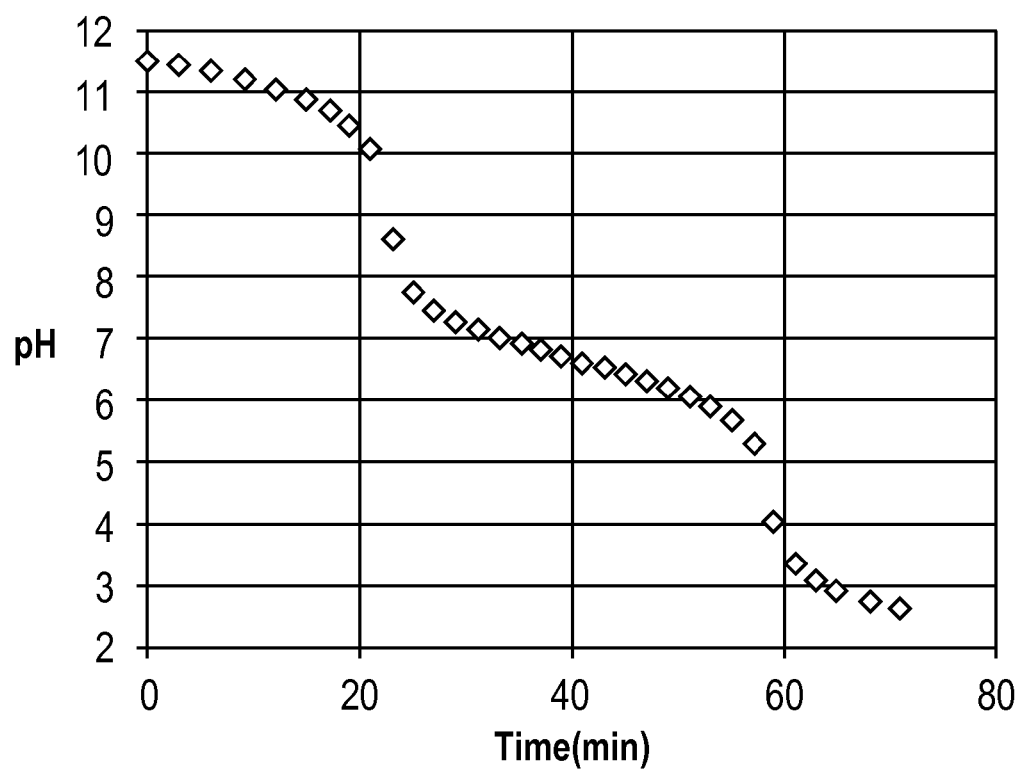
FIG. 19 illustrates results of electric titration of PBS.

In another experiment, pH stability of the vessel solution in the absence of current was demonstrated. The initial pH was 9.6. Protons and chloride ions were injected at 100 mA for 2 minutes (~10-4 mole of each ion per shot). The current was then turned off and the phH was monitored for 5 minutes. The current was then turned on again for 2 minutes and this cycle was repeated 17 times in total. The results of this experiment are shown in FIG. 18 in which different lines correspond to consecutive injections (i.e., when current was on). Within the Tris buffering range, the pH was found to vary by less than 0.03 units. The pH variation resulted from "relaxation" of pH gradients in the vessel. These gradients relaxed within 2 minutes. After relaxation, the pH was stable (in the buffering range) to better than 0.005 units.

Example 3

This Example shows electrical titration of phosphate buffer. Dulbecco's phosphate buffer saline was adjusted manually to pH=11.49 in a 100 ml vessel in the configuration shown in FIG. 15 allowing for electrical titration (i.e., injection) of protons and chloride ions into the vessel. The current applied was ~100 mA. As shown in FIG. 18, the pH dropped as a function of time, but in three stages reflective of the three pKa values characterizing phosphate buffer.

Example 4

This Example shows increasing and decreasing salt concentration in the vessel. Salt concentration in the vessel was increased using the configuration of FIG. 21 and salt concentration in the vessel was decreased using the configuration of FIG. 20. Thus, in FIGS. 21 and 20, the two top hydroxide and proton injectors shown were inactive.

Figure 20:
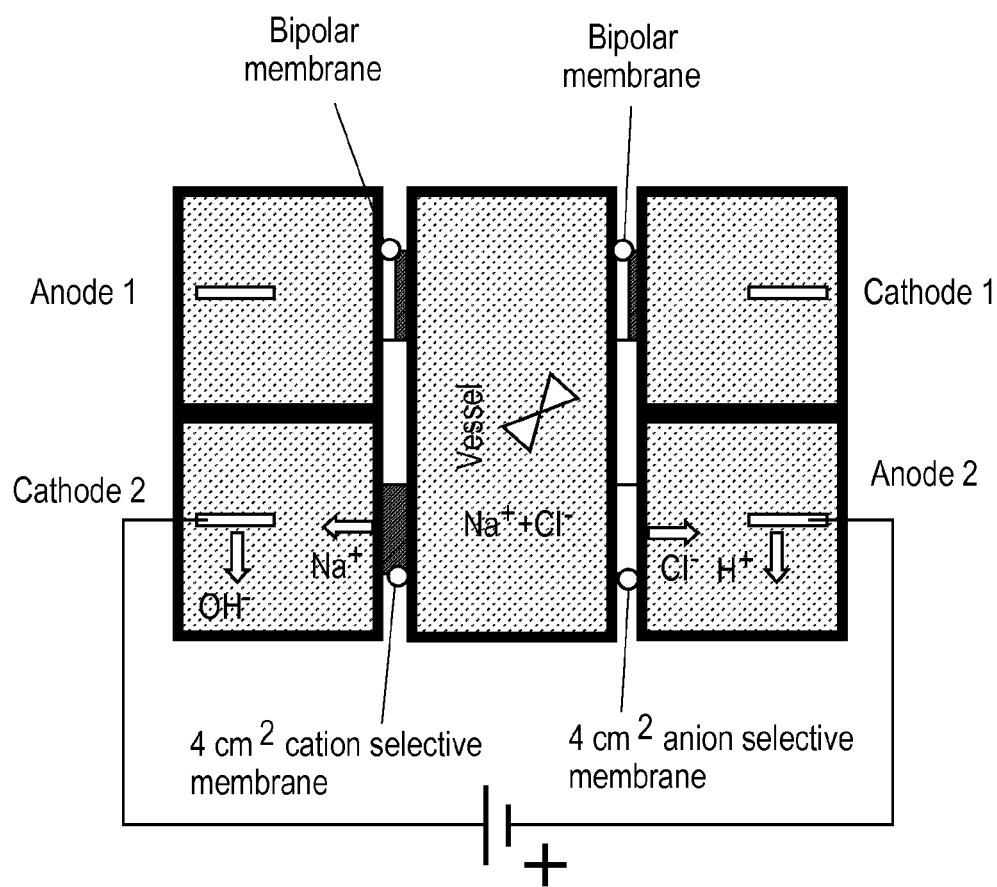
FIG. 20 illustrates an apparatus configuration for decreasing salt concentration in a vessel.
Figure 21:
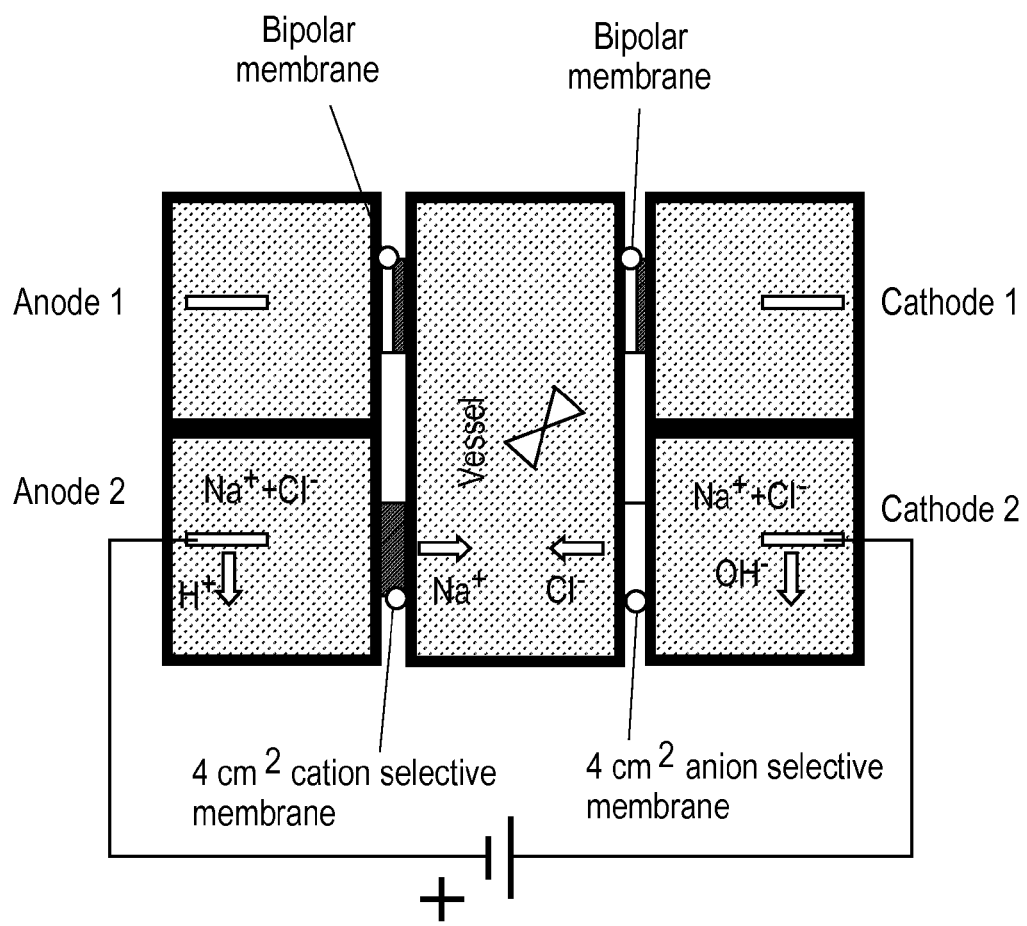
FIG. 21 illustrates an apparatus configuration for increasing salt concentration in a vessel.

As shown in FIG. 21, the bottom-left chamber was used as a cation injector (sodium ions in the present example) and the bottom-right chamber was used as an anion injector (chloride ions in the present example). As shown in FIG. 20, the bottom-left chamber was used as a cation extractor (sodium ions in the present example) and the bottom-right chamber was used as an anion extractor (chloride ions in the present example). Electrical current was driven from Anode 2 to Cathode 2 in both configurations. Starting solutions were 500 mM NaCl in the anion and cation injector chambers and 20 mM NaCl in the vessel.

Figure 22:
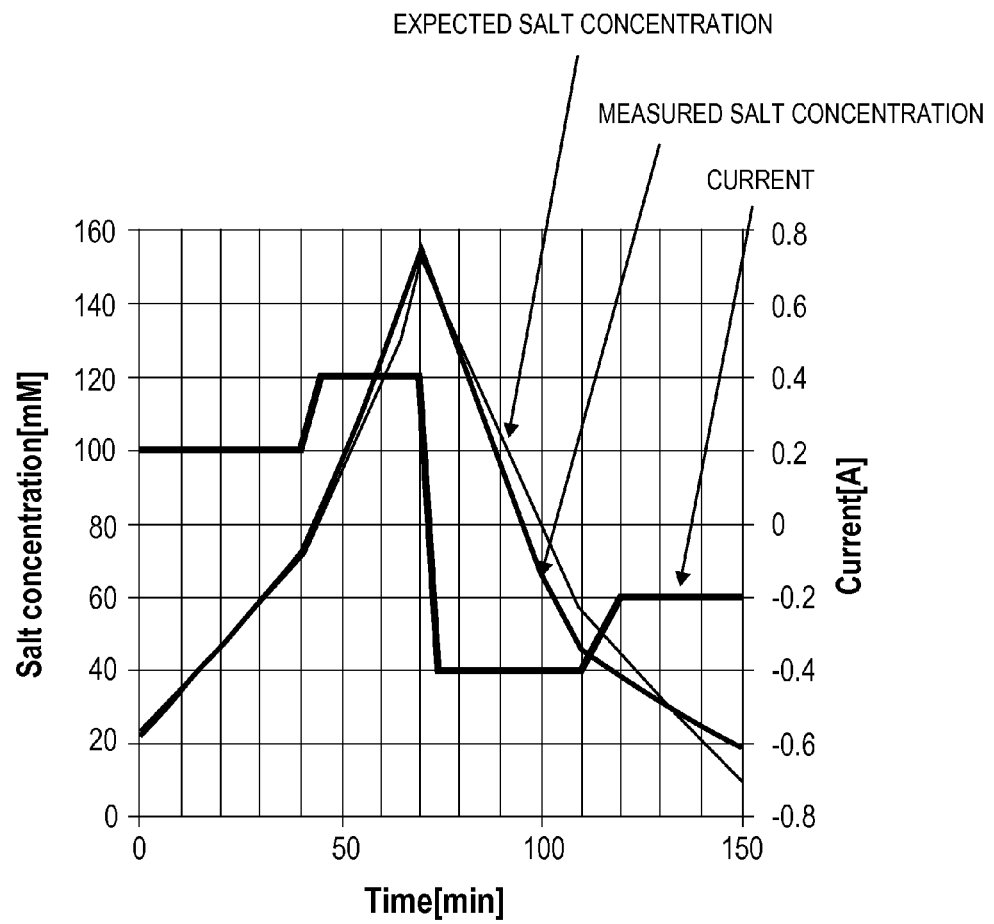
FIG. 22 illustrates results of electrically inducing increases and decreases in salt concentration in a vessel.

The electrical current profile as a function of time is shown in FIG. 22. Positive current amounts for co-injection of sodium and chloride ions were as depicted in FIG. 21. Negative current amounts for co-extraction of sodium and chloride ions were as depicted in FIG. 20. "Expected salt concentration" was calculated based on the applied current and is shown in FIG. 22.

Salt concentration was increased in 70 minutes from 20 mM to ~150 mM by applying positive current in the configuration of FIG. 21. The salt concentration was then reduced back to ~20 mM by application of a negative current for additional 80 minutes in the configuration of FIG. 20. FIG. 22 thus demonstrates increasing and decreasing ion concentration in the vessel using some of the disclosed methods and apparatuses described herein.

Example 5

This Example shows pH control of buffer flowing passed a pH meter.

The following data was collected from a system that contained solution reservoir, peristaltic pump, proton injector, and pH meter connected together by a channel. A pump drove a solution from a reservoir passed a proton injector, pH meter, and out to waste. The proton injector modified the pH of the flowing solution, and the pH meter monitored its pH level.

Figure 25:
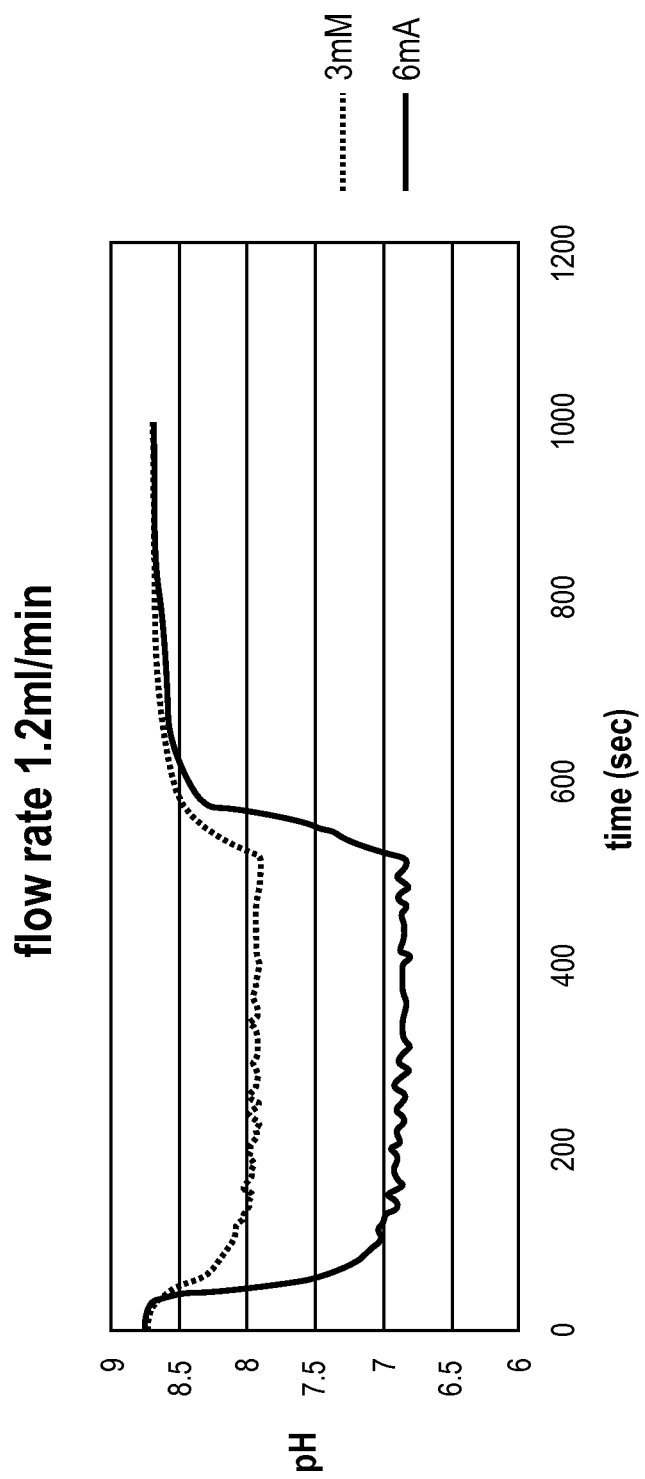
FIG. 25 illustrates results from flowing buffer passed a proton injector under 3 mA (top line) or 6 mA (bottom line).

Experimental Conditions:
Flow rate: 1.2 ml/min
Buffer content: 4 mM phosphate, 100 mM NaCl, pH 8.7
Injector current: t=0: 3 mA/6 mA
  t=520 sec: 0 mA
The resulting pH modulation as a function of time is presented in FIG. 25.

Example 6

Figure 29:
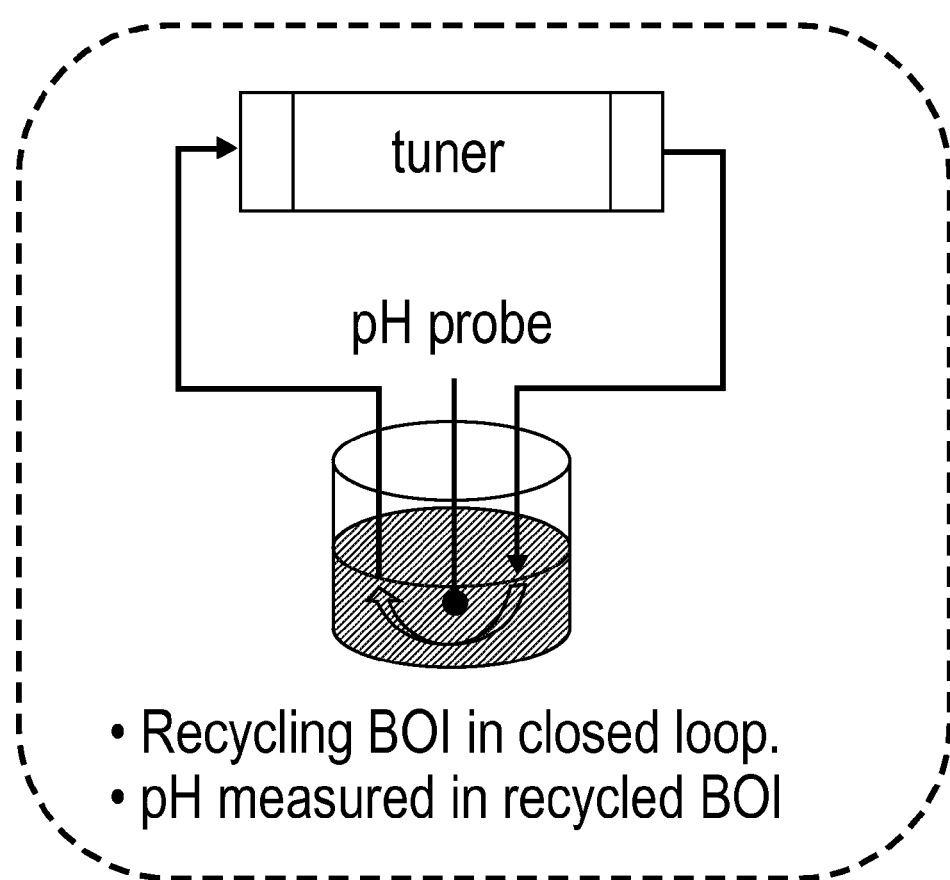
FIG. 29 illustrates a configuration of a tuner in which the output buffer is recycled.

This example shows that pH and conductivity can be independently controlled. Using an apparatus generally configured as shown in FIG. 29, the ability to control pH without affecting conductivity, and the ability to control conductivity without affecting pH was determined.

Figure 26:
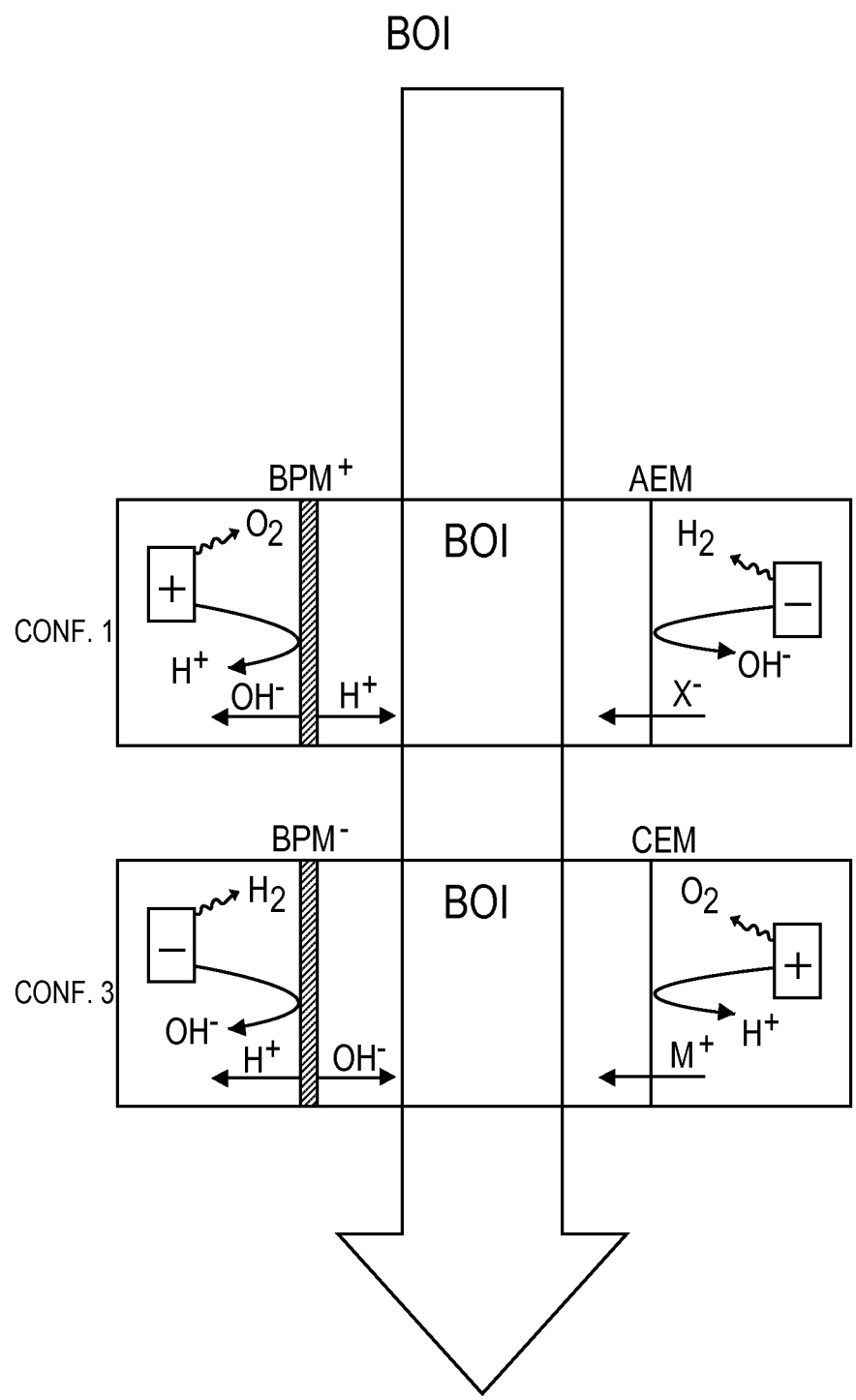
FIG. 26 illustrates a tuner configuration which allows for increasing ionic strength in the buffer of interest (BOI) while keeping pH constant.

The tuner configuration shown in FIG. 26 was used in which the buffer of interest ("BOI") was 50 mM TEA and the "donor" buffer was 25 mM TEA, 500 mM $Na_2SO_4$. Upon application of current, conductivity increased while pH remained essentially constant.

Figure 27:
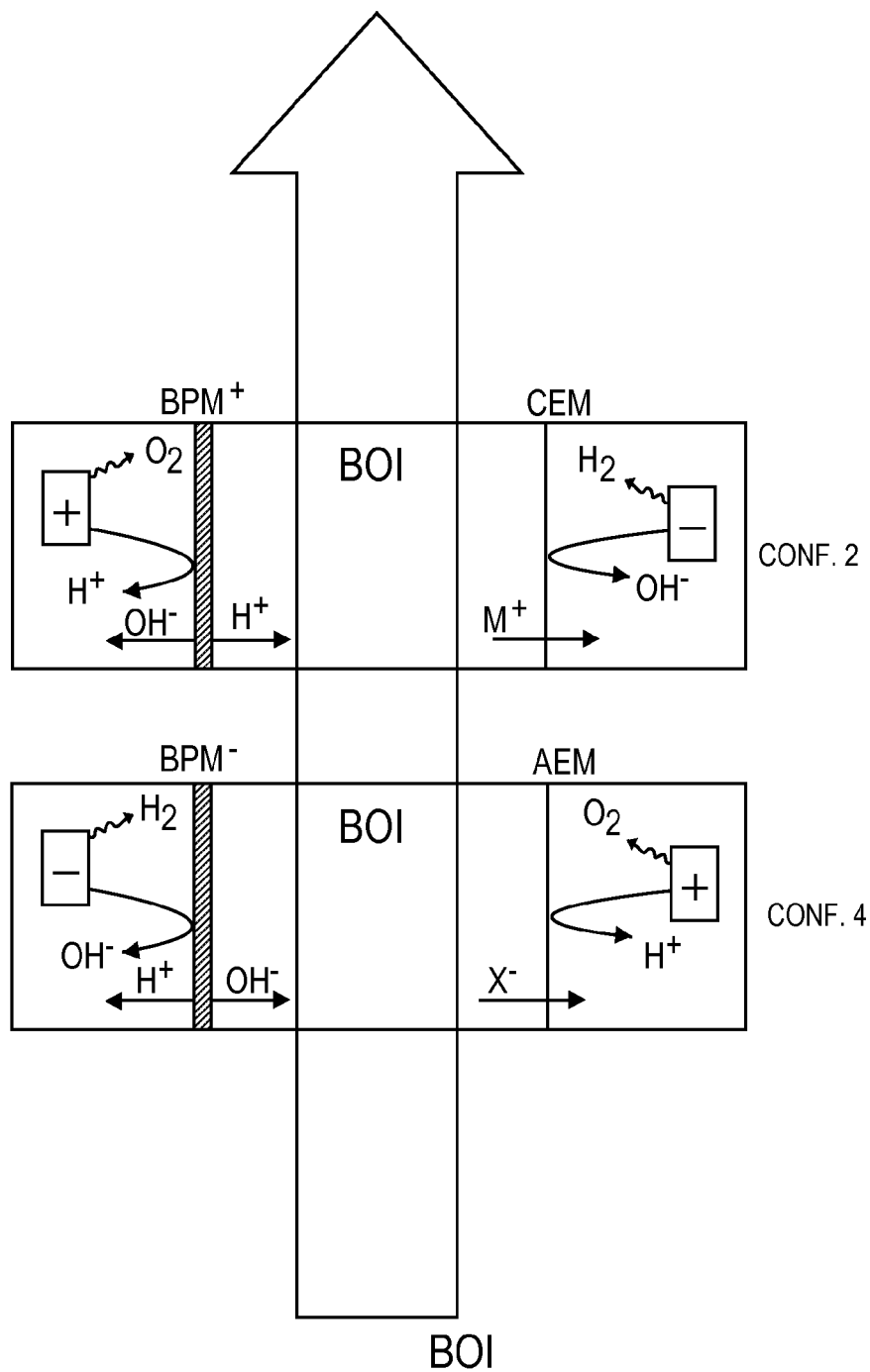
FIG. 27 illustrates a tuner configuration which allows for decreasing ionic strength in the buffer of interest (BOI) while keeping pH constant.
Figure 28:
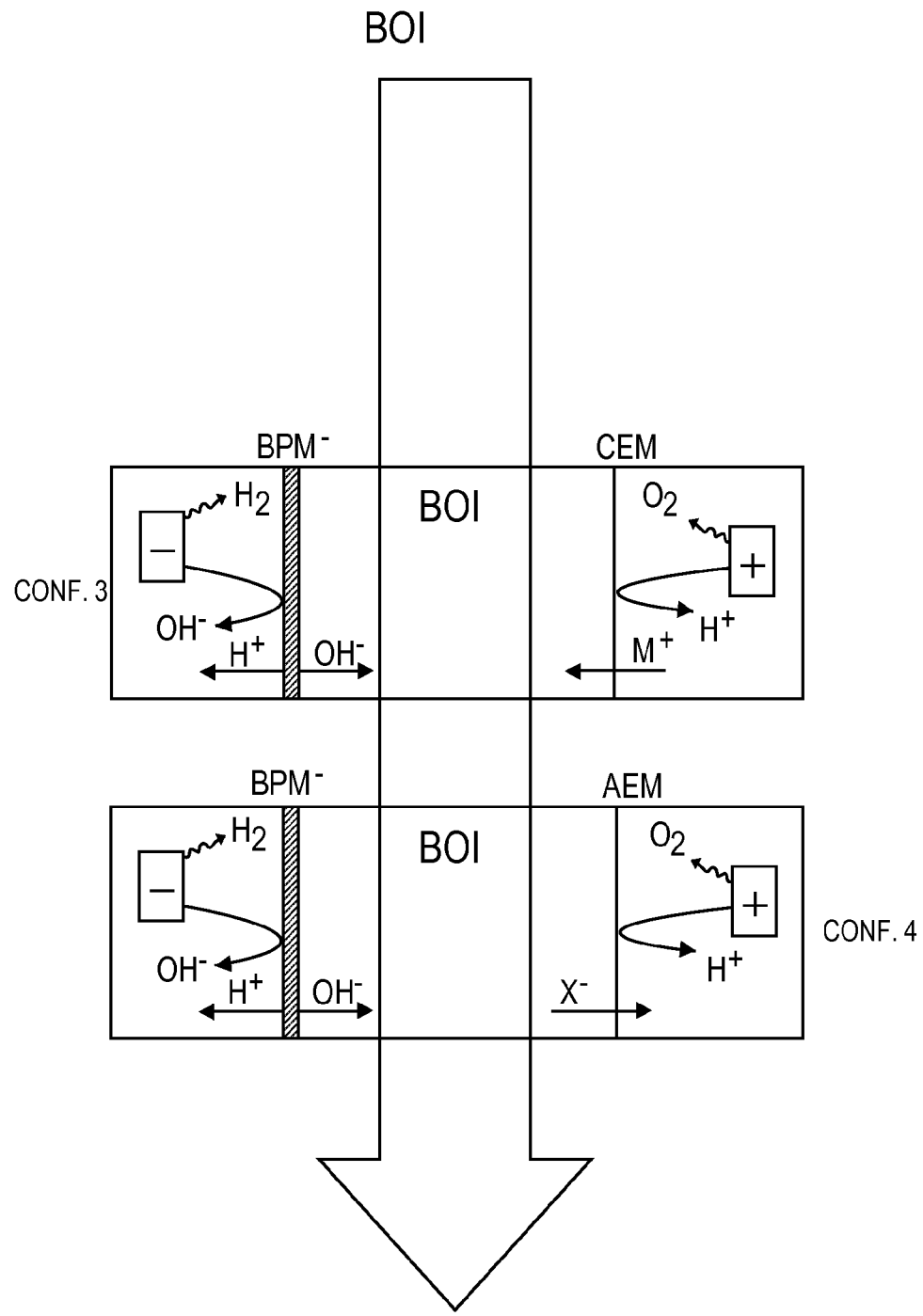
FIG. 28 illustrates a tuner configuration which allows for increasing pH in the buffer of interest (BOI) while keeping ionic strength constant.

The tuner configuration shown in FIG. 27 was used in which the buffer of interest ("BOI") was 50 mM acetate, 500 mM $Na_2SO_4$ and the "donor" buffer was 200 mM phosphate. Upon application of current, conductivity decreased while pH remained essentially constant.

The tuner configuration shown in FIG. 27 was used in which the buffer of interest ("BOI") was 50 mM TEA and the "donor" buffer was 25 mM TEA, 500 mM $Na_2SO_4$. Upon application of current, conductivity remained fairly constant while pH increases occurred. The pH increases occurred within the buffering zone of the buffer. When pH increased and reached close to the pKa of the amines, the selectivity of the anion exchange membrane (AEM) decreased, resulting in permeation of cations into the BOI with the electric field, and thereby no longer blocked conductivity increases.

Figure 30:
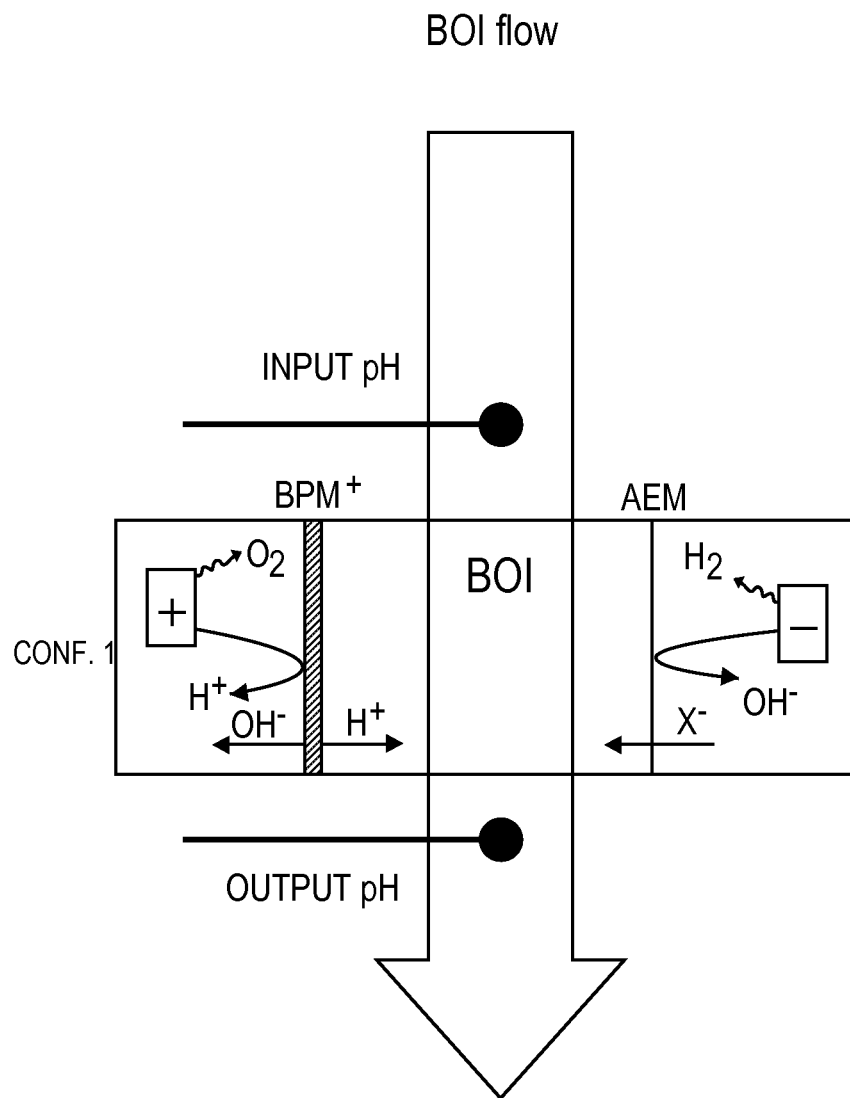
FIG. 30 illustrates a configuration of a tuner in which the output buffer is not recycled.

A non-recycled tuner configured as shown in FIG. 30 was also tested. Output pH was found to sharply change upon the presence of current, with the amount of pH change being a function of flow rate.

The term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety.

What is claimed is:

1. An apparatus for controlling pH and/or ionic strength in a vessel, the apparatus comprising,
    a. a vessel in fluid communication with a first side chamber and a second side chamber, wherein the vessel does not comprise an electrode; and
    b. an anion and proton injector comprising:
        the first side chamber divided from the vessel by an anion selective membrane but not by a cation selective membrane, wherein the first side chamber comprises a first cathode; and
        the second side chamber divided from the vessel by a bipolar membrane, wherein the second side chamber comprises a first anode;
    wherein the first anode and first cathode form a circuit connected via a solution, when present, in the vessel and the first and second side chambers.

2. The apparatus of claim 1, wherein the vessel is a reservoir.

3. The apparatus of claim 1, wherein the vessel is tubing or a channel.

4. The apparatus of claim 3, wherein the tubing or channel forms a recycling loop.

5. The apparatus of claim 3, wherein the tubing or channel draws from a reservoir and outputs to a device or container other than the reservoir.

6. The apparatus of claim 1, further comprising one or more of:
    a conductivity gauge in fluid communication with the vessel;
    a pH meter in fluid communication with the vessel;
    an electronic controller for the electrodes;
    a pump positioned to pump a solution through the vessel.

7. The apparatus of claim 1, wherein the vessel is in fluid communication with a chromatography column or other chromatography support, a mass spectrometer, capillary electrophoresis, or other analytical equipment.

8. The apparatus of claim 1, wherein the vessel comprises a molecular weight cutoff membrane that prevents movement of macromolecules into the side chambers.

9. The apparatus of claim 8, wherein the vessel comprises a buffered solution.

10. The apparatus of claim 9, wherein the solution comprises one or more cell.

11. The apparatus of claim 1, the apparatus further comprising
    c. a cation and hydroxide ion injector comprising:
        a third side chamber in fluid communication with the vessel and divided from the vessel by a cation selective membrane, the third side chamber comprising a second anode; and
        a fourth side chamber in fluid communication with the vessel and divided from the vessel by a bipolar membrane, the fourth side chamber comprising a second cathode,
        wherein the second anode and the second cathode are capable of forming a circuit connected via a solution, if present, in the vessel and the third and fourth side chambers.

12. The apparatus of claim 11, the apparatus further comprising;
    d. an anion and cation extractor comprising:
        the fifth side chamber in fluid communication with the vessel and divided from the vessel by a cation selective membrane, the fifth side chamber comprising a third cathode; and
        the sixth side chamber in fluid communication with the vessel and divided from the vessel by an anion selective membrane, the sixth side chamber comprising a third anode,
        wherein the third anode and the third cathode are capable of forming a circuit connected via a solution, when present, in the vessel and the fifth and second side chambers.

13. The apparatus of claim 1, wherein the apparatus comprises:
    i. a cation and hydroxide ion injector comprising:
        a. the first side chamber in fluid communication with the vessel and divided from the vessel by a cation selective membrane, wherein the electrode of the first chamber is a first anode; and
        b. the second side chamber in fluid communication with the vessel and divided from the vessel by a bipolar membrane, wherein the electrode of the second side chamber is a first cathode, wherein the second anode and the second cathode are capable of forming a circuit connected via a solution, if present, in the vessel and the first and second side chambers.

14. The apparatus of claim 1, wherein the apparatus comprises:
    i. an anion and cation injector comprising:
        a. the first side chamber in fluid communication with the vessel and divided from the vessel by an anion selective membrane, wherein the electrode of the first side chamber is a first cathode; and
        b. the second side chamber in fluid communication with the vessel and divided from the vessel by a cation selective membrane, wherein the electrode of the second side chamber is a first anode, wherein the first anode and the first cathode are capable of forming a circuit connected via a solution, if present, in the vessel and the first and second side chambers.

15. The apparatus of claim 14, the apparatus further comprising;
 iii. an anion and proton injector comprising:
  a. a third side chamber in fluid communication with the vessel and divided from the vessel by an anion selective membrane, the third side chamber comprising a second cathode; and
  b. a fourth side chamber in fluid communication with the vessel and divided from the vessel by a bipolar membrane, the fourth side chamber comprising a second anode, wherein the second anode and the second cathode are capable of forming a circuit connected via a solution, if present, in the vessel and the third and fourth chambers; and
 iv. a cation and hydroxide ion injector comprising:
  a. a fifth side chamber in fluid communication with the vessel and divided from the vessel by an cation selective membrane, the fifth side chamber comprising a third anode; and
  b. a sixth side chamber in fluid communication with the vessel and divided from the vessel by a bipolar membrane, the sixth side chamber comprising a third cathode, wherein the third anode and the third cathode form a circuit connected via a solution in the vessel and the fifth and sixth side chambers.

16. The apparatus of claim 14, the apparatus further comprising
 ii. a proton injector and cation extractor comprising:
  a. a third side chamber in fluid communication with the vessel and divided from the vessel by an cation selective membrane, the third side chamber comprising a second cathode; and
  b. a fourth side chamber in fluid communication with the vessel and divided from the vessel by a bipolar membrane, the fourth side chamber comprising a second anode, wherein the second anode and the second cathode are capable of forming a circuit connected via a solution, if present, in the vessel and the third and fourth side chambers; and
 iii. a hydroxide ion injector and anion extractor comprising:
  a. a fifth side chamber in fluid communication with the vessel and divided from the vessel by an anion selective membrane, the fifth side chamber comprising a third anode; and
  b. a sixth side chamber in fluid communication with the vessel and divided from the vessel by a bipolar membrane, the sixth side chamber comprising a third cathode, wherein the third anode and the third cathode are capable of forming a circuit connected via a solution, if present, in the vessel and the fifth and sixth side chambers.

17. The apparatus of any of claims 1, wherein the apparatus comprises:
 i. a proton injector and cation extractor comprising:
  a. the first side chamber in fluid communication with the vessel and divided from the vessel by an cation selective membrane, wherein the electrode of the first side chamber is a first cathode; and
  b. a second side chamber in fluid communication with the vessel and divided from the vessel by a bipolar membrane, wherein the electrode of the second side chamber is a first anode, wherein the first anode and the first cathode are capable of forming a circuit connected via a solution, when present, in the vessel and the first and second side chambers.

18. The apparatus of claim 1, wherein the apparatus does not comprise a vacuum or other device for removal of excess gas.

19. The apparatus of claim 1, wherein the vessel comprises a mixing system.

* * * * *